US 8,996,134 B2

(12) United States Patent
Duncan et al.

(10) Patent No.: US 8,996,134 B2
(45) Date of Patent: Mar. 31, 2015

(54) IMPLANTABLE LEAD

(75) Inventors: Jeffrey B. Duncan, Flagstaff, AZ (US); Aaron J. Hopkinson, Flagstaff, AZ (US); Thomas R. McDaniel, Flagstaff, AZ (US); Michael J. Vonesh, Flagstaff, AZ (US); Jason M. Wiersdorf, Flagstaff, AZ (US)

(73) Assignee: W. L. Gore & Associates, Inc., Newark, NJ (US)

( * ) Notice: Subject to any disclaimer, the term of this patent is extended or adjusted under 35 U.S.C. 154(b) by 285 days.

(21) Appl. No.: 12/615,122

(22) Filed: Nov. 9, 2009

(65) Prior Publication Data
US 2010/0121421 A1   May 13, 2010

Related U.S. Application Data

(63) Continuation-in-part of application No. 12/605,302, filed on Oct. 23, 2009, now Pat. No. 8,364,281.

(60) Provisional application No. 61/112,600, filed on Nov. 7, 2008.

(51) Int. Cl.
    *A61N 1/00*    (2006.01)
    *A61N 1/05*    (2006.01)
(52) U.S. Cl.
    CPC ............... *A61N 1/05* (2013.01); *A61N 1/0563* (2013.01)
    USPC ........................................................ 607/122
(58) Field of Classification Search
    USPC ................................................ 607/115–123
    See application file for complete search history.

(56) References Cited

U.S. PATENT DOCUMENTS

| 3,953,566 A | 4/1976 | Gore |
| 4,096,227 A | 6/1978 | Gore |
| 4,149,528 A | 4/1979 | Murphy |

(Continued)

FOREIGN PATENT DOCUMENTS

| CH | 656313 | 5/1982 |
| DE | 3043189 | 11/1980 |
| WO | 2005/081681 | 9/2005 |

OTHER PUBLICATIONS

ISO TC 150/SC 6 N Implants for surgery—Active implantable medical devices—Part x: Four-pole connector system for implantable cardiac rhythm management devices. © ISO 2006 All Rights Reserved.

(Continued)

*Primary Examiner* — Scott Getzow
(74) *Attorney, Agent, or Firm* — Wayne D. House

(57) ABSTRACT

A highly flexible implantable lead that offers improved flexibility, fatigue life and fatigue and abrasion resistance improved reliability, effective electrode tissue contact with a small diameter and low risk of tissue damage during extraction. In one embodiment the lead is provided with both defibrillation electrodes and pacing/sensing electrodes. For defibrillation/pacing leads, the lead diameter may be as small as six French or smaller. The construction utilizes helically wound conductors. For leads incorporating multiple separate conductors, many of the helically wound conductors are arranged in a multi-filar relationship. Preferably, each conductor is a length of wire that is uninsulated at about the middle of its length to create an electrode, wherein the conductor is folded in half at about the middle of the length to create first and second length segments that constitute parallel conductors.

20 Claims, 36 Drawing Sheets

(56) References Cited

U.S. PATENT DOCUMENTS

| | | |
|---|---|---|
| 4,187,390 A | 2/1980 | Gore |
| 4,217,913 A | 8/1980 | Dutcher |
| 4,311,153 A | 1/1982 | Smits |
| 4,357,946 A | 11/1982 | Dutcher et al. |
| 4,484,586 A | 11/1984 | McMickle et al. |
| 4,559,951 A | 12/1985 | Dahl et al. |
| 4,640,983 A | 2/1987 | Comte |
| 4,922,927 A | 5/1990 | Fine et al. |
| 4,947,866 A | 8/1990 | Lessar et al. |
| 4,985,296 A | 1/1991 | Mortimer, Jr. |
| 5,090,422 A | 2/1992 | Dahl et al. |
| 5,148,806 A | 9/1992 | Fukui et al. |
| 5,191,901 A | 3/1993 | Dahl et al. |
| 5,231,996 A | 8/1993 | Bardy et al. |
| 5,246,014 A | 9/1993 | Williams et al. |
| 5,269,810 A | 12/1993 | Hull et al. |
| 5,281,475 A | 1/1994 | Hollenbaugh, Jr. et al. |
| 5,350,419 A | 9/1994 | Bendel et al. |
| 5,358,516 A | 10/1994 | Myers et al. |
| 5,374,287 A | 12/1994 | Rubin |
| 5,456,707 A | 10/1995 | Giele |
| 5,466,252 A | 11/1995 | Soukup et al. |
| 5,466,253 A | 11/1995 | Doan |
| 5,466,254 A | 11/1995 | Helland |
| 5,476,496 A | 12/1995 | Strandberg et al. |
| 5,476,589 A | 12/1995 | Bacino |
| 5,499,981 A | 3/1996 | Kordis |
| 5,515,848 A | 5/1996 | Corbett, III et al. |
| 5,522,872 A | 6/1996 | Hoff |
| 5,522,874 A | 6/1996 | Gates |
| 5,560,986 A | 10/1996 | Mortimer, Jr. |
| 5,609,622 A | 3/1997 | Soukup et al. |
| 5,630,839 A | 5/1997 | Corbett, III et al. |
| 5,676,694 A | 10/1997 | Boser et al. |
| 5,755,762 A | 5/1998 | Bush |
| 5,782,239 A | 7/1998 | Webster, Jr. |
| 5,845,396 A | 12/1998 | Altman et al. |
| 5,874,165 A | 2/1999 | Drumheller |
| 5,928,277 A | 7/1999 | Laske et al. |
| 6,086,582 A | 7/2000 | Altman et al. |
| 6,097,986 A | 8/2000 | Janke et al. |
| 6,104,961 A | 8/2000 | Conger et al. |
| 6,159,565 A | 12/2000 | Campbell |
| 6,181,971 B1 | 1/2001 | Doan |
| 6,265,691 B1 | 7/2001 | Cardineau et al. |
| 6,374,141 B1 | 4/2002 | Sass |
| 6,477,429 B1 | 11/2002 | Conger et al. |
| 6,501,991 B1 | 12/2002 | Honeck et al. |
| 6,505,401 B1 | 1/2003 | Doan |
| 6,546,292 B1 | 4/2003 | Steinhaus et al. |
| 6,704,605 B2 | 3/2004 | Soltis et al. |
| 6,978,185 B2 | 12/2005 | Osypka |
| 6,999,821 B2 | 2/2006 | Jenney et al. |
| 7,020,529 B2 | 3/2006 | Krall et al. |
| 7,049,380 B1 | 5/2006 | Chang et al. |
| 7,158,837 B2 | 1/2007 | Osypka et al. |
| 7,191,016 B2 | 3/2007 | Marshall et al. |
| 7,239,923 B1 | 7/2007 | Tockman et al. |
| 7,366,573 B2 | 4/2008 | Knapp et al. |
| 2003/0023294 A1 | 1/2003 | Krall et al. |
| 2004/0230276 A1 | 11/2004 | Marshall et al. |
| 2005/0049665 A1 | 3/2005 | Brabec et al. |
| 2005/0131511 A1 | 6/2005 | Westlund |
| 2006/0009829 A1 | 1/2006 | Aron et al. |
| 2006/0030918 A1 | 2/2006 | Chinn et al. |
| 2006/0198866 A1 | 9/2006 | Chang et al. |
| 2007/0106144 A1 | 5/2007 | Squeri |
| 2007/0276458 A1 | 11/2007 | Boser |
| 2008/0061472 A1 | 3/2008 | Kennedy et al. |
| 2008/0183261 A1 | 7/2008 | Hammill et al. |
| 2008/0248696 A1 | 10/2008 | Kast et al. |
| 2009/0012591 A1 | 1/2009 | Barker |
| 2009/0071686 A1 | 3/2009 | Boser et al. |
| 2009/0071687 A1 | 3/2009 | Boser et al. |
| 2009/0076577 A1 | 3/2009 | Boser et al. |
| 2009/0076578 A1 | 3/2009 | Boser et al. |
| 2009/0076579 A1 | 3/2009 | Boser et al. |
| 2009/0076580 A1 | 3/2009 | Boser et al. |

OTHER PUBLICATIONS

W.L. Gore & Associates Invents Breakthrough Aircraft Wiring That Outperforms All Existing Wiring in Critical Safety Factors, Apr. 28, 1999. <http://www.thefreelibrary.com/W.+L.+Gore+%26+Associates+Invents+Breakthrough+Aircraft+Wiring+That...-a054497415>.

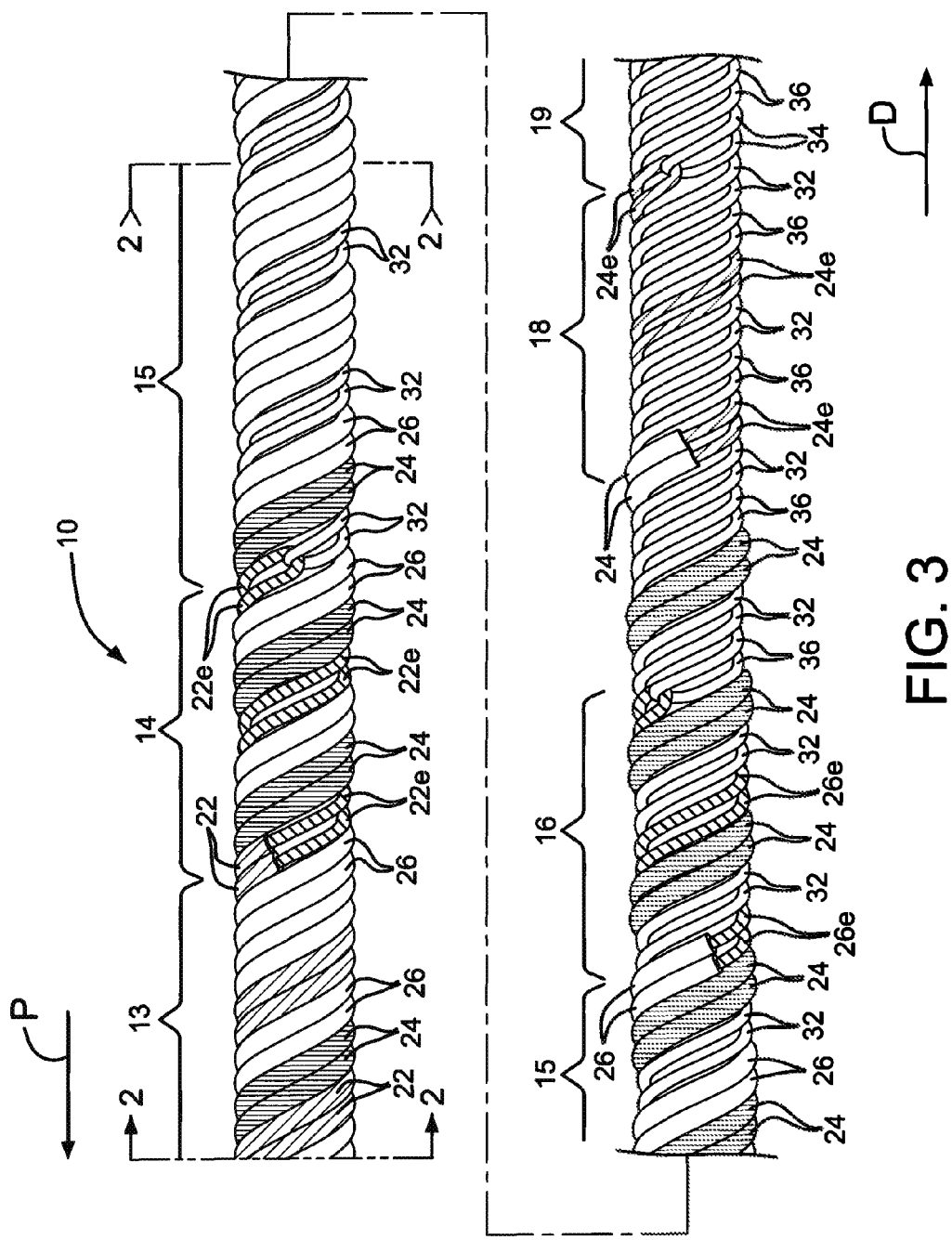

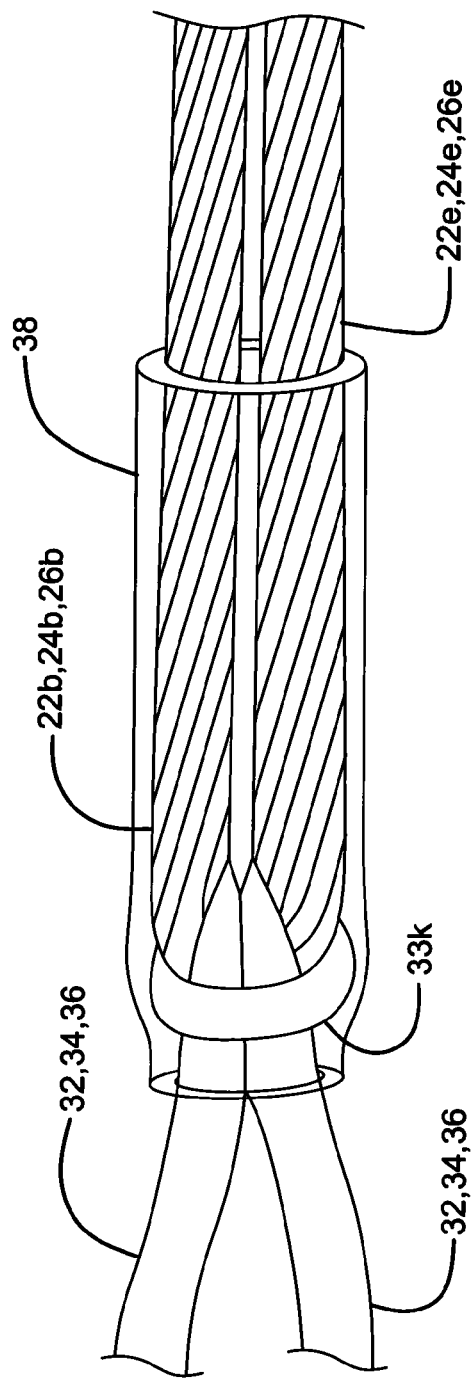

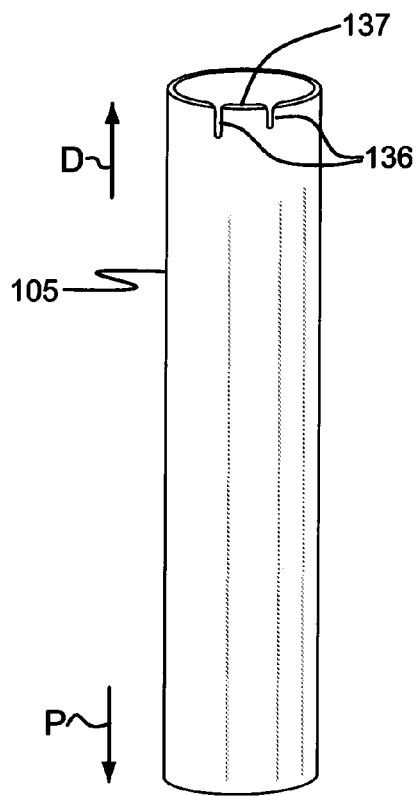
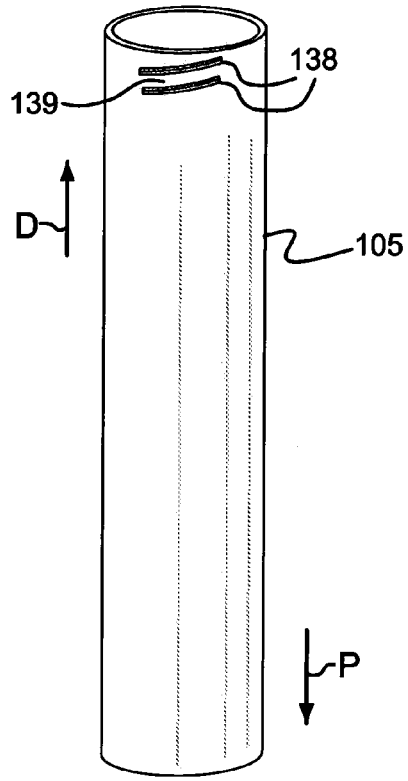
FIG. 14A    FIG. 15A
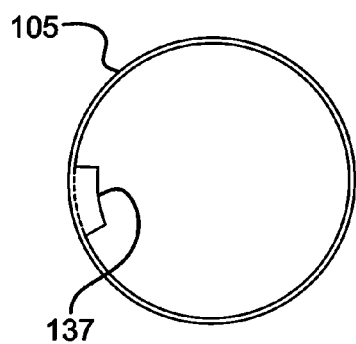
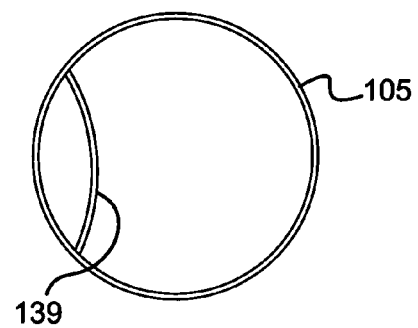
FIG. 14B    FIG. 15B

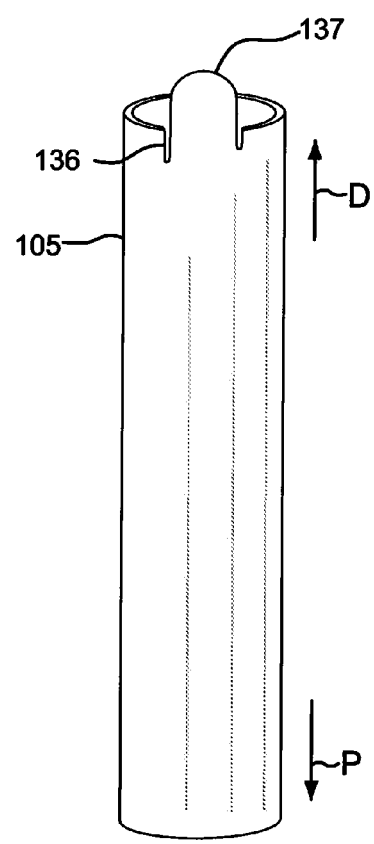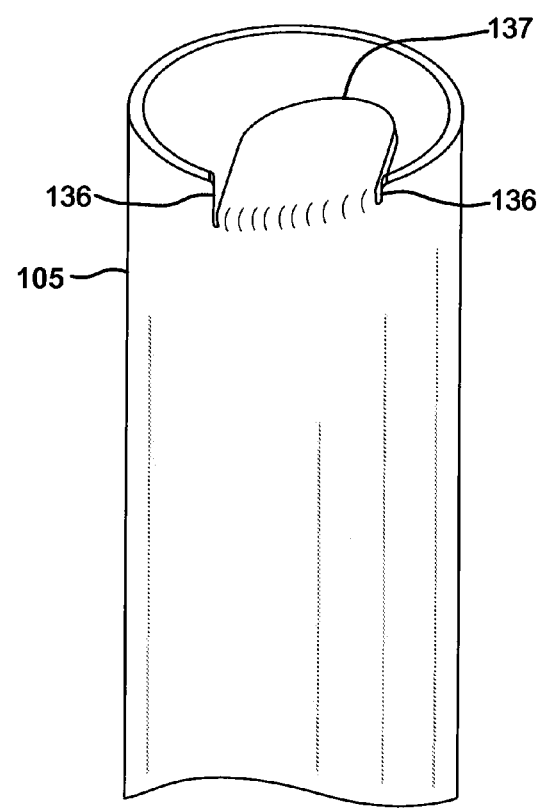
FIG. 16A
FIG. 16B

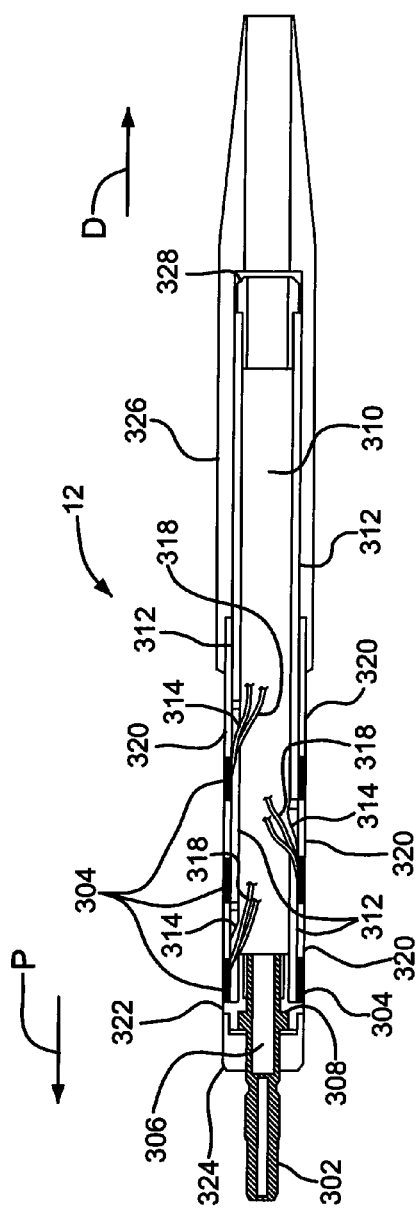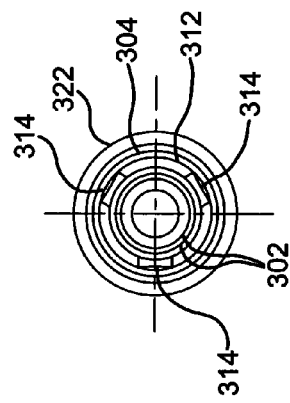
FIG. 18A
FIG. 18B

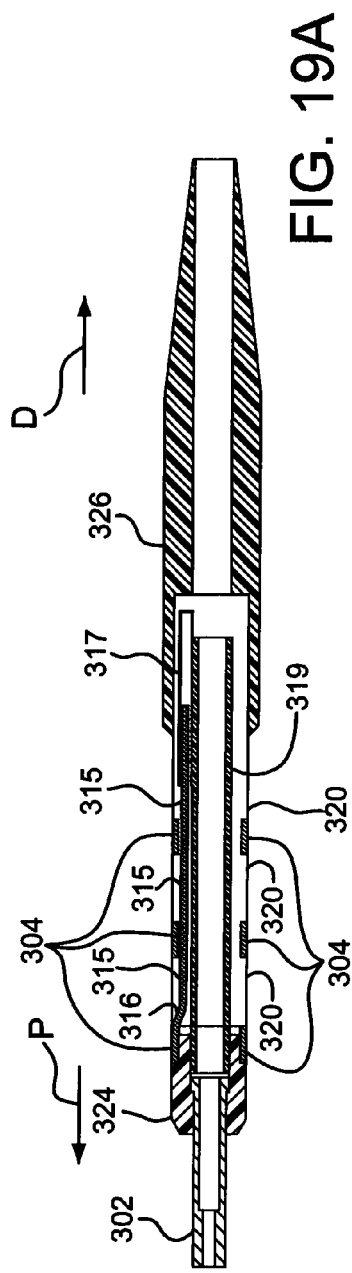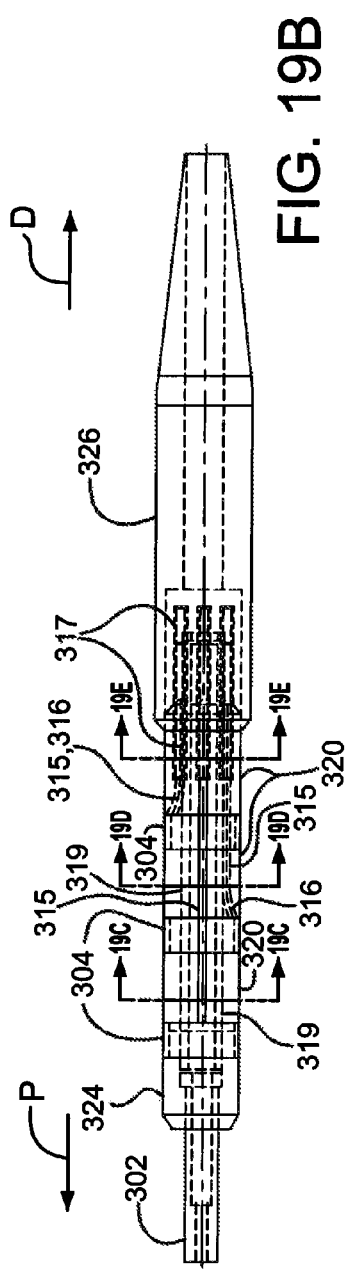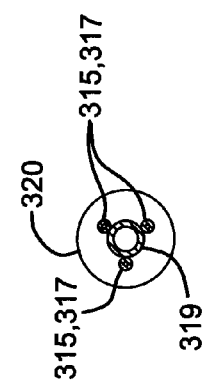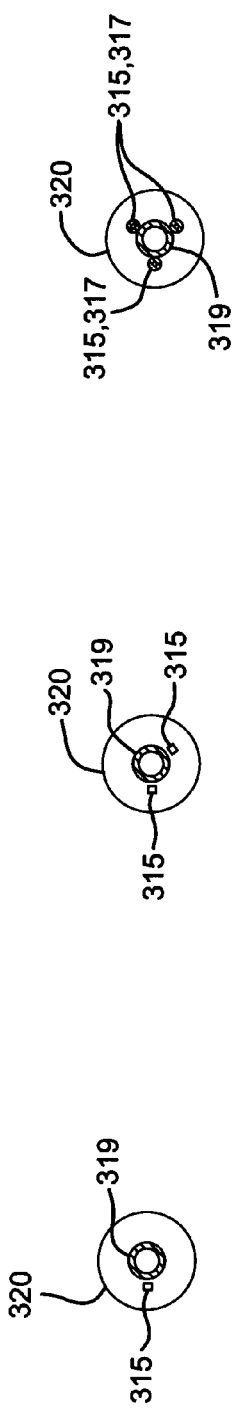

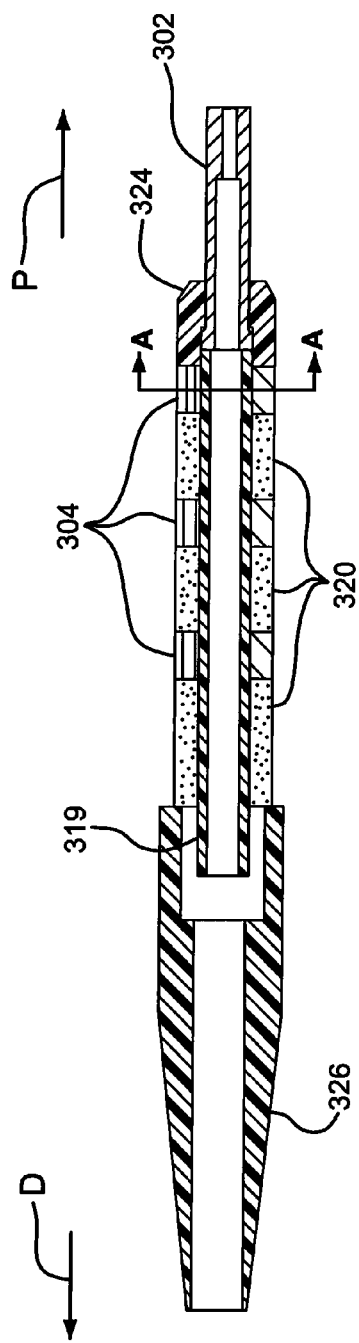
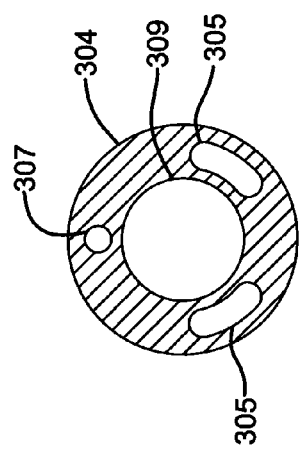
FIG. 20A
FIG. 20B

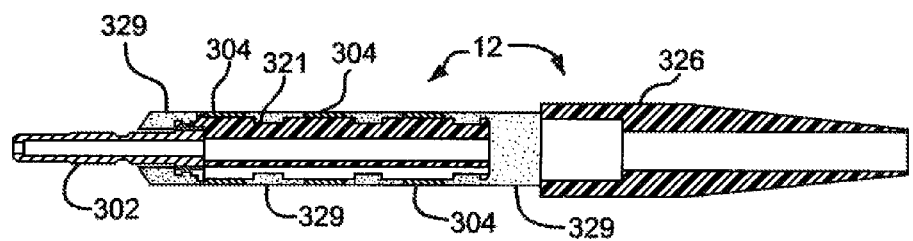
FIG. 21A
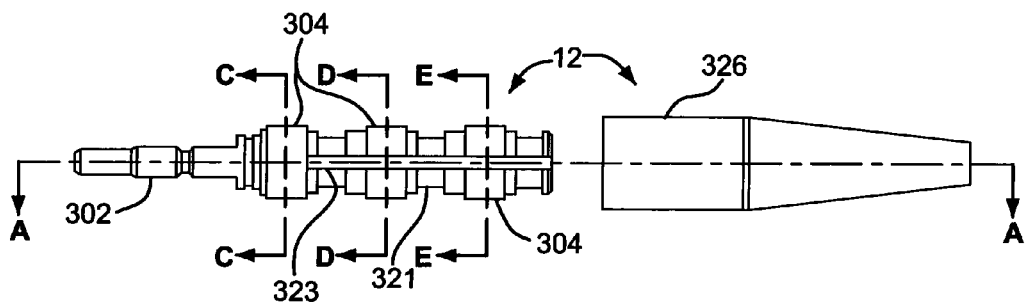
FIG. 21B
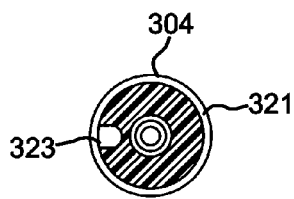   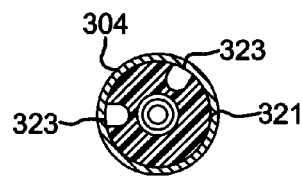   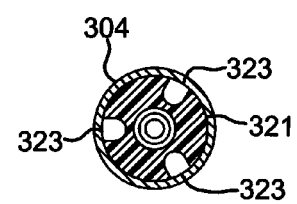
FIG. 21C     FIG. 21D     FIG. 21E

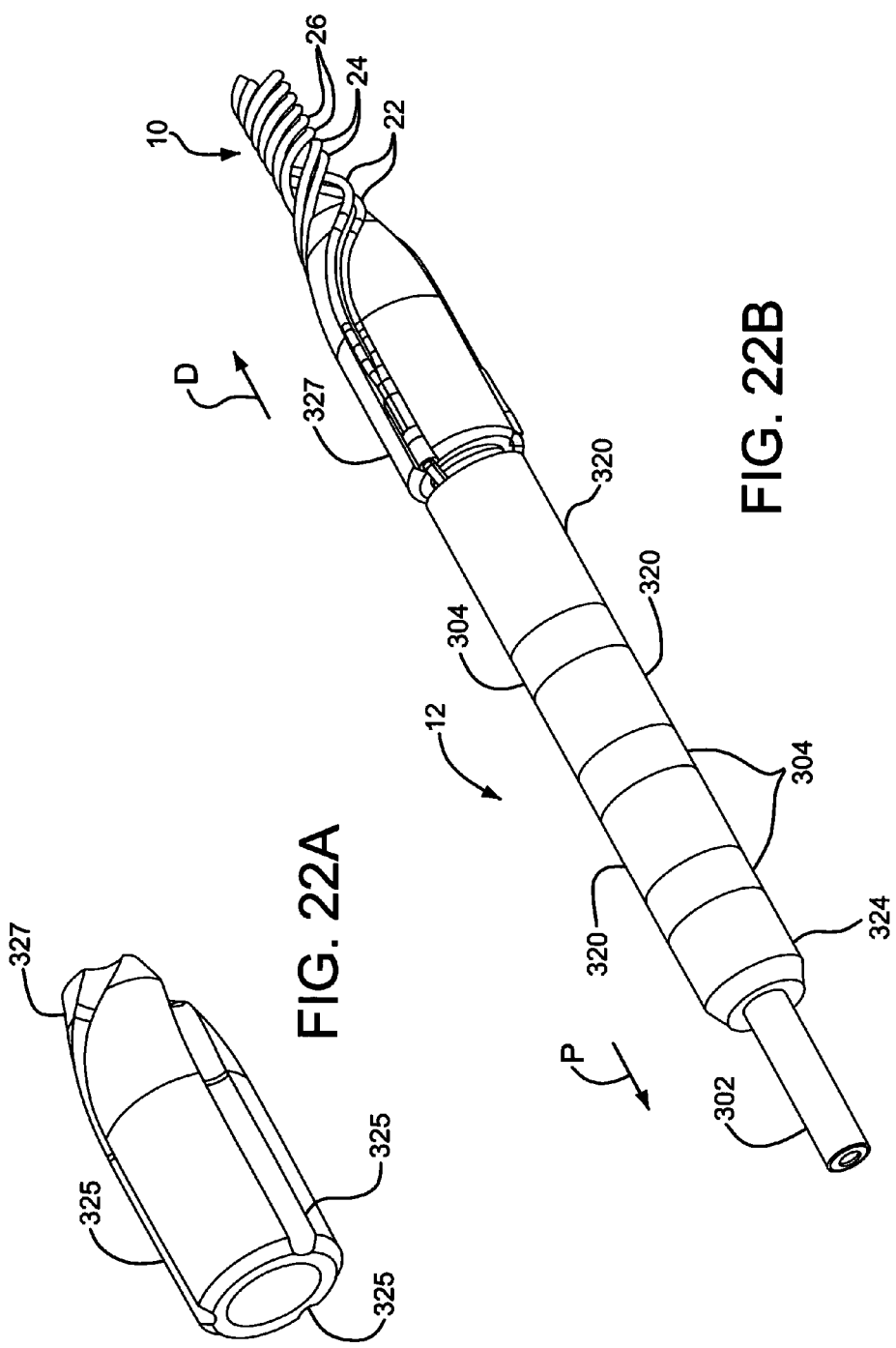

IMPLANTABLE LEAD

CROSS REFERENCE TO RELATED APPLICATIONS

This application is a continuation-in-part of U.S. patent application Ser. No. 12/605,302 filed Oct. 23, 2009 now U.S. Pat. No. 8,364,281, which claims priority to U.S. Patent Application Ser. No. 61/112,600 filed Nov. 7, 2008.

FIELD OF THE INVENTION

The present invention relates to the field of implantable electrophysiology leads including cardiac defibrillation and pacing leads, diagnostic leads and neurological stimulation leads.

BACKGROUND OF THE INVENTION

Implantable medical leads are used in a variety of applications to conduct energy (e.g., electrical, photonic, etc.) between energy sources and various portions of the body. Diagnostic leads are implanted to measure physiological parameters over time, for example blood pressure, or collect and transmit physiological data such as nerve impulses and cardiac rhythm data. Stimulation leads discretely deliver energy to targeted tissues. Neurological stimulation leads are used to block pain, for example. Cardiac stimulation leads are used to deliver low or high voltage electrical energy to pace or defibrillate the heart.

Transvenous defibrillator leads are used for the correction of ventricular or atrial bradycardia, tachycardia and/or fibrillation. Leads of this type are intravenously positioned, and are used to provide a variety of diagnostic, pacing and defibrillation functions. More than one electrode may be provided if it is desired to provide electrodes for defibrillation and for pacing and/or sensing. Typical cardiac leads are positioned into the right atrium and/or the right ventricle. More recently developed leads are positioned into the coronary veins of the left side of the heart for use with cardiac resynchronization therapy (CRT).

Conventional transvenous defibrillator leads use a stranded wire to conduct the electrical energy from the connector at the proximal end of the lead to a coiled defibrillation electrode near the distal end. A discrete connector or junction is generally used between the conductor and the electrode. The junction may be formed by a connector component, a crimp joint, a weld, or combinations of these. Medical leads with discrete connectors may suffer from decreased reliability due to connector interfaces serving as points of failure. Connectors also tend to increase the diameter of leads, at least in the region of the connector. This may lead to increased tissue attachment in these regions and commensurate difficulty in lead extraction (sometimes necessary in cases of infection, dislodgement or lead failure).

The electrode surface of an implantable lead is typically exposed, allowing it to contact or be in close proximity to the desired surface of the tissues or surrounding fluids. Such exposed electrodes have a fundamental disadvantage with tissue ingrowth. The ingrowth and anchoring of tissue into the exposed coil makes the lead difficult to extract and may also adversely affect electrical performance of the lead. Various electrode coverings have been suggested to eliminate or minimize tissue attachment to the electrode. Defibrillation electrodes provided with coverings of porous polymeric materials including polyurethane and polytetrafluoroethylene (hereinafter PTFE) have been described, wherein the penetration of bodily fluids permits electrical conduction through the porous polymer even though the covering itself may be electrically non-conductive. Various electrically conductive coverings such as porous polymeric materials having void spaces partially filled with conductive materials (e.g., carbon) have also been described. These porous coverings may be treated to improve wettability and conductivity.

It has generally been desired to manufacture leads with the smallest possible diameter while providing sufficient electrode area. Other sought after attributes may include isodiametricity, flexibility, flex life, fatigue resistance, abrasion resistance, corrosion resistance, tensile strength, and minimal tissue ingrowth, all of which contribute to good long-term reliability and extractability with minimal risk of trauma.

SUMMARY OF THE INVENTION

An implantable lead is described that offers good flexibility, fatigue resistance and flex life, improved reliability, high abrasion, fatigue, and corrosion resistance, high tensile strength and effective electrode tissue contact with a small, isodiametric profile and low risk of tissue damage during extraction. The lead also offers similar defibrillation impedances and thresholds, pacing impedances and thresholds, and sensing R-wave amplitudes when compared to commercially available leads. In one embodiment the lead is provided with both defibrillation electrodes and pacing/sensing electrodes. For defibrillation/pacing leads, the lead diameter may be as small as six French, five French or even smaller. The lead may optionally be made to have a smaller diameter for portions that reside intravascularly (e.g., 5 French) and have a larger diameter in other regions, for example in portions that reside extravascularly (e.g., 6 French), providing even greater abrasion and crush resistance resulting from greater insulation thickness in those portions. Such varied diameters may be created by using the same materials or sets of materials in each region of different diameter. For example, layers of a lead may be "built up" to create the larger diameter region. A transition in diameter may be present between the regions of differing diameter. Such a transition may take the form of a taper or be more abrupt.

The construction utilizes helically-wound conductors, each of which is preferably made of multi-stranded wire. For leads incorporating multiple separate conductors, many of the helically wound conductors are arranged in a multi-filar relationship. The insulated portions of these conductors are preferably provided with a thin, strong fluoropolymer electrical insulation; a particularly preferred material for this insulation is a non-porous ePTFE provided with an adhesive coating of thermoplastic fluorinated ethylene propylene (FEP), referred to hereinafter as "substantially impermeable ePTFE/FEP insulating tape". ePTFE (expanded polytetrafluoroethylene) is well known in the medical device arts; it is generally made as described by U.S. Pat. Nos. 3,953,566 and 4,187,390 to Gore. The particular tape described herein is slit from a substantially non-porous ePTFE/FEP film having a thickness of about 0.0064 mm, an isopropyl bubble point of greater than about 0.6 MPa, a Gurley No. (permeability) of greater than about 60 (minute/1 square inch/100 cc); (or 60 (minute/6.45 square cm/100 cc)), a density of about 2.15 g/cc and a tensile strength of about 309 MPa in the length direction (i.e., the strongest direction). A 0.0025 mm thickness of this same type of substantially impermeable ePTFE/FEP films was also used in aspects of the construction of leads of the present invention described below. This thinner film will be referred to hereinafter as "thinner substantially impermeable ePTFE/FEP insulating tape". Other layers of fluoropolymer films may be used in addition to the substantially impermeable ePTFE/FEP insulating tape, including porous ePTFE to enhance adhesion, flexibility or other properties.

"Insulation" is defined herein as a material intended to preclude conduction of electrical charge to adjacent tissue or to adjacent insulated electrical conductors. Preferably, portions (e.g., length portions near the distal ends) of at least some conductors are uninsulated and serve as electrodes or portions thereof. As such, the insulated portions of these conductors are continuous with the uninsulated electrode portions, thereby avoiding the use of connectors between the conductors and the electrodes. The lack of conductor-to-electrode connectors enables the construction of an isodiametric lead with high fatigue resistance and tensile strength and enhances reliability.

"Lead body", for purposes of this description, is the portion of the implantable lead located between the termination of the conductors in the proximal connector and the tip assembly, and includes the pacing coil.

For descriptive purposes, the "proximal end" of the lead is considered to be the end provided with at least one electrical connector intended to enable the lead to be connected to a power source or sensing and control system. The "distal end" is the end opposite the proximal end that is typically affixed to a tissue surface, for example the heart. Figures are designated with arrows labeled "P" (proximal) or "D" (distal) to indicate these respective directions.

In one embodiment for cardiac use, the lead includes four electrodes. In sequence, beginning proximally and moving to the distal end, these are the proximal defibrillation electrode (typically positioned in the superior vena cava following implantation; also referred to as SVC electrode), the distal defibrillation electrode (typically positioned in the right ventricle; also referred to as the RV electrode), a sensing electrode adjacent to the distal tip and a pacing electrode located at the distal tip of the lead assembly.

The distal tip may be a "passive fixation" design, commonly known in the art, or an active tip including a helical fixation member that may be rotated by a practitioner at the proximal end of the lead to drive the helical fixation member into and anchor the lead in the heart tissue at a chosen location. When the helical fixation member also serves as the pacing electrode, it is often connected to a helically wound electrical conductor (often referred to as a pacing coil) that is centrally located in the lead and extends to the proximal electrical connector. This conductor serves to provide both a mechanical (rotational) and an electrical connection to the helical fixation member. This helically wound electrical conductor contains a hollow lumen that provides a working channel to allow access for a stylet during implantation and/or extraction. The pacing coil may also include a non-conductive filament wound into the coil as one of the coil filars to improve MRI compatibility. Distal lead tips may also include a means for drug delivery such as a matrix containing elutable therapeutic agents such as anti-inflammatories. Additionally, distal lead tips may include features to reduce risk of perforation of the tissues during and after implantation. These features may include flange-like features that increase the diameter of the distal tip to lower the tendency for perforation to occur. This diameter increase may be achieved through use of shape-memory alloys or polymers, swellable polymers, compliant polymer or elastomeric features, and dissolvable/bioabsorbable materials. These features may also include therapeutic agents for drug delivery.

The electrical conductors providing electrical potential to the other electrodes are preferably arranged in a helical winding disposed around the inner helically wound conductor connected to the pacing electrode. The helical winding of these outer conductors is preferably a multi-filar helical arrangement. In one embodiment, the individual electrical conductors are folded approximately in half to form a 180° bent end that is located distal to the proximal end of the lead, with the portion adjacent to or adjacent to and including the bent end being uninsulated and configured to serve as an electrode. The remaining portion of each of the first and second length segments that constitute the two sides or 'halves' of each of the folded conductors is insulated and extends to the electrical connector located at the proximal end of the lead. The two first and second length segments will typically be adjacent to each other in the multi-filar winding of electrical conductors. The provision of the two first and second length segments allows for the use of a smaller diameter wire to supply the electrode and adds to the flexibility of the lead, reduces the lead diameter, improves fatigue resistance, and provides for redundancy in supplying electrical potential to the electrode.

Additionally, in the construction of both the pacing coil and the winding of the conductors in the lead body, the helically wound wires are constrained in a strained condition. This is accomplished by winding the wires over the mandrel (for the pacing coil) or lead body construction (for the remaining conductors) and maintaining the position and tension in the wires while outer layers are wrapped over the strained conductors with, for example, the fluoropolymer tapes described in the manufacturing descriptions and then heated as described. The heating bonds the fluoropolymer tapes preventing the wires from expanding to the relaxed diameter of the wound coils. It is believed that this method of achieving the desired final lead outside diameter reduces the required strain and stress seen by the wire during use and can improve fatigue resistance and lead robustness.

Filars are considered herein to be individual wires or filaments (e.g., individual conductors) within the helical windings of lead conductors that make up the lead body. Each of the first and second length segments of the folded conductor are considered to be individual filars. Typically, the filars of the first and second length segments of an individual folded conductor will be placed adjacent to each other in the multi-filar helically wound structure of the lead body.

The two free ends of the first and second length segments (opposite the bent end) will typically both be connected to the same contact on the electrical connector at the proximal end of the lead. While generally the two first and second length segments will be of approximately equal length, this is not a requirement.

While it is preferred that the bent end region of the folded conductor is uninsulated and configured to serve as an electrode, in another embodiment, the uninsulated portion of the folded conductor is located away from the bent end where the conductor remains insulated. In yet another embodiment, there may be multiple uninsulated portions along either or both of the first and second length segments of the folded conductor which serve as electrodes. The length of uninsulated portions may be varied, as may be the location of uninsulated portions along the lead. Additionally, the current density of the delivered energy may be modified by using unequal lengths of insulation on the first and second length segments of an individual conductor. This results in unequal lengths of the uninsulated first and second length portions (the electrode portions) as well, resulting in a different current density from what would be expected if the lengths were equal.

In another embodiment, the electrode region of the conductors (stripped of the outer, thicker insulation), may then be provided with a very thin, tough insulation, using the previously described substantially impermeable ePTFE/FEP insulating tape. An additional conductor, in the form of a noble metal wire (e.g., platinum iridium) may then be heated and tightly wound around the stripped and thinly insulated conductors to provide an electrode that is remarkably corrosion resistant.

The bent end of the folded conductor may be followed distally by another component such as a filament that takes the place of the folded conductor in the multi-filar helical winding of other conductors extending distally along the lead body. The filament is preferably non-conductive and is attached to the bent end of the folded conductor, serving as a means of securing the bent wire end to the lead and preventing it from rising significantly above the adjacent surface of the lead. The filament can be secured with a loop or a knot, preferably with a knot that constrains the bent end of the conductor to prevent cyclic deformation of the bend during flexing of the lead and the potential for subsequent mechanical failure. One such knot is a looped knot known as a cableman's hitch (also known as a cow hitch); this can also be tied as a multiple cableman's hitch. This filament preferably extends to the distal end of the multi-filar winding. The use of a filament having an outside diameter similar to the outside diameter of the insulated conductor allows for the possibility of maintaining isodiametricity and substantially the same filar spacing. Alternatively, a smaller diameter filament allows for decreased filar spacing (i.e., a finer pitch), thereby potentially aiding in flexibility and improving electrode surface area for the distal electrodes and minimizing the size of the attachment knot at the bend. More preferably, the non-conductive filament is also folded in half, also resulting in a bent end that passes through the bent end of the folded conductor with first and second length segments of the folded filament extending distally in the multi-filar winding. A preferred material for the filament is a fluoropolymer.

Alternatively, the bent end of the folded conductor may be secured to the lead body using other means such as adhesives or short ties. An example of an adhesive is FEP which may be applied by first filling the bent end area with an FEP powder and subsequently wrapping over the area with an FEP tape then heating the area above the melt point of the FEP. This may also increase insulative characteristics and serve as a seal against infiltration of fluids in that region of the lead. Similarly, films or tapes may be used to secure the bent end of a folded conductor to the lead body. In this embodiment, distally wound helical fibers can be applied on top of the securing film or tape, without significantly increasing the lead body profile.

In an alternative embodiment, the uninsulated electrode conductor portions may be provided with a tubular covering of a porous polymeric material, wettable by body fluids to allow for charge conduction. This tubular covering may optionally be connected to the end of the tubular insulation that covers the insulated portion of the conductor.

The electrode portions of the lead are preferably provided with a covering of a conductive porous polymeric material such as porous expanded PTFE, optionally containing a conductive material such as carbon within at least a portion of the void spaces of the porous expanded PTFE. The use of such a material provides a large electrically conductive microscopic surface area to the adjacent tissue. Pore size is typically selected to limit or entirely preclude tissue attachment. Optionally, an additional covering of porous ePTFE of a smaller pore size may cover another layer or layers of a porous ePTFE having a larger pore size if it is desired to limit tissue attachment while providing a more porous underlying covering. These porous materials may be beneficially treated with a wetting agent such as polyvinyl alcohol (PVA) to enable the underlying electrode to promptly support and enhance conduction by wetting out with body fluids upon implantation.

In another embodiment, the porous ePTFE, filled with conductive material such as carbon, may be densified creating a substantially non-porous and conductive surface over the electrode portions precluding the need for the film to rapidly wet out.

In another embodiment: various conductive polymers can be used in the electrode regions.

For improved robustness of the conductive ePTFE film over the electrode portions of the lead body, a finer pitch film angle and an opposite helical lay from the conductors is desired. Film angle may be reduced to increase tensile strength or to increase radial strength. The film angle may also be adapted to affect elongation. In addition other methods for improving robustness include using thinner, stronger conductive film, applying more layers of the conductive film, applying or adhering a reinforcing member along the conductive film region, for example a longitudinal strip or helical wrap of a metal wire or polymer filament, fiber or tape, for example a substantially impermeable ePTFE/FEP insulating tape. Alternatively a preformed, strength-adding web or braiding of a polymer or metal, in tubular form, may be applied over the conductive film electrode and subsequently attached or reduced in inner diameter to be affixed to the electrode region. A strengthening member, including one which is impermeable, may also be added over or adhered to substantially all of the conductive film covered electrode and subsequently perforated to allow conduction through said perforations. Such perforations may be formed using a laser suitable for perforating only the outer strengthening layer and not the conductive film below. An example of a puncturable strengthening member is the substantially impermeable ePTFE/FEP insulating tape. A radiopaque or echogenic marker may also be incorporated into or with a strengthening member.

Each of the electrodes along the length of the lead proximal of the tip electrode (i.e., the pacing electrode) is provided with a circumferential (annular) gasket ring or seal component at each end of the electrode. Alternatively, the seal material may be provided over much or even all of the entire length of the non-electrode portions of the lead, and may also be provided under the conductors along nearly the entire length of the lead. The preferred seal material is an elastomeric material and is intended to prevent body fluids from penetrating into the insulated portions (i.e., non-electrode portions) of the lead while the adjacent electrode portions are, via the covering of the porous and/or electrically conductive film, in direct electrical contact with body fluids. Preferred elastomeric materials include thermoplastics and fluoroelastomers. Particularly preferred is a thermoplastic fluoroelastomer copolymer of tetrafluoroethylene/perfluoromethylvinylether (TFE/PMVE) as taught in U.S. Pat. No. 7,049,380 and published US Patent application US20060198866, both to Chang et al. These materials can also be used for their adhesive properties.

Preferred conductor insulating materials are fluoropolymer films that offer excellent insulation properties, good biocompatibility and minimal tissue attachment. As noted above, a substantially impermeable ePTFE/FEP insulating tape is particularly preferred. In the interest of the lead having a minimal diameter, these materials may be effectively used in very thin forms. Thicker versions or additional layers of these same materials may be used if it is desired to create a lead with increased insulation properties and/or mechanical properties such as increased tensile strength, crush resistance, and/or improved abrasion resistance. A porous ePTFE tape, made as taught by U.S. Pat. No. 5,476,589 to Bacino, and provided with a coating of FEP as taught by U.S. Pat. No. 6,159,565 to Campbell et al., may also be added to portions of the outside of the substantially impermeable ePTFE/FEP insulation if adhesion of other materials to insulated conductors or outer lead body is desired (e.g., materials such as silicone or a fluoroelastomer copolymer).

The materials comprising the lead may optionally be heat set to form a curve or bend at the distal end during manufacturing. The helical conductor construction provides torqueability that allows steerability of a curved distal end of the lead reducing the need to exchange curved and straight stylets during implant. Additionally, the curved distal end can reduce pressure on tissue, lowering the risk of tissue perforation. The curved distal end can also improve the ability to fixate the lead tip, for example more septally in the right ventricle, which may be clinically preferred.

All or part of the outer surface of the insulated portions of the lead may be beneficially provided with a coating of the previously described thermoplastic fluoroelastomer copolymer TFE/PMVE loaded with an elutable therapeutic agent as taught in published US Patent application US20060198866 to Chang et al. Therapeutic agents contemplated include, but are not limited to, antithrombotic agents, anticoagulants, antiplatelet agents, thrombolytics, antiproliferatives, anti-inflammatory, hyperplasia and restenosis inhibitors, smooth muscle cell inhibitors, antibiotics, antimicrobials, analgesics, anesthetics, growth factors, growth factor inhibitors, cell adhesion inhibitors, cell adhesion promoters and drugs that may enhance neointimal formation such as the growth of endothelial cells. In one embodiment, said agent is an anti-inflammatory agent. In another embodiment, said anti-inflammatory is a steroid such as dexamethasone sodium phosphate. In another embodiment, the therapeutic agent may include heparin.

U.S. Pat. No. 5,874,165 to Drumheller describes attaching various therapeutic agents to PTFE substrates.

These coatings may also be applied directly to the fixation helix. Additionally, the fluoroelastomer copolymer TFE/PMVE or other polymeric coatings, with or without therapeutic agents, may be used on the helix to vary the conductive surface to control current density and impedance. This may include insulative coatings that partially cover the helix, thin coatings that cover all or most of the helix but still allow a desired conductivity, or coatings filled with conductive material such as carbon or metal particles. Additionally, a fluoropolymer coating containing carbon for conductivity has a lower thermal conductivity than a bare metal helix, sensing ring or defibrillation electrode. Lower thermal conductivity can increase MRI compatibility by reducing tissue damage due to heating of the helix or other electrodes during exposure to fields associated with magnetic resonance imaging.

In an effort to provide optimal mechanical and electrical properties in a lead, MP35N DFT wire is typically used as the conductor of choice for the defibrillation and pacing/sensing circuits. Wire made from this alloy (mainly Ni, Co, Cr and Mo) is biocompatible and has excellent strength and fatigue resistance for long-term use and survivability in an implantable lead. This wire also contains a silver core component known as "drawn filled tube" or DFT. This silver core typically ranges from 25-41% in filar cross-sectional area and provides a low electrical impedance or resistance to deliver current with minimal energy loss; 28% silver has produced good results. Fort Wayne Metals (Fort Wayne Ind.) sells a fatigue-resistant version of this wire (either as solid wire or multi-stranded wire) designated as 35NLT. Given the transition metals found within 35NLT, the surface of this wire may be prone to oxidation when used as an anode (receiving current) in a circuit. This oxidation may lead to significant pitting and/or corrosion of the wire depending on the amount of current used over a period of time. To address this issue, one or more noble metals may be useful as an outer layering on the wire (applied, for example by physical vapor deposition (PVD)) or alternatively as the entire wire. Noble metals such as tantalum, platinum, palladium and titanium and their alloys are less susceptible to oxidation or corrosion when used as either the outer surface of a wire delivering current or as the entire wire. In another embodiment, a noble metal wire, preferably platinum-iridium, may be coiled over a wire or multi-stranded wire to provide corrosion-resistance to the base wire. The diameter of the noble wire is preferably sized to be similar to the insulation thickness on the conductor wire to provide a relatively consistent diameter from the conductor portion to the electrode portion. This embodiment may be combined with insulation material between or beneath the noble wire to further improve corrosion-resistance.

In cardiac applications, the electrical connector located at the proximal end of the lead is preferably an "IS-4" or "DF-4" type that is a single male connector having multiple contacts for connecting the lead conductors to a power or sensing and control source that is usually implanted (sometimes referred to as a "generator"). One IS-4 or DF-4 connector embodiment includes an inner tubular component featuring slots or channels through which some of the lead conductor ends are passed. Contact rings made of a conductive material (e.g., stainless steel, MP35N, titanium, platinum alloy or other corrosion resistant materials) alternating with insulating rings, are co-axially fitted over the tubular member and conductor ends, with the conductor ends electrically connected to the inner surface of the contact rings by means such as an interference fit and/or resistive welding.

In another embodiment, the contact rings include axially-oriented apertures beneath their exterior surface that allow insulated lead conductors to pass through the contact rings and connect to a more proximal contact ring These rings may then be over-molded with an insulative material, such as polyurethane or silicone. Another embodiment of the connector includes contact rings having preferably integral legs bent inwardly toward an insulating inner tube centered within the connector. The inner tube is preferably threaded on at least the end portion of more preferably entirely. Both the inner tube and the contact legs pass through adjacent contacts to the distal end of connector. Each contact leg is spaced axially and radially from the other contact legs. The spaced-apart contact legs are then over-molded with preferably a biocompatible polyurethane or silicone. The conductors are connected to the distal end of each appropriate contact leg via laser-weld, crimping, or similar attachment means which may also include a sleeve component. The distal end of the legs may be made larger in area or thickness than the proximal portion of the legs to make termination to the conductor easier. One advantage to this design is that all conductors can be terminated in the connector at one region of the connector (preferably the distal region) rather than having to be terminated at each contact ring. These connections are then over-molded within a strain relief. The strain relief may optionally include a component to guide the conductors to the connection point and ensure proper spacing and orientation for proper isolation and mechanical robustness. An end cap is threaded onto the proximal end of the inner tube and seats inside the most proximal contact capturing the pin connected to the pacing coil allowing it to rotate for fixation of the active tip located at the opposite end of the lead.

Alternatively, other connectors can be used including "IS-1" or "DF-1" connectors.

BRIEF DESCRIPTION OF THE DRAWINGS

FIG. 3 is a side perspective view of a typical described lead showing each of the uninsulated bare wire electrodes having bent ends secured by non-conductive filaments, excluding outer coverings.

FIG. 3C shows a top view of the knot, filament and bent electrode end of FIG. 3B with the addition of a polymer tube insulating sleeve.

FIG. 13B also describes the appearance of a bioabsorbable flange as it would appear prior to and immediately after implantation and prior to subsequent bioabsorption.

FIGS. 14A and 14B are respectively a perspective view and an end view of a tubular tip housing provided with a pair of longitudinally oriented slots with the material of the tip housing between the adjacent slots folded inwardly to serve as a thread guide for a helical fixation member.

FIGS. 15A and 15B are respectively a perspective view and an end view of a tubular tip housing provided with a pair of helically oriented slots with the material of the tip housing between the adjacent slots folded inwardly to serve as a thread guide for a helical fixation member.

FIGS. 16A and 16B are respectively a perspective view and an end view of a tubular tip housing provided with a pair of longitudinally oriented slots with the material of the tip housing between the adjacent slots extending beyond the length of the tip housing and folded inwardly to serve as a thread guide for a helical fixation member.

FIGS. 18A and 18B are respectively longitudinal and transverse cross sections of an electrical connector with a slotted tube.

FIGS. 19A-19E describes an alternative embodiment of the electrical connector having contact rings provided with legs that extend distally to connect with conductors from the lead body.

FIGS. 20A and 20B shows an alternative embodiment of an electrical connector wherein insulated lead body wires can pass through apertures provided in the contact rings to allow them to extend and connect to a more proximal contact ring.

FIGS. 21A and 21B are respectively a longitudinal cross section and a side view that describe an electrical connector with a channeled tube intended to allow passage of lead body wires and to allow a selected wire to connect with the appropriate contact ring; FIGS. 21C-21E are transverse cross sections taken at different contact rings of this connector.

FIGS. 22A and 22B show an inner portion of the strain relief intended to improve the lead body conductor transitions to an electrical connector.

DETAILED DESCRIPTION OF THE DRAWINGS

Figure 1:
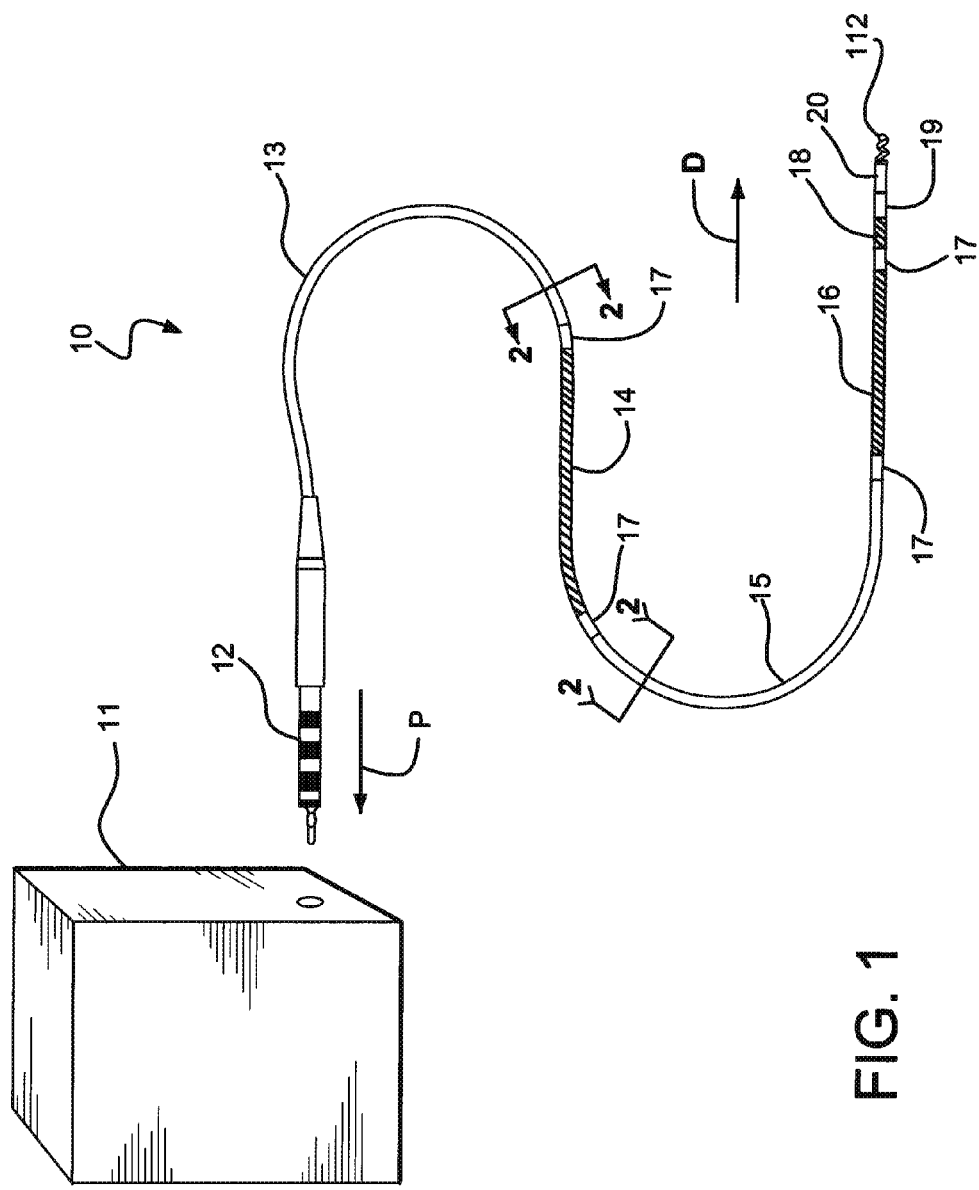
FIG. 1 is a perspective view of a typical implantable lead assembly as described herein; the embodiment depicted includes defibrillator and sensing/pacing electrodes.

FIG. 1 is a perspective view of a typical implantable lead assembly 10 as described herein, showing a proximally-located electrical connector 12 to enable lead 10 to be connected to a suitable power source or sensing and control system 11, the proximal defibrillator electrode 14, the distal defibrillator electrode 16, the sensing electrode 18 and the distal tip electrode assembly 20 attached at the distal end of lead 10 by tip connection region 19. Lead 10 also includes intervening insulated length portions 13 and 15, as well as seal components 17 located at each end of both defibrillator electrodes 14 and 16. It is apparent that any or all of the length portions shown can be made to any desired length.

Figure 2:
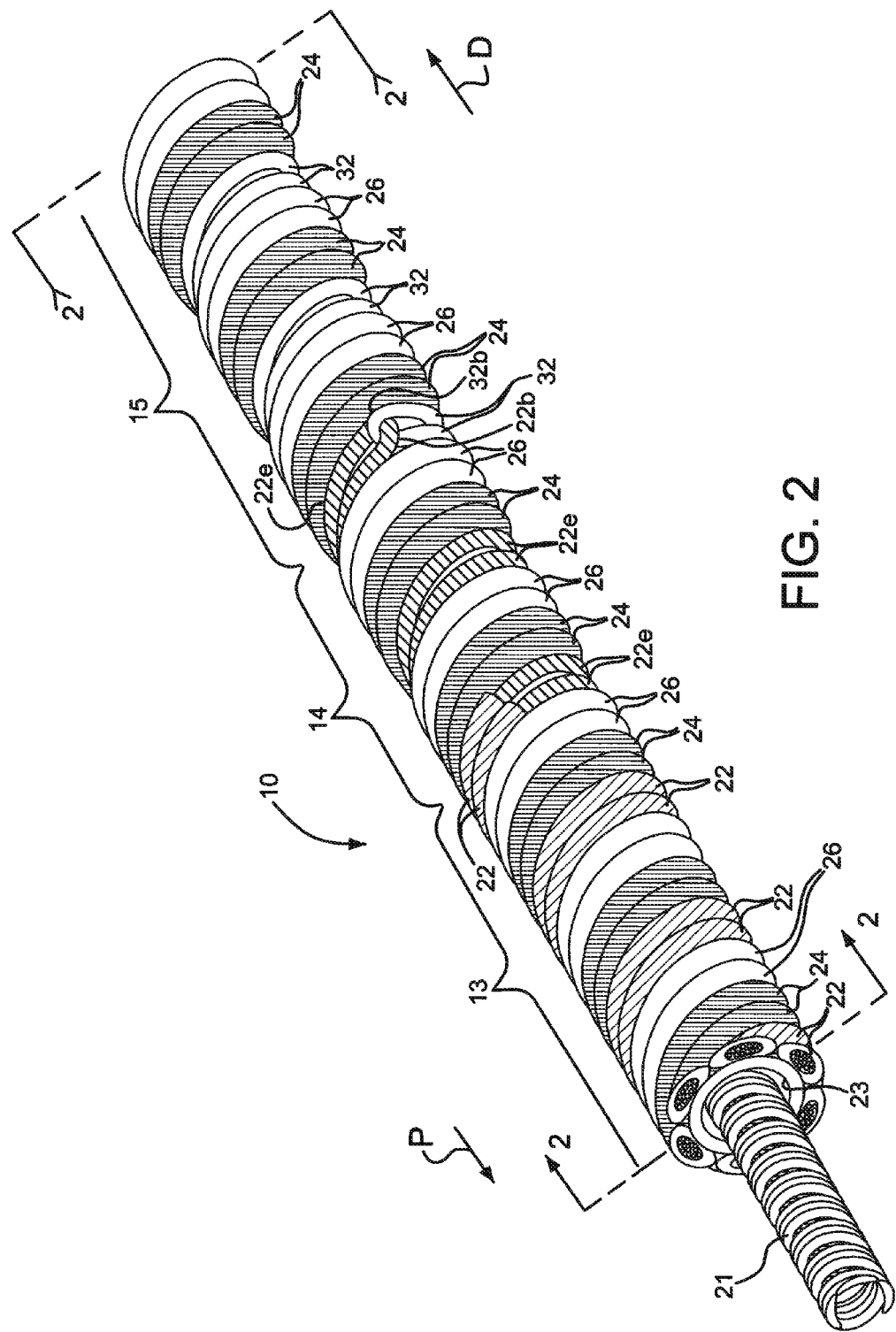
FIG. 2 is a perspective view of a portion of the length of a lead such as shown in FIG. 1, excluding outer coverings.

FIG. 2 is a perspective view of a portion of the length of a lead 10 such as shown in FIG. 1, excluding outer coverings. The portion shown in FIG. 2 is indicated by the break lines "2" shown in FIG. 1 and includes the proximal defibrillator electrode 14. Portion 13 includes three conductor "first and second length segments" 22, 24 and 26 shown in a helically wound, multi-filar arrangement that has been formed over the multi-filar winding liner 23. Helically wound pacing electrode conductor 21 is located within the lumen formed by liner 23 and extends to fixation member 112 located at the distal tip of the lead 10. Pacing electrode conductor coil 21 is provided with an outer insulative covering that is not shown here.

Figure 2A:
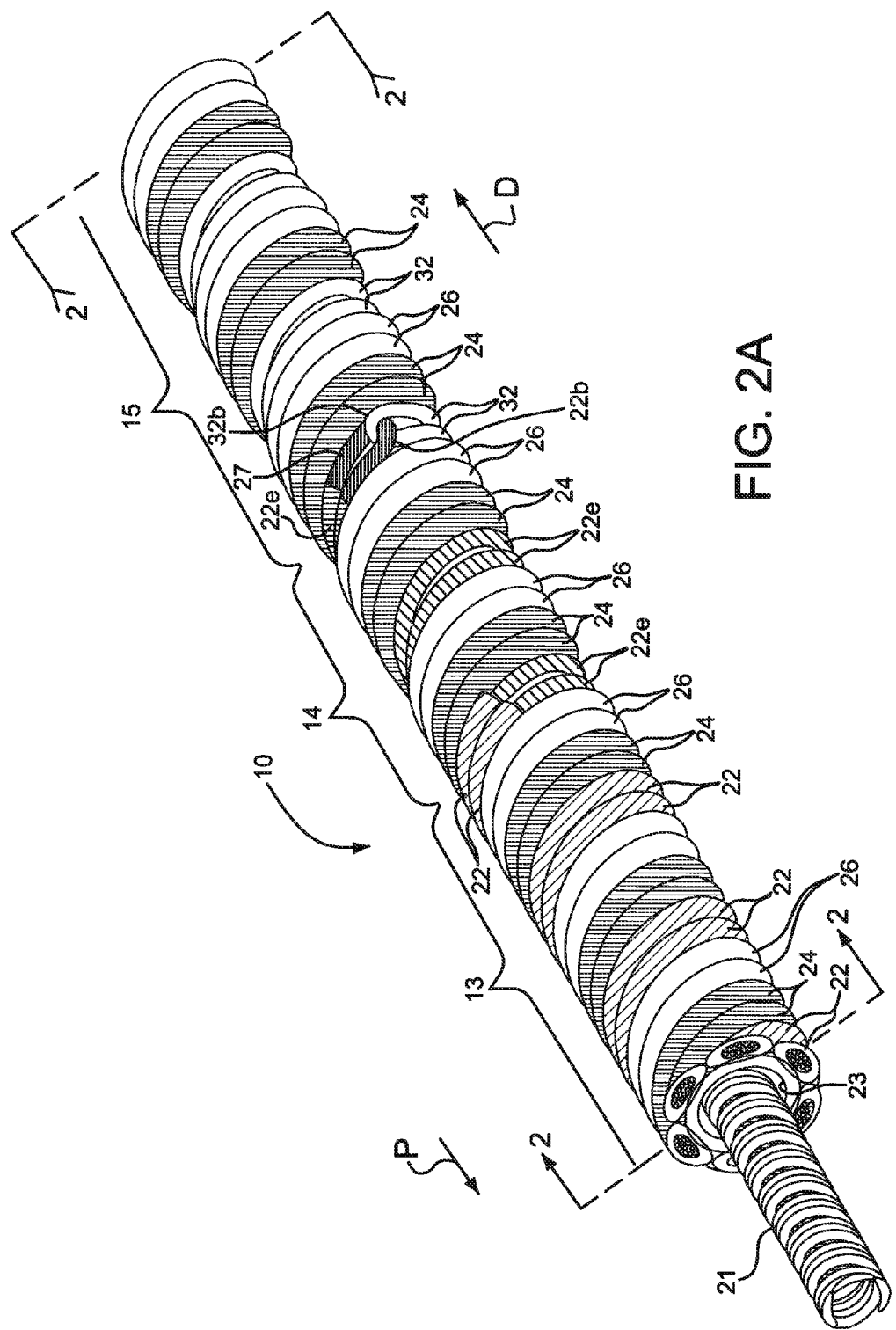
FIG. 2A is a perspective view of a portion of the length of a lead similar to FIG. 2 but showing insulation over the bent end region of the conductive wire.

FIG. 2A is a perspective view of a portion of the length of a lead similar to FIG. 2 but showing insulation 27 over the bent end 22b of the conductive wire 22e. It is apparent that insulation may be optionally used over any or all of bent ends 22b, 24b and 26b. Pacing electrode conductor coil 21 is provided with an outer insulative covering that is not shown here. The covering over pacing electrode coil 21 is preferably formed by helically-wrapping the coil at least once with the substantially impermeable ePTFE/FEP insulating tape described previously, with the FEP coated side facing against the surface of coil 21. Alternatively, the covering can be formed by extrusion or placing the coil in an insulative tubular member. A small amount of clearance (e.g., about 0.05 mm) is provided between the outer covering of pacing coil 21 and the inner lumen of liner 23 in order that coil 21 may be rotated to drive the fixation member 112 into or withdraw it from the contacted tissue.

The conductor first and second length segments 22, 24 and 26 are preferably multi-stranded wires that add to the flexibility and flex life of the lead. They are provided with a thin, strong, high dielectric strength insulation covering that is biocompatible. A preferred insulation for use around these stranded wire conductors is provided by tape-wrapping with the previously described substantially impermeable ePTFE/FEP insulating tape.

Each of the three conductive first and second length segments 22, 24 and 26 constitutes a distinct voltage conductor for three different electrodes, respectively the proximal defibrillation electrode 14 (shown in FIG. 2), the sensing electrode 18 and the distal defibrillation electrode 16 (electrodes 16 and 18 not shown in FIG. 2). It is apparent that the sequence of the arrangement of conductors and electrodes can be as desired, just as it is apparent that any desired number of conductors and electrodes can be chosen. Each of these conductor first and second length segments 22, 24 and 26 are formed from a length of a single conductor that has been folded approximately in half as will be further described.

Where insulated segment 13 transitions to electrode 14, it is seen that the insulation is removed from conductor first and second length segments 22 at the proximal end of electrode 14. The electrode 14 then comprises an uninsulated portion of first and second length segments 22, shown as 22e. The bare, uninsulated portion 22e of electrode 14 terminates at its distal end in a 180° bend 22b in uninsulated wire 22e, where it is seen how first and second length segments 22 are simply two halves of the same conductor 22 that has been folded in half to create 180° bend 22b.

At bend 22b, a non-conductive filament 32 has been passed through conductor bend 22b thereby creating filament bend 32b. It is apparent that filament 32 has been folded in half (i.e., bend 32b) in a manner similar to the way conductor 22 has been folded in half, with the halves of filament 32 creating filament first and second length segments 32 that continue to the distal end of lead 10 in the multi-filar winding within the winding space previously occupied by conductor first and second length segments 22 prior to its ending at conductor bend 22b. It is likewise apparent how conductor bend 22b is interlocked with filament bend 32b. Filament bend 32b and filament first and second length segments 32 thus serve to secure wire bend 22b to the surface of lead 10 (e.g., to the outer surface of winding liner 23). Distal to conductor bend 22b and filament bend 32b, non-conductive filament first and second length segments 32 also serve to replace the filar space previously occupied by conductor first and second length segments 22 proximal to conductor bend 22b. Non-conductive filament 32 is preferably of a fluoropolymer material, desirable for the lubricity of such materials and for resistance to process heating during construction of the lead. ePTFE filaments are preferred for their strength and lubricity; such filaments may be made generally as taught by U.S. Pat. No. 5,281,475 to Hollenbaugh Jr. et al. Filaments may also comprise polyetheretherketone (PEEK), fluorinated ethylene propylene (FEP), polyurethanes, etc. The use of non-conductive fluoropolymer filaments such as ePTFE is believed to contribute to the flexibility and flex life of lead 10. Filament 32 may be of a smaller diameter than conductors 22, 24 or 26 if it is desired to create an even finer pitch in the multi-filar winding for enhanced flexibility.

Alternatively, filament 32 might constitute a film or tape over which distally extending conductors might be helically wrapped.

While it is stated that the filaments should be of nonconductive materials, it would be possible (although less desirable) to use dimensionally compatible metal or metal-containing filaments to provide the space-occupying function of the filaments if they were insulated from the other conductive components and preferably provided with an outer covering of an insulating material to isolate them electrically from surrounding tissue.

The other two conductor first and second length segments 24 and 26 continue distally beyond the lead portion 15 shown in FIG. 2, remaining in the multi-filar winding along with filament first and second length segments 32 distal to conductor bend 22b.

FIG. 3 is a side perspective view of a typical described lead 10 showing each of electrodes 22e, 24e and 26e but excluding outer coverings; this figure is broken into upper and lower views, with the upper portion portraying proximal defibrillation electrode 14 and the lower view portraying distal defibrillation electrode 16 and the sensing electrode 18. The upper view shows electrode 14 in a similar fashion as the perspective of FIG. 2. It is seen how for each electrode 14, 16 and 18 (as one considers the lead from the proximal end to the distal end), the respective conductor first and second length segments 22, 26 and 24 are replaced by non-conductive filament first and second length segments 32, 36 and 34 following the ends of electrode conductor first and second length segments 22e, 26e and 24e at the respective interlocked 180° bends of the electrode conductors and non-conductive filaments. It is likewise seen how the 180° bends of the beginning of each filament are interlocked by being looped through the 180° bends that end each electrode conductor. Alternatively, it is apparent that one end of a filament may be tied around bend 22b, with the remainder of the length of the single filament (not folded and doubled) extending toward the distal end of the lead.

Figure 3A:
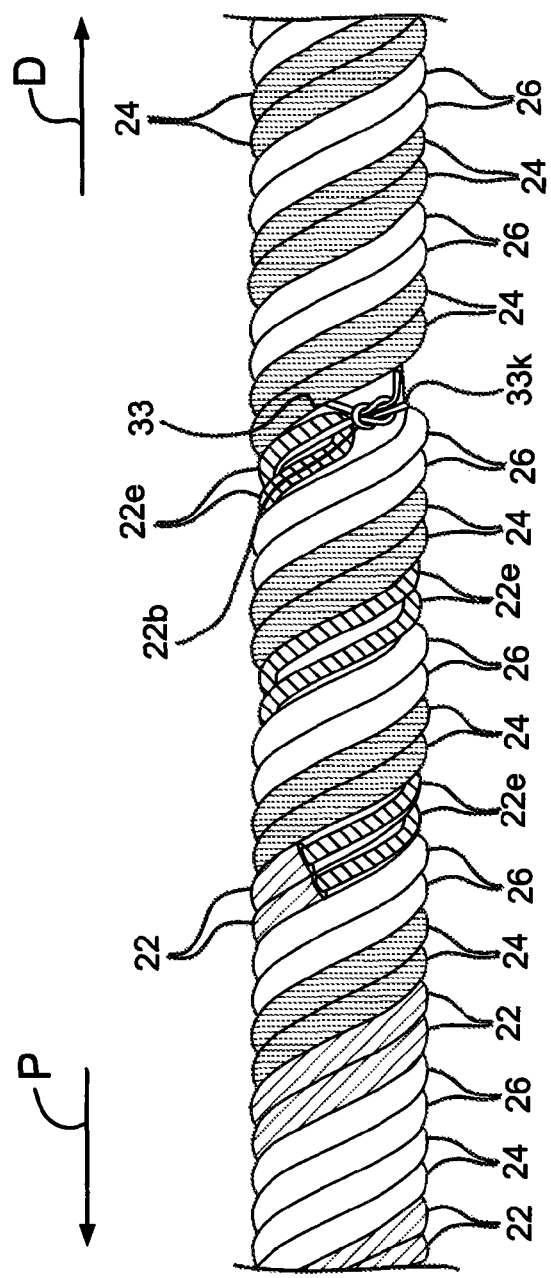
FIG. 3A is a side view of a lead showing the use of a knot with a non-conductive filament to secure the bent end of an uninsulated bare wire electrode.
Figure 3B:
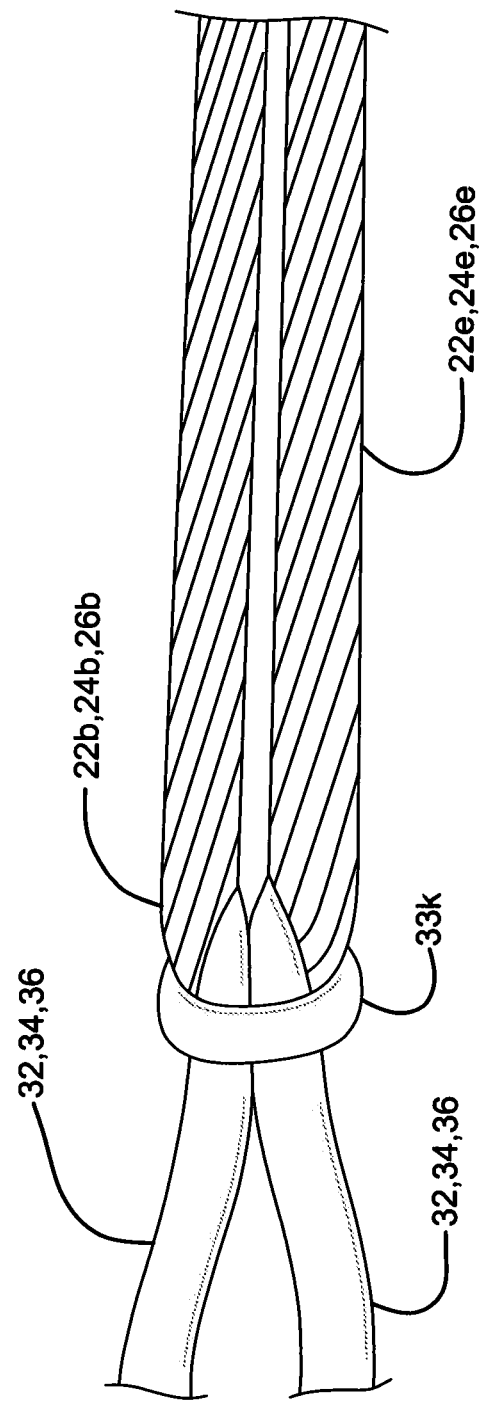
FIG. 3B is a top view showing the use of a cableman's hitch formed with a non-conductive filament to secure the bent end of an uninsulated bare wire electrode.
Figure 3D:
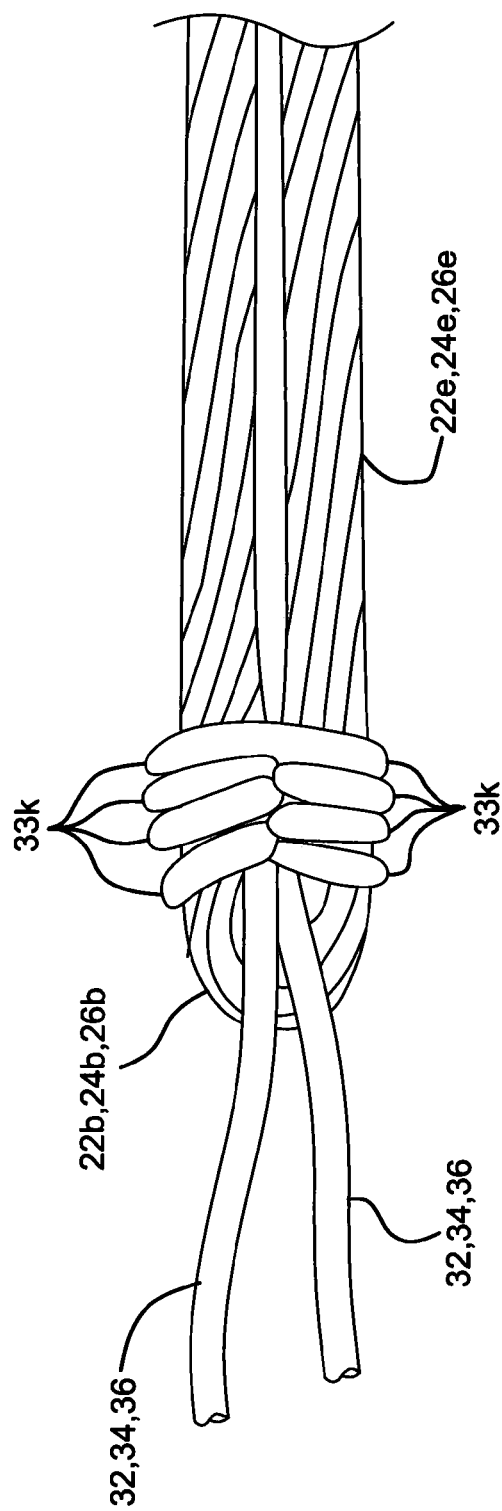
FIG. 3D shows a top view of a filament with a multiple cableman's hitch to attach the non-conductive filament to the bent end of an uninsulated bare wire electrode.

FIG. 3A is a side view of a portion of the lead 10 showing an alternative use of a filament 33 to tie down the bent end of electrode 22e. Filament 33 is wrapped once around the circumference of lead 10 (e.g., winding liner 23) and passes through the bent end of electrode 22e; the two ends of filament 33 are secured with knot 33k. FIG. 3B is a top view showing the use of a knot 33k, in this case a cableman's hitch, formed with a non-conductive filament (32, 34 or 36) to secure the bent end (22b, 24b or 26b) of an uninsulated bare wire electrode 22e, 24e or 26e. FIG. 3C shows a top view of knot 33k, filament 32, 34 or 36, and bent electrode end 22b, 24b or 26b of FIG. 3B with the addition of a polymer tube insulating sleeve 38. FIG. 3D shows a top view of a filament (32, 34 or 36) with an alternative knot 33k (e.g., a multiple cableman's hitch) attaching the non-conductive filament 32, 34 or 36 to the bent electrode end (22b, 24b or 26b).

Figure 3E:
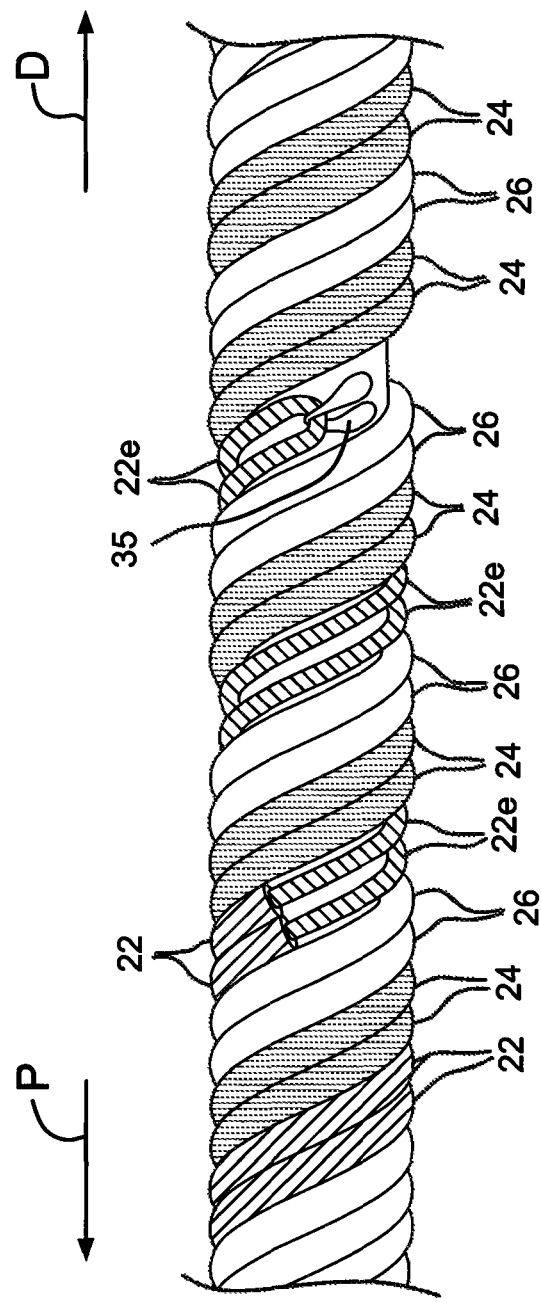
FIG. 3E is a side view of a portion of the length of a lead showing the use of adhered non-conductive tabs to secure the bent end of an uninsulated bare wire electrode.

FIG. 3E is a side view showing the bent end 22b (or 24b or 26b) of electrode 22e (or 24e or 26e) secured by securing tab 35. Such a tab may be made from various materials including the previously described substantially impermeable ePTFE/FEP insulating tape and secured by heat bonding the thermoplastic FEP coating to the underlying surface. Other adhesion methods may also be used.

Figure 3F:
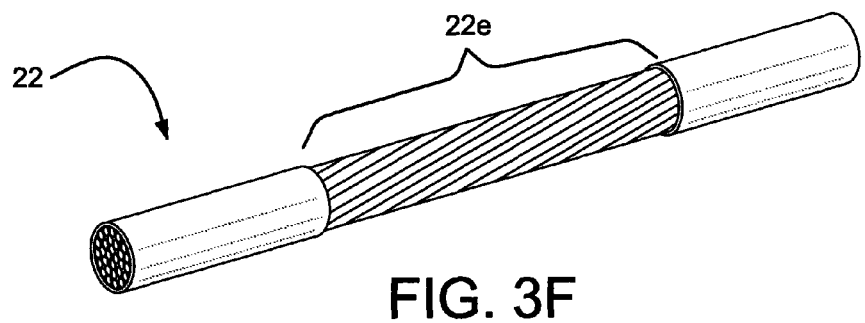
FIG. 3F is a perspective view of an uninsulated bare wire electrode located along a length of wire between two insulated portions of the same wire.
Figure 3G:
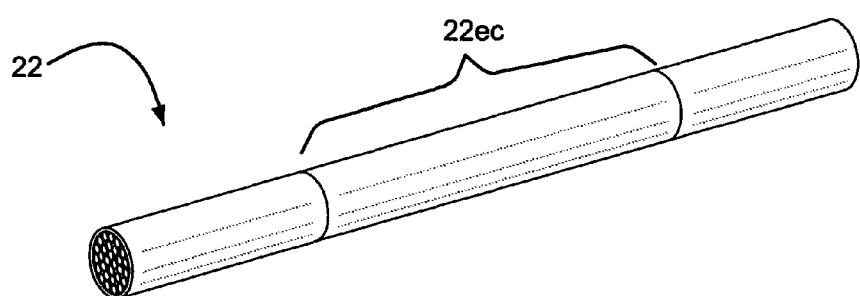
FIG. 3G is perspective view of the uninsulated bare wire electrode shown in FIG. 3F that has been provided with a covering of a porous polymeric material that allows for electrical charge conduction through the thickness of the covering.

FIG. 3F is a perspective view of a middle portion of a conductor such as conductor 22 prior to being folded in half to create parallel first and second length segments 22. It will be appreciated that the length of the exposed conductors located on either side of the bend may be equal or may be different. The uninsulated section 22e that forms electrode 14 is seen without the insulation that covers the remainder of the length of conductor 22. FIG. 3G is another perspective view that shows how the uninsulated section 22e may be provided with a covering of a porous material that allows penetration of body fluids and consequently is electrically conductive through its thickness. As noted above, a preferred porous material is porous ePTFE film; more preferred is porous ePTFE film that contains a conductive material such as carbon in a portion of the void space of the material. The figures show how the porous covering material may be used to increase the diameter of the uninsulated section 22e of FIG. 3F to match that of the adjacent insulated portions of conductor 22, thereby creating covered electrode portion 22ec shown in FIG. 3G and aiding in maintaining the preferred isodiametric character of lead 10. It is apparent that this method of increasing the diameter of an uninsulated conductor may be used whether the uninsulated portion is located between the conductor ends or alternatively located at one end of a conductor.

Figure 3H:
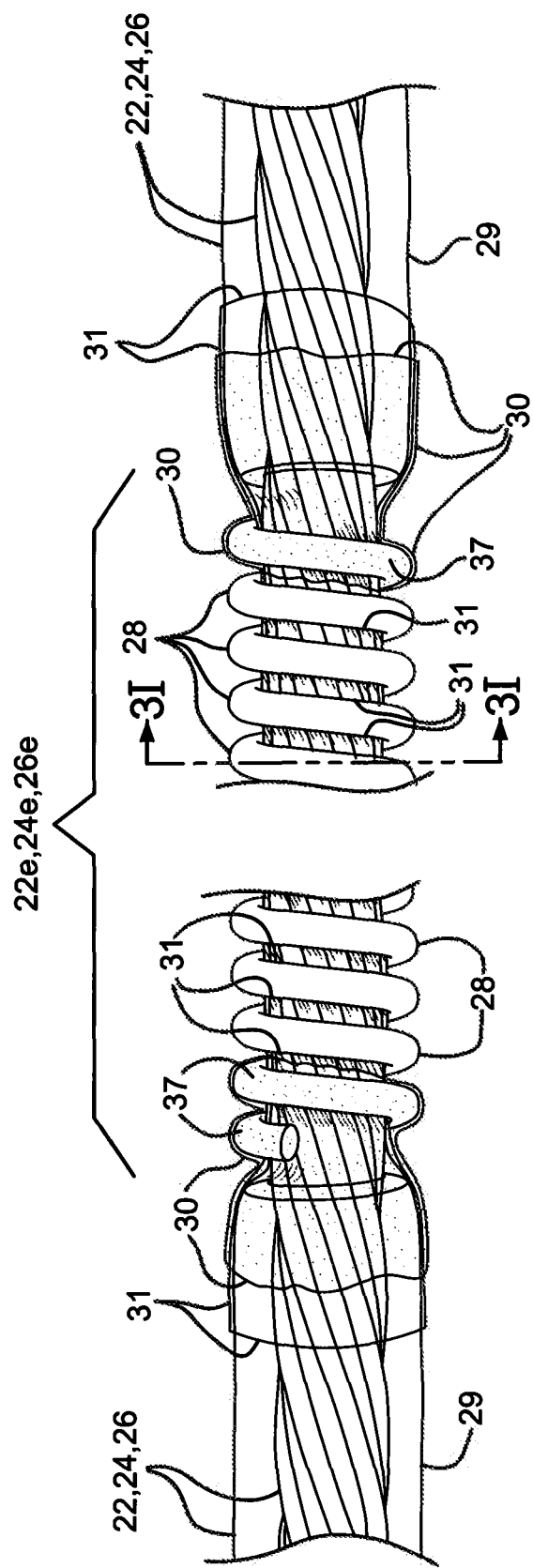
FIG. 3H is a side view of an uninsulated bare wire electrode with thin insulation and an uninsulated platinum iridium wire coil.
Figure 3I:
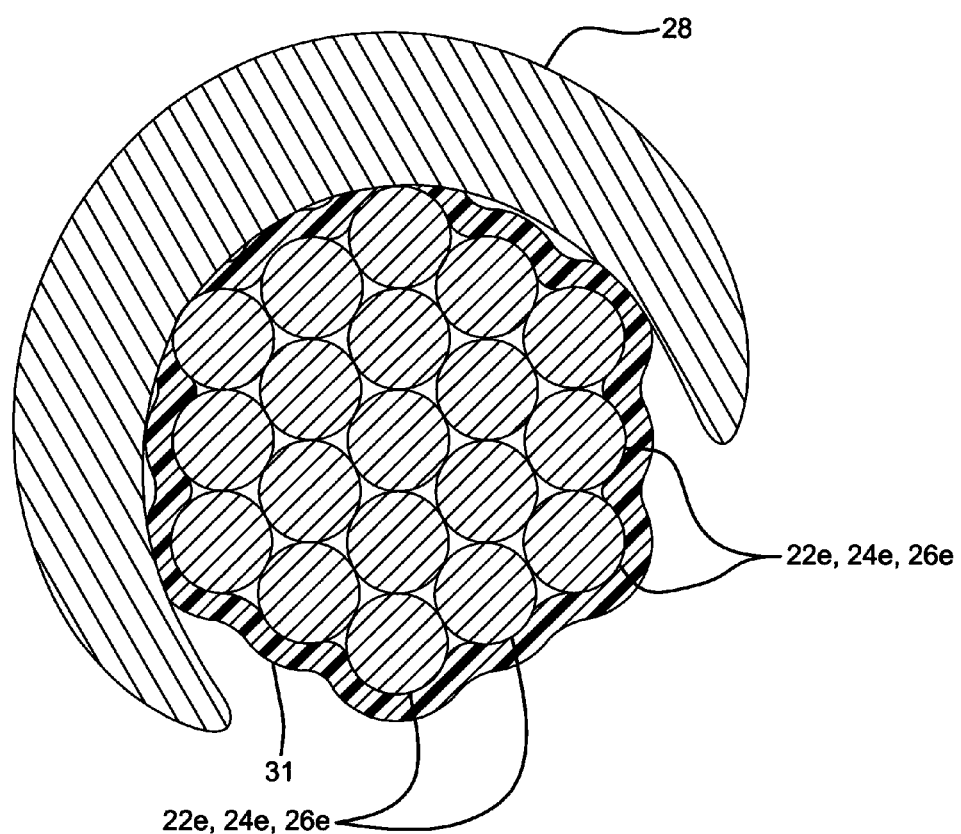
FIG. 3I is a transverse cross-section of the uninsulated bare wire electrode with thin insulation and an arc length of a platinum iridium wire coil shown in FIG. 3H.

FIG. 3H is a side view of a portion of conductor 22, 24, 26 with an electrode portion 22e, 24e, 26e. For this embodiment, the thicker insulation 29 covering conductor 22, 24, 26 is transitioned to a thinner insulation 31 such as the previously described substantially impermeable ePTFE/FEP insulating tape. Noble metal wire 28 is tightly coiled onto thinner insulation 31 with appropriate tension and heat to create electrical communication (conductivity) between noble metal wire 28 and base conductor 22, 24, 26. FIG. 3I shows a transverse cross section of noble wire 28 tightly wound around thinly insulated 31 conductors 22e, 24e or 26e. The ends 37 of the noble wire 28 are secured in place and sealed (insulated) with an elastomeric adhesive 30, preferably a fluoroelastomer adhesive such as the TFE/PMVE copolymer taught by Chang et al. as described previously. Noble wire 28 shown in FIG. 3H is of round transverse cross section, but may alternatively be a flat or shaped wire. Similarly, the thinner insulation 31 may cover the entire length of conductor 22, 24, 26 with the noble metal wire 28 coiled down the entire length of conductor 22, 24, 26 and the thicker insulation 29 over both the thinner insulation 31 and the noble metal wire 28 in the non-electrode portions. This may include a varying pitch, with the electrode portion having a tight (finer) pitch and the portions under the thicker insulation having an open (coarser) pitch.

In another embodiment, the thin insulative material 31 may be applied between the noble metal wire coils (after winding the noble metal coil 28 onto bare wire conductor 22e, 24e or 26e) leaving the outer surface of the noble wire coil 28 exposed for conductivity. This may include placing insulative material 31 over noble metal coil 28, forcing insulative material 31 between coils 28 through means such as heating and then exposing the tops of coil 28 for conductivity.

The electrodes of FIG. 3H have been shown to be highly corrosion-resistant.

Figure 3J:
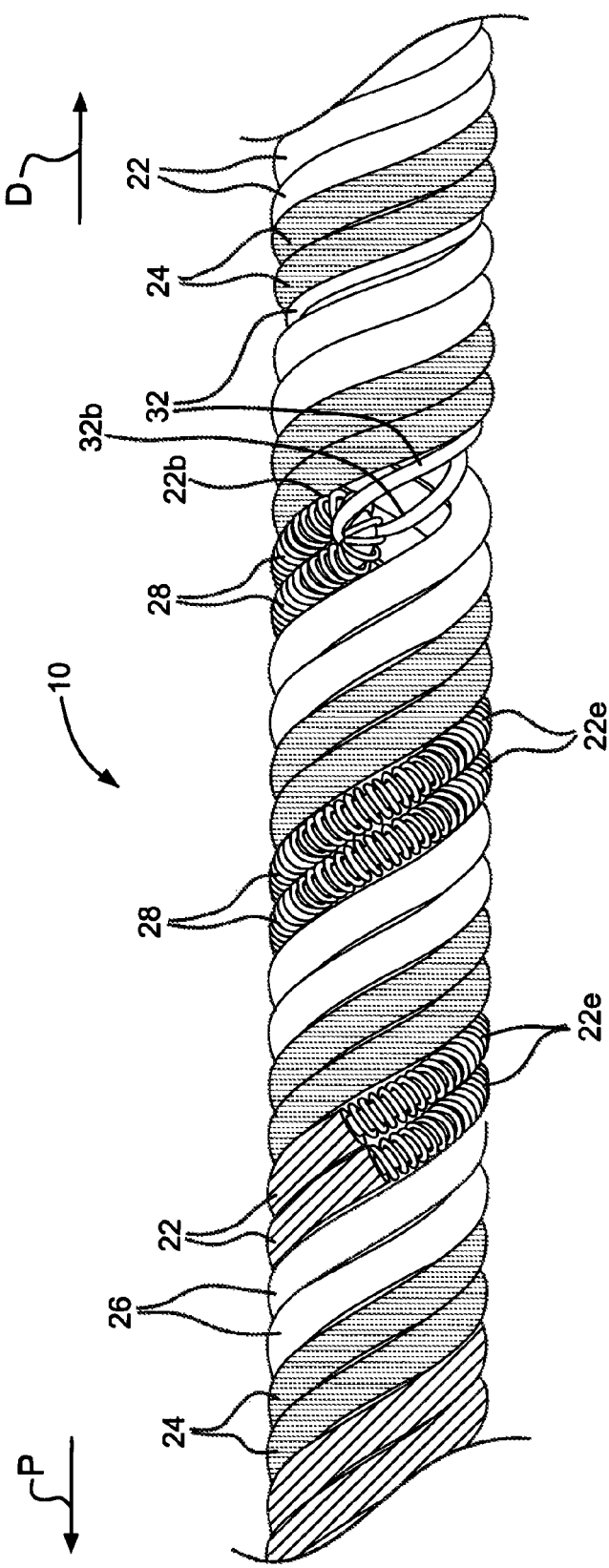
FIG. 3J is a side view of lead body with the electrode described in FIGS. 3H and 3I.

FIG. 3J is a side view of a portion of lead body 10 showing noble wire 28 coiled over thinly insulated electrode portion 22e of conductor 22.

Figure 3K:
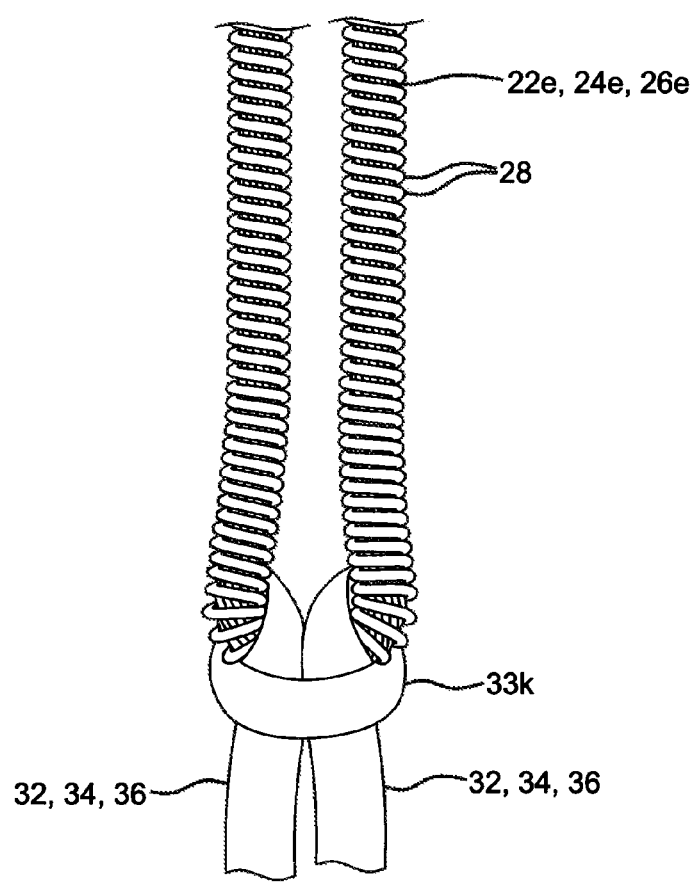
FIG. 3K is a perspective view of a standard (single) cableman's hitch tied to the end of the bent portion of the electrode described by FIGS. 3H and 3I.

FIG. 3K is a top view showing the use of a knot 33k, in this case a cableman's hitch, formed with a non-conductive filament (32, 34 or 36) to secure the bent end (22b, 24b or 26b) of a thinly insulated wire electrode 22e, 24e or 26e provided with a tightly wound noble wire coil 28.

Figure 3L:
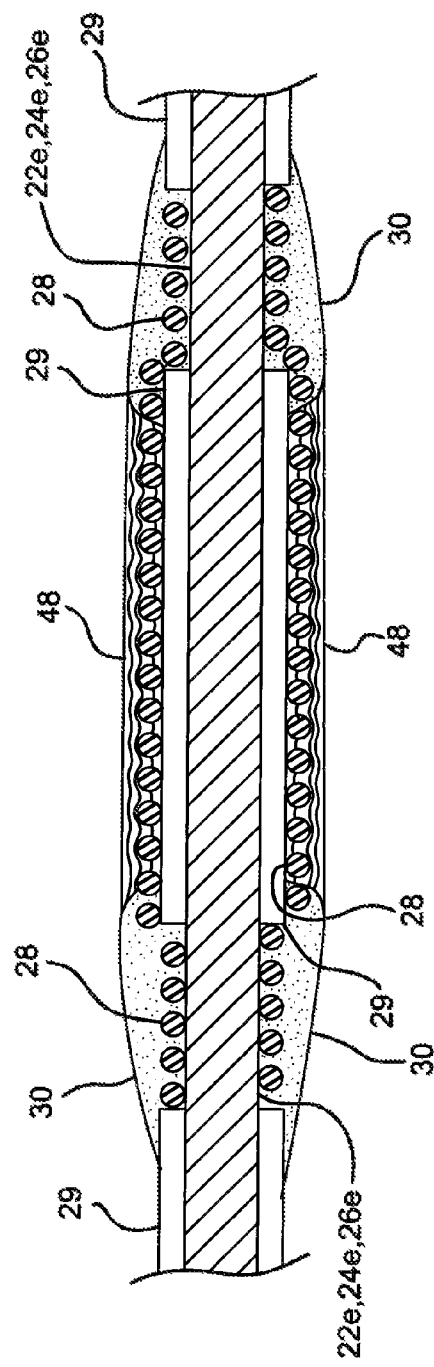
FIG. 3L is a longitudinal cross-section showing an alternative embodiment with a platinum iridium wire coil in contact with the conductor adjacent to each end of the electrode portion of conductor.

Additionally, as shown by the longitudinal cross section of FIG. 3L, the noble metal wire 28 may be coiled onto bare conductor 22e, 24e or 26e in a stripped section, then continue over a fully (e.g., thickly) insulated section 29 of conductor 22, 24 or 26 and then coil over a second stripped section 22e, 24e or 26e. These stripped sections may then be additionally covered with an insulation 30 to prevent fluid penetration. The center section, provided with a covering of a conductive polymer (e.g., carbon-loaded ePTFE film), functions as an electrode.

Figure 4:
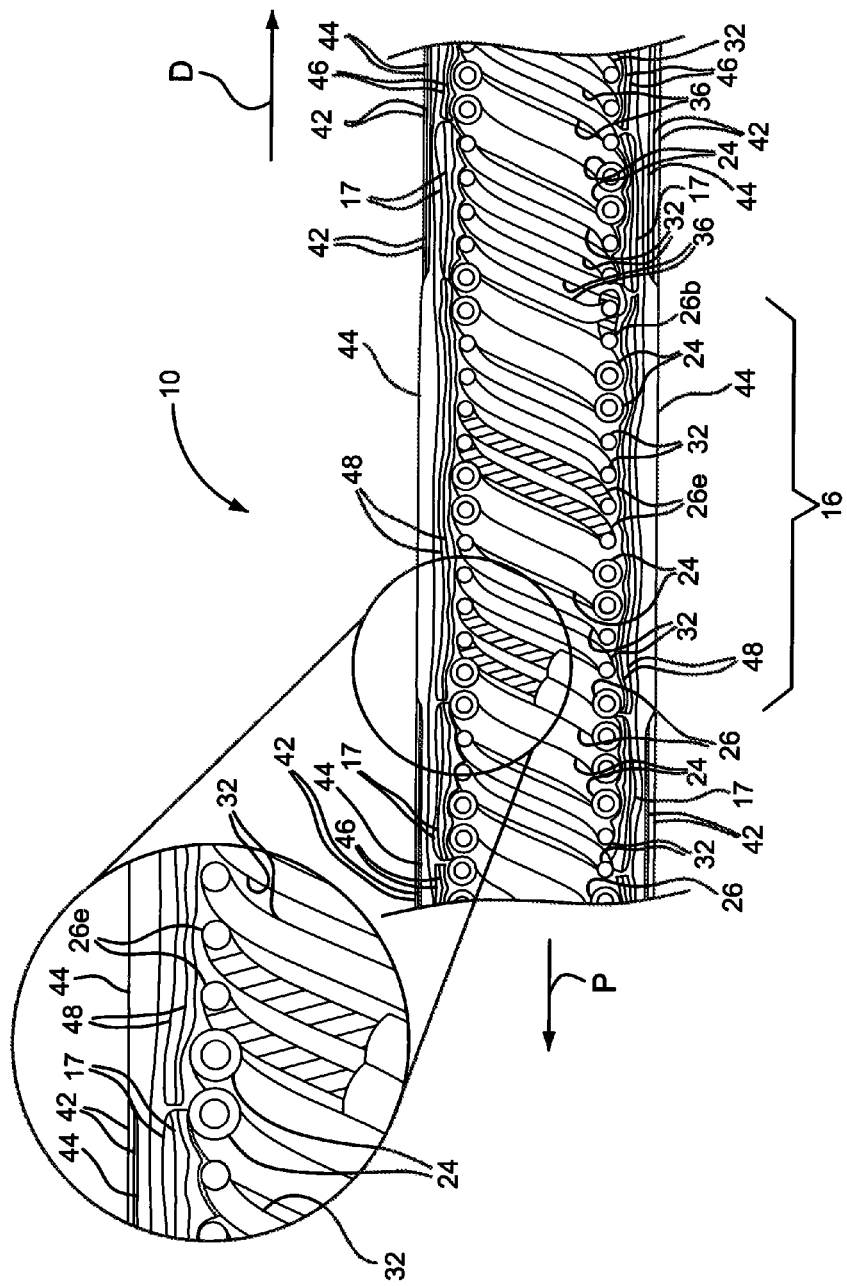
FIG. 4 is a longitudinal cross section of an uninsulated bare wire electrode (e.g., the distal defibrillator electrode) that does not include an outer platinum iridium coil showing the preferred outer coverings.

FIG. 4 is a longitudinal cross section of electrode (the distal defibrillator electrode) that describes preferred outer electrode coverings. The section shown describes distal defibrillation electrode 16 but is typical for electrodes 14, 16 and 18 with regard to outer coverings. While a specific combination of coverings is shown, it is apparent that these coverings may be applied in a variety of thicknesses, number of layers, materials, etc.

Figure 4A:
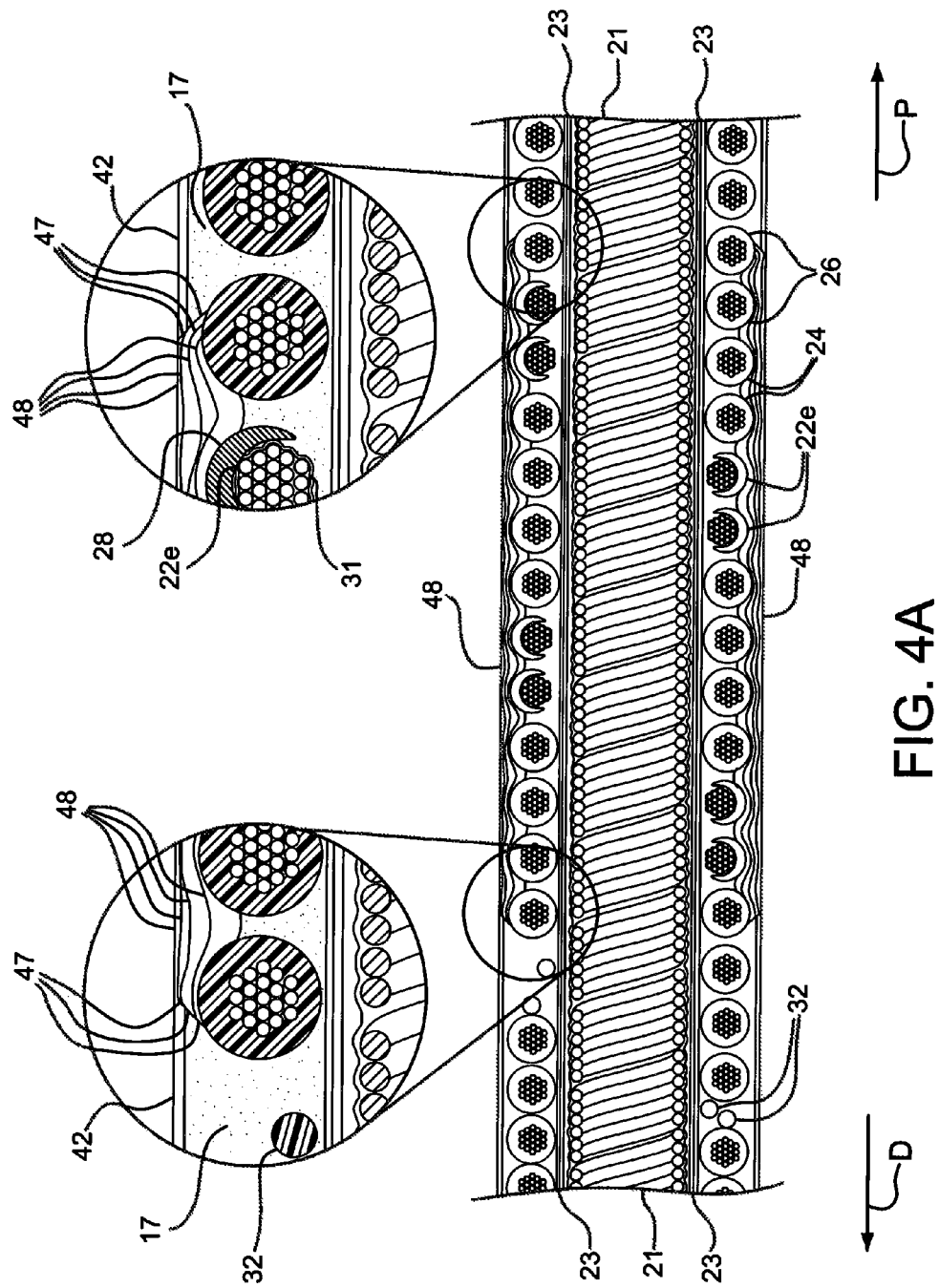
FIG. 4A is a longitudinal cross section of an uninsulated bare wire electrode (e.g., the SVC electrode) that includes an outer noble metal coil showing the preferred outer coverings including tapered film transitions.
Figure 4B:
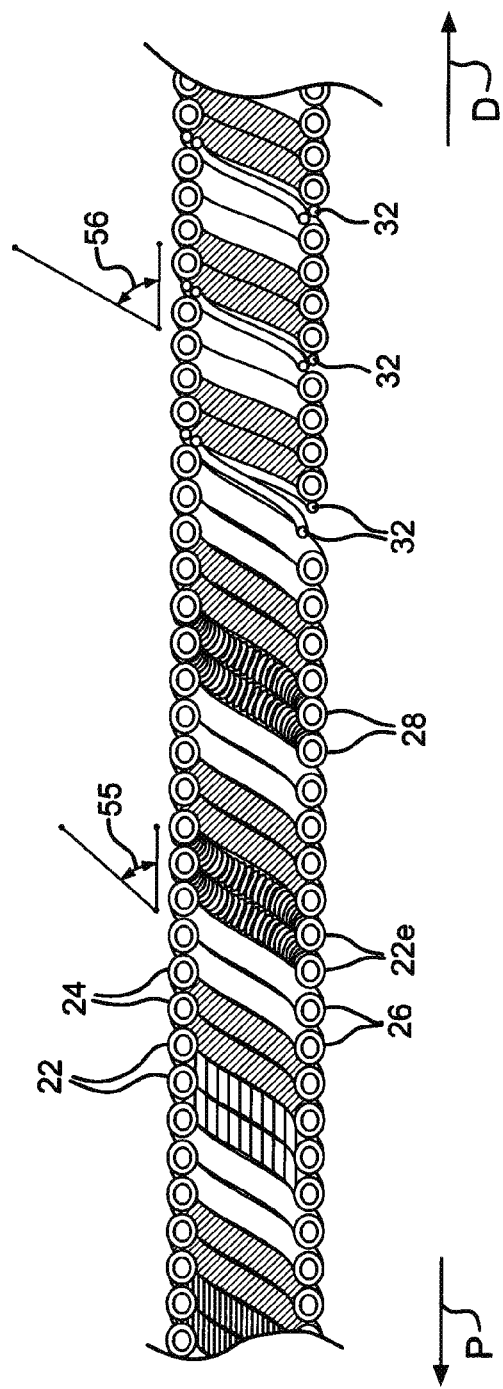
FIG. 4B is a longitudinal cross section showing pitch change of the multi-filar windings when an electrode terminates at a bent end and is replaced in the winding sequence by an uninsulated filament of diameter smaller than the electrode.

It is noted that FIGS. 4, 4A and 4B do not include pacing conductor coil 21 or inner liner 23 to allow for clarity of the description of the components shown.

Seal components 17 are provided at opposing ends of electrode 16 and are intended to prevent body fluids from making their way into the non-electrode, insulated conductor portions of the length of lead 10. Seals 17 are comprised of an elastomeric material with fluoroelastomers preferred. Particularly preferred is the previously described TFE/PMVE fluoroelastomer copolymer. These seals may also be made by circumferentially wrapping the area where it is desired to provide the seal component with a composite tape made from a film of ePTFE provided with a coating of an elastomer such as the TFE/PMVE copolymer. The circumferentially wrapped ePTFE provides strength and adds circumferential compression when heated, while the thermoplastic TFE/PMVE is allowed to flow into the underlying shape of the insulated conductors during the controlled manufacturing heating step. These composite ePTFE and fluoroelastomer tape materials are also described by Chang, et al. in U.S. Pat. No. 7,049,380 and published US Patent application US 20060198866.

The outer surface of electrode 16 is provided with a covering 48 of a porous, electrically conductive film such as carbon-loaded ePTFE film. The number of wraps (two layers are shown) will be a function of the total porosity of the covering, the conductivity of the covering and the desired thickness of the covering.

The insulated portion of the lead on either side of electrode 16 and the seal components 17 is provided with a wrapping 46 of an ePTFE film. While this film may be (for convenience) the same carbon-loaded ePTFE film covering 48 used over the electrode, alternatively, a non-conductive film may be used. In another alternative, the composite ePTFE and fluoroelastomer tape described above may also be used. Two layers of wrapping 46 are shown, but again this thickness will be determined by desired design criteria.

Following the application of the above-described coverings of length portions 13 15, and 17 of lead 10, the entire length of the lead (including the insulated portions and the electrode portions) may be provided with a wrapped covering 44 of a porous ePTFE film. One layer 44 is shown, but again this thickness will be determined by desired design criteria.

Finally, the insulated portions of the length of the lead 10 are provided with a covering 42 of the substantially impermeable ePTFE/FEP insulating tape used previously for insulating individual electrical conductors. This covering may also be applied as a helical tape-wrapping. While two layers 42 are shown, the thickness will be determined by desired design criteria.

FIG. 4A is a longitudinal cross section showing the tapered transitions 47 between the conductive film 48 (e.g., carbon-loaded ePTFE film) covering the electrode portions, and the covering 42 over the adjacent insulated portion 13, 15 or 17, preferably the previously described substantially impermeable ePTFE/FEP insulating tape. These tapered transitions 47 may extend over longer lengths than described by FIG. 4A. In one embodiment, the insulative outer body film 42 is helically overwrapped with substantially impermeable ePTFE/FEP insulating tape (not shown) slightly overlapping onto the conductive outer body film 48.

FIG. 4B is a longitudinal cross section showing pitch change (difference between angles 55 and 56) resulting from the use of filament 32 to replace conductor 22 as it terminates at bent end 22b (not shown), the filament 32 of this embodiment being of smaller diameter than insulated conductor 22. The resulting finer pitch 56 enhances flexibility in that portion of the lead. Enhanced flexibility is believed to be desirable at the distal end of the lead 10 to prevent tissue perforation at the point of tissue attachment.

Figure 5:
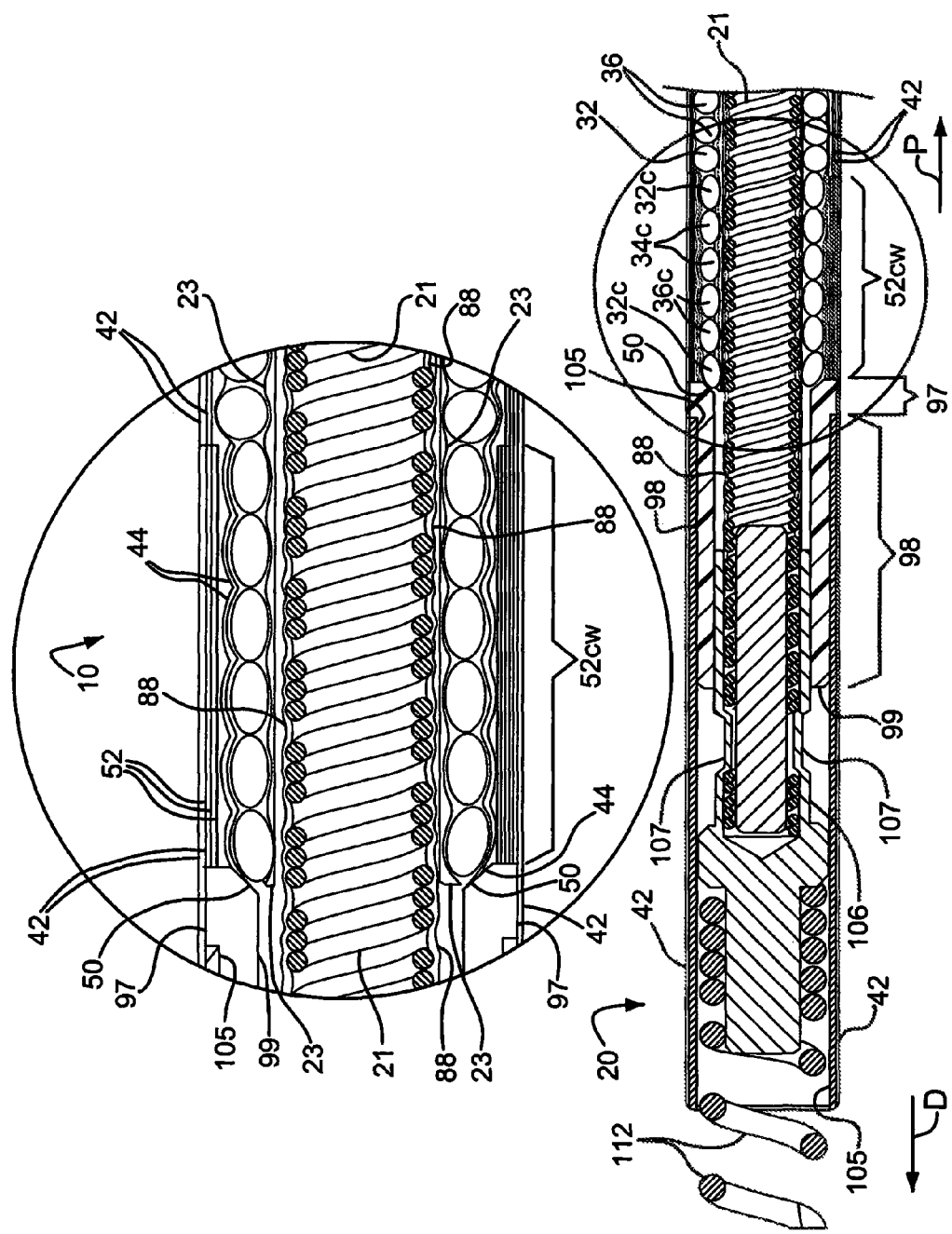
FIG. 5 is a longitudinal cross section describing the attachment of the pacing electrode (including fixation member) to the distal end of the lead.

FIG. 5 represents a side cross sectional view of the junction between the distal tip assembly 20 (further described below) and lead 10 showing one construction suitable for attaching the distal tip assembly 20 to the distal end of lead 10. Said junction comprises a bushing 99 (see also FIG. 6) which abuts against tubular tip housing 105 and the distal end of the body of lead 10. Bushing 99 includes a sleeve portion 98 that fits within tubular tip housing 105, and flange portion 97 for attaching bushing 99 to the tip housing 105. Bushing 99 is preferably made from a non-conductive material such as plastic. Preferred plastic materials are fluoropolymers such as PTFE or FEP. Sleeve portion 98 of non-conductive bushing 99 is fitted into the proximal end of tubular tip housing 105 (see below description), with flange 97 abutting the proximal end of tubular tip housing 105 and the distal end of the body of lead 10. All three components are attached by wrapping one or more layers of a thin impermeable film 42 (such as the substantially impermeable ePTFE/FEP insulating tape used previously for insulating individual electrical conductors) around the outer surface of tubular tip housing 105, flange portion 97 of bushing 99 and the distal end of the body of lead 10. Bushing 99 further comprises an internal chamfer 50 which will accommodate the distal end of insulating film layer 44 and non-conductive filaments 32, 34, 36 that are flattened (32c, 34c, 36c) due to the pressure exerted by the several layers of circumferentially wrapped insulating tape 52 in region 52cw.

Filaments 32, 34 and 36 are shown disposed over a multi-filar winding inner liner 23 which extends for the entire length of lead 10 and also underlies helically wound conductors 22, 24 and 26. Multi-filar winding liner 23 is preferably a fluoropolymer layer that provides a lubricious luminal surface beneath the helically wound conductors 22, 24 and 26 and the helically wound filaments 32, 34 and 36, and that aids the rotational capability of pacing coil 21 that resides in this luminal space. Additionally, polymeric multi-filar winding liner 23 can serve as a release agent from any mandrel used temporarily as a supporting surface for the winding of conductors 22, 24 and 26 as well as filaments 32, 34 and 36. This layer 23 may be made by winding layers of ePTFE tape (e.g., substantially impermeable ePTFE/FEP insulating tape) over a temporary construction mandrel and heat bonding them together prior to winding the conductors and filaments.

Pacing coil 21 is also preferably provided with an outer covering 88 of a polymeric material of the previously described substantially impermeable ePTFE/FEP insulating tape. Typical clearance provided between the outer covering 88 of pacing coil 21 and the luminal surface of multi-filar winding liner 23 may be, for example, about 0.02-0.06 mm.

As shown in FIG. 5, the transition from the distal end of the body of lead 10 to distal tip assembly 20 comprises several layers of film. One (or more) of the layers is the continuation of layer 44 (see FIG. 4), which comprises a porous ePTFE film that is helically wrapped on lead 10, as described above. Next, multiple layers 52 of an insulating film such as the previously described substantially impermeable ePTFE/FEP insulating tape are wrapped circumferentially around the distal end of the body of lead 10 adjacent to and immediately proximal to bushing 99. These wrapped layers 52 of tape are used to secure the distal ends of filaments 32c, 34c and 36c, and to match the diameter of the distal end of lead 10 in region 52cw to the outside diameter of tubular tip housing 105 so that lead 10 and tip housing 105 are isodiametric (each "layer" 52 may comprise multiple wrappings of tape). Said substantially impermeable insulating tape 52 is used to prevent tissue from growing into lead 10 and serves as an insulator. Layer(s) 42, continued from the body of lead 10, are helically wrapped around the distal end of the body of lead 10, flange 97 of bushing 99 and the outer surface of tubular tip housing 105. Other materials may be provided over the layers 42 if desired for other purposes such as therapeutic agent elution, as will be further described.

Figure 6:
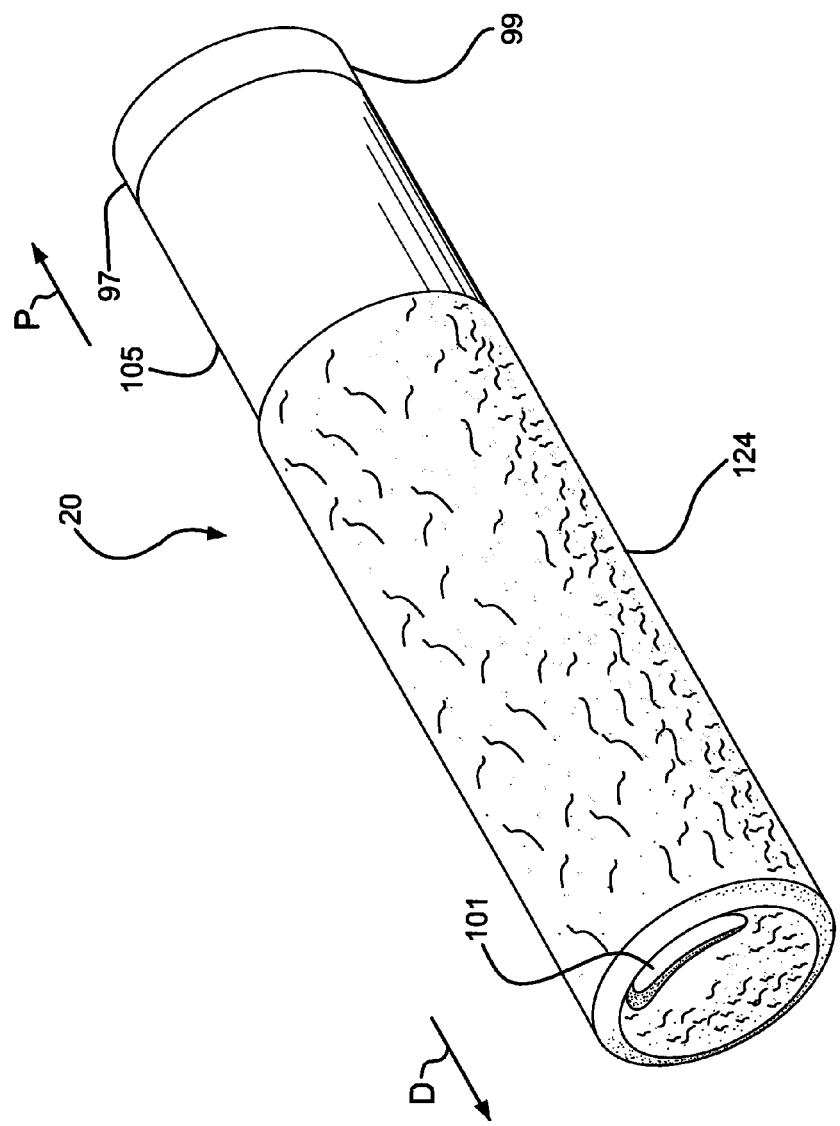
FIG. 6 is a perspective view of a distal lead tip assembly provided with a covering of a therapeutic agent eluting polymer and containing an active attachment component (e.g., helical fixation member).
Figure 7:
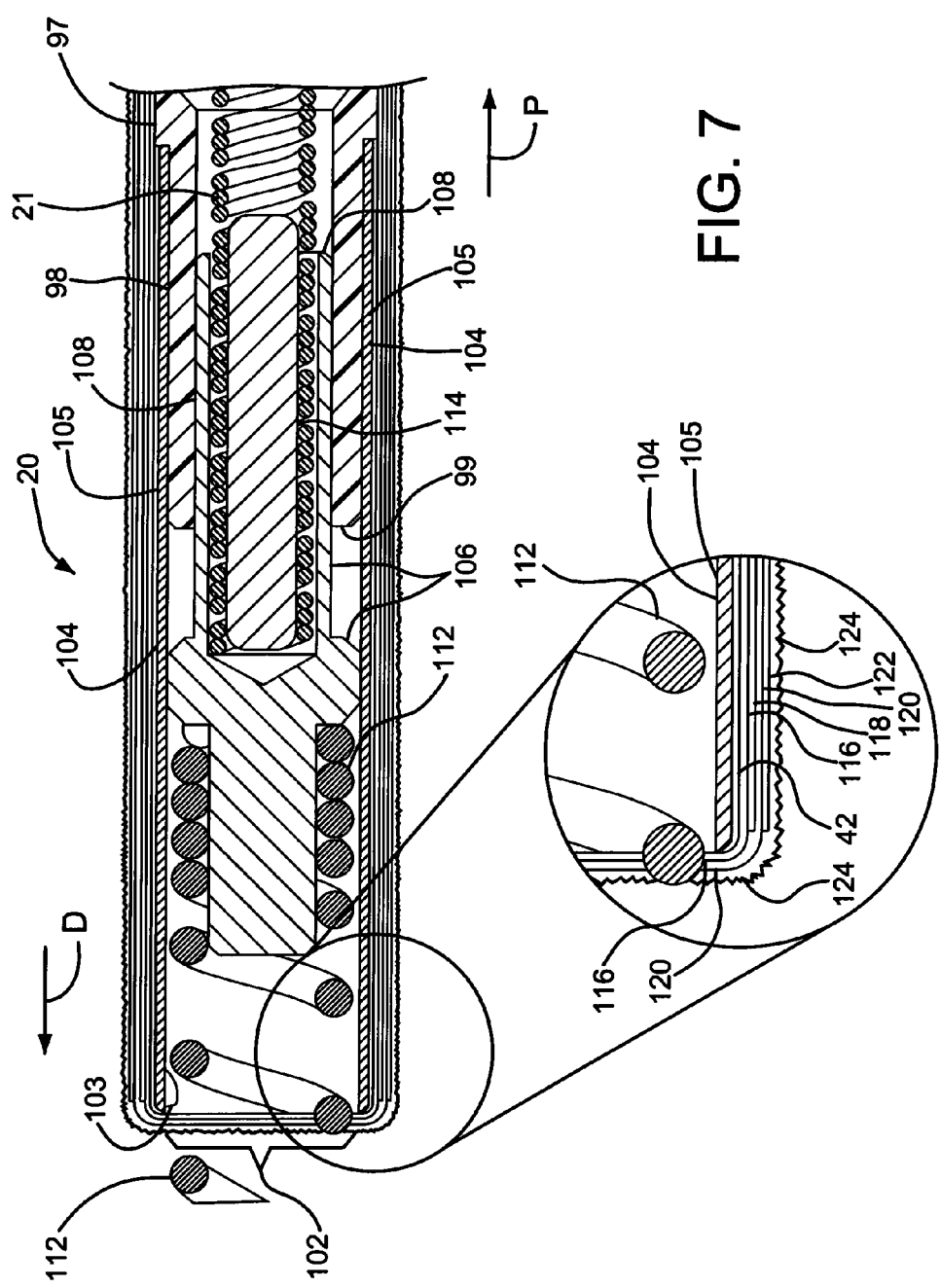
FIG. 7 is a longitudinal cross section showing the construction of one distal lead tip assembly embodiment.

FIG. 6 is a perspective view of one embodiment of the distal tip assembly 20 of lead 10 (hereinafter referred to as the "tip"). As seen in FIGS. 6 and 7, s tip 20 is constructed from a tubular tip housing 105 comprising a sidewall 104 and a substantially open end 102, a fixation member 112, and at least one layer of substantially impermeable ePTFE/FEP insulating tape covering a portion of said tip housing and at least a portion of said open end. Also shown is flange 97 of non-conductive bushing 99, as described above. Tip assembly 20 in FIG. 6 depicts a sprayed on layer of the previously described thermoplastic fluoroelastomer TFE/PMVE 124, and includes eccentric hole 101 that guides a helical fixation member 112 out of tubular tip housing 105. The TFE/PMVE coating layer may optionally contain an elutable therapeutic agent including, but are not limited to, antithrombotic agents, anticoagulants, antiplatelet agents, thrombolytics, antiproliferatives, anti-inflammatory, hyperplasia and restenosis inhibitors, smooth muscle cell inhibitors, antibiotics, antimicrobials, analgesics, anti-coagulant, anesthetics, growth factors, growth factor inhibitors, cell adhesion inhibitors, cell adhesion promoters and drugs that may enhance neointimal formation such as the growth of endothelial cells. A preferred therapeutic agent is an anti-inflammatory steroid such as dexamethasone sodium phosphate.

Tip assembly 20 is coupled to the medical lead (as described above) via non-conductive bushing 99 which abuts against said tip assembly 20 and the distal end of the body of lead 10. With bushing 99 fitted into tip housing 105 as shown and abutted against the distal end of the body of lead 10, these components are attached to the distal end of lead 10 by wrapping multiple layers of substantially impermeable ePTFE/FEP insulating tape around the outer surface of tip housing 105, bushing 99 and lead 10 as previously described.

FIG. 7 illustrates a side cross sectional view of distal tip assembly 20. The tip housing 105 is constructed from a tubular material having a substantially open end 102 and sidewall 104. Tubular tip housing 105 can be made from any durable, biocompatible material, for example PTFE, stainless steel, nitinol, or platinum. The tip housing 105 contains a post 106 which electrically couples coil 21 to a fixation member 112, which will be inserted into the tissue. Post 106 can be made from any biocompatible, durable metal, most preferably stainless steel, although other conductive materials such as platinum, titanium or gold may also be employed. In one embodiment, a region of post 106 will be in close contact with the inner wall of tip housing 105. This contact will provide proper guidance to fixation member 112 as fixation member 112 is extended or retracted. In another embodiment, post 106 comprises a sleeve portion 108. In another embodiment, coil 21 is placed into sleeve portion 108 of post 106 and held in place by spot or laser welding or crimping. In another embodiment, a crimping mandrel 114 is inserted into coil 21 and placed into sleeve 108 of said post 106 and crimped. Said crimping mandrel 114 supports said coil 21 during crimping so that said coil 21 is not collapsed during crimping. The coil 21 can be insulated such as by wrapping with a film 88 (see FIG. 5; e.g., the previously described substantially impermeable ePTFE/FEP insulating tape) to keep coil 21 tightly wound and can also serve as insulation to prevent shorting and to improve torque transmission. If said coil 21 is insulated, then the crimp 107 (see FIG. 5) will break outer covering of film 88 to allow contact between the post 106 and the coil 21.

In another embodiment, coil 21 is not insulated at the distal end so that it can easily be electrically coupled to post 106. In another embodiment of the invention coil 21 is the pacing coil of lead 10 (as described above).

FIG. 7 also illustrates a fixation member 112 intended to provide attachment to tissues. The fixation member 112 can be made from any biocompatible, durable and conductive material such as stainless steel, platinum, titanium, palladium, and their alloys. In one embodiment, said fixation member 112 is a helical fixation member. In another embodiment, said helical fixation member 112 may be rotatably extended and retracted by rotation of the coil 21. Said helical fixation member 112 can be secured to post 106 by laser or spot welding, or by crimping, or by other methods known to those skilled in the art. Post 106 will electrically couple the fixation member 112 to the coil 21 and also serve as an axial guide for fixation member 112. Guidance to helical fixation member 112 may also be provided by means such as deformation 103 formed in or attached to the distal end of the inner wall of the tubular tip housing 105; other guidance means such as a guiding pin may also be utilized.

FIG. 7 illustrates that distal tip assembly 20 may be covered by several "layers" of film. Each "layer" may comprise multiple wrappings of film. Thus the term "layer" is not limited to one wrapping, but may encompass any number of wrappings. In one embodiment, at least one layer is a layer substantially impermeable to fluids and tissue ingrowth. Said substantially impermeable layer may also provide electrical insulation. As illustrated in FIG. 7, there may be several layers of film covering the side wall 104 and the opening 102 of tubular tip housing 105. Layer 42 is a substantially impermeable layer that extends from side wall 104 of the tip housing 105 to the body of lead 10, so that said tip assembly 20 and body of lead 10 are coupled together, as described above. This layer 42 also serves to electrically insulate the tip housing. Layer 42 may be applied by helically wrapping the substantially impermeable ePTFE/FEP insulating tape, around the body of lead 10 and the tip assembly 20. In one embodiment, said layer 42 is the previously described substantially impermeable ePTFE/FEP insulating tape. In another embodiment, said distal tip assembly 20 may comprise another layer of film 116. In this embodiment, layer 116 covers at least side wall 104 and open end 102 of tip housing 105. In this embodiment, said layer 116 is "draped" over the open end 102 of tip housing 105, thus covering opening 102 (with a drum-like covering) and said side wall 104. In another embodiment, said distal tip assembly 20 comprises another layer of film 118 wrapped around side wall 104 and over layer 116. In this embodiment, film 118 may also be a substantially impermeable film. In another embodiment, said film is the previously described substantially impermeable ePTFE/FEP insulating tape. Layer 118 can serve to keep layer 116 in place and also adds another layer of electrical insulation to tip housing 105. In another embodiment, said tip assembly 20 may comprise an additional layer of film 120 which is preferably a permeable layer. Said layer can be a porous ePTFE film provided with a discontinuous (porous) coating of FEP. In this embodiment, layer 120 is "draped" over the tip assembly 20, thus covering said tip housing opening 102 (in a drum-like covering) and said side wall 104. Said porous FEP-coated ePTFE film 120 can be attached to underlying substantially impermeable tapes via the FEP coating acting as an adhesive. Said porous FEP-coated ePTFE film 120 may also provide a porous substrate for attachment of coatings such as a therapeutic agent eluting layer 124. In another embodiment, said distal tip assembly 20 comprises another layer of film 122 wrapped around said side wall 104 and covering layer 120. In this embodiment, said film 122 is preferably a porous film or tape such as ePTFE provided with a discontinuous coating of FEP. This layer 122 can serve to keep layer 120 in place. In another embodiment, said distal tip assembly 20 may comprise a therapeutic agent eluting layer 124. In this embodiment said therapeutic agent eluting layer may comprise the previously described thermoplastic fluoroelastomer copolymer TFE/PMVE and a therapeutic agent as previously described. In another embodiment, the therapeutic agent eluting copolymer can be sprayed onto said distal tip assembly 20 to create a therapeutic agent eluting layer 124. In another embodiment, said therapeutic agent eluting copolymer is incorporated into or coated on a film that is applied over said distal tip assembly 20. In another embodiment, said therapeutic agent eluting copolymer can be provided as a pre-formed cover that can be placed over said tip assembly 20. In another embodiment, said tip can be dip-coated with the therapeutic agent eluting copolymer.

In other embodiment of the invention, said layers that cover opening 102 have an eccentric opening 101 (FIG. 6) wherein said fixation member 112 can pass though. Using films to cover opening 102 of said tip housing 105 is beneficial because films are thinner, thus making the tip assembly 20 shorter in length. These films covering opening 102 also provide additional surface area for therapeutic agent elution and may minimize the likelihood of tissue trauma. In addition, the films mentioned above have the necessary strength to support helical fixation member 112 as it threads through eccentric hole 101. Joining of distal tip assembly 20 to the distal end of the body of lead 10 as described above improves reliability through increased tensile strength and lower torque requirements for extending and retracting fixation member 112.

The tip assembly 20 may also include a radiopaque marker to enhance imaging of the location of the tip assembly 20 and/or fixation member 112. This marker may be placed at any location along tip housing or over entire tip housing to provide a reference between the housing and fixation helix to indicate under fluoroscopy when fixation member 112 is fully extended and or retracted. Radiopaque markers may also be added to fixation helix and or post 106 or the internal lumen of tip housing 105.

Figure 8:
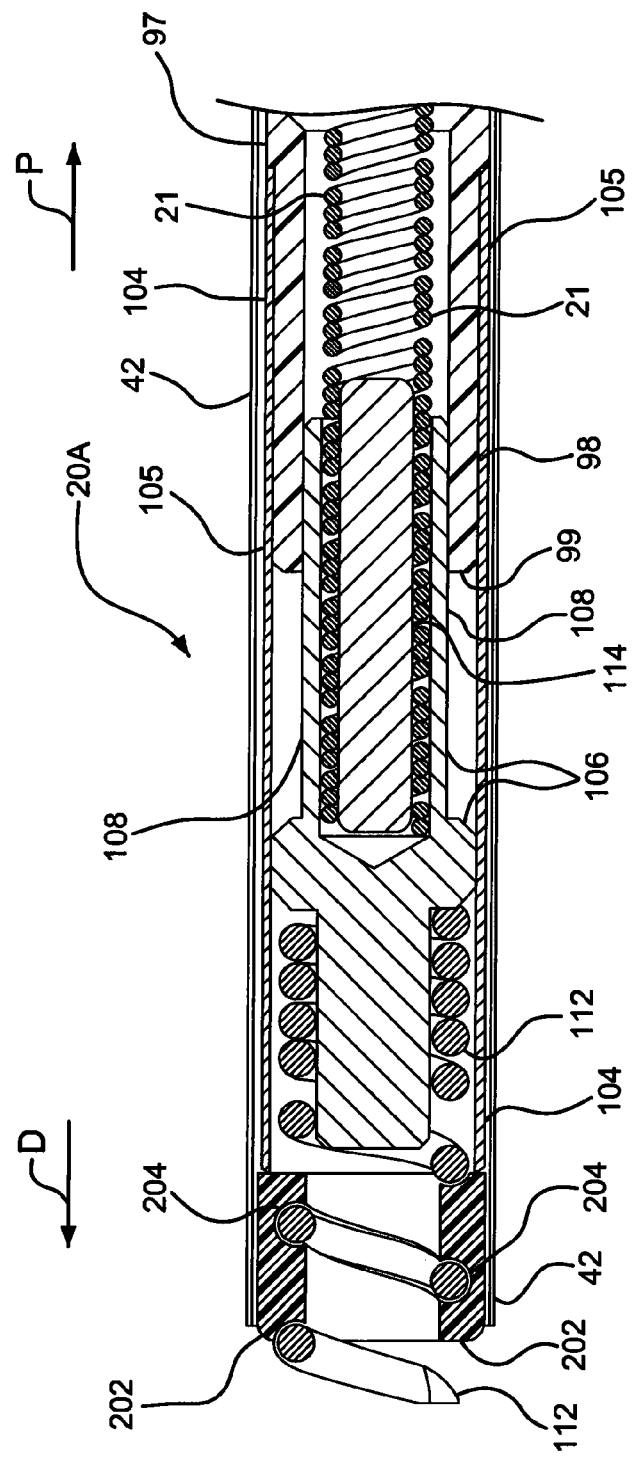
FIG. 8 is a longitudinal cross section showing the construction of an alternative distal lead tip assembly embodiment.

Another embodiment of the invention depicts an alternative tip assembly 20A as illustrated in FIG. 8 and generally constructed in a similar manner as described above. FIG. 8 further depicts a tip assembly 20A that comprises a copolymer cap 202. Said copolymer cap 202 further comprises a helical lumen 204 which guides helical fixation member 112 as it extends or retracts. In one embodiment, said cap 202 is comprised of a therapeutic agent eluting copolymer. In another embodiment, said copolymer is the previously described thermoplastic fluoroelastomer copolymer TFE/PMVE. Examples of therapeutic agents are discussed above. Copolymer cap 202 generally has a cylindrical shape with substantially the same outside diameter as the inside diameter of tip housing 105. One method of making helical lumen 204 is to cure copolymer cap 202 with a helical piece that mimics said helical fixation member 112, but is at least one gauge thicker than said helical fixation member 112. After curing cap 202 comprising said mimic, the mimic is removed from copolymer cap 202, leaving helical lumen 204. In another embodiment, helical lumen 204 can be created by methods known by those skilled in the art.

Once copolymer cap 202 with helical lumen 204 is made, said cap 202 will be placed at the distal end of said tip housing 105. Helical fixation member 112 will be inserted into helical lumen 204 and cap 202 may abut or protrude slightly beyond the distal end of tip housing 105. Cap 202 will be affixed to side wall 104 by wrapping at least one layer of film 42 around cap 202 and side wall 104 of the tip housing 105. In one embodiment, layer 42 is a substantially impermeable layer that extends from the distal end of tip assembly 20A to the distal end of lead 10. This layer serves to electrically insulate tip housing 105 and to attach cap 202 to the side wall 104 of tip housing 105. This layer may be applied by helically wrapping said substantially impermeable film around the cap 202 and the tip housing 105. In one embodiment, said substantially impermeable layer is the previously described substantially impermeable ePTFE/FEP tape. Said tip assembly 20A can be attached to the body of lead 10 as described above.

Figure 9A:
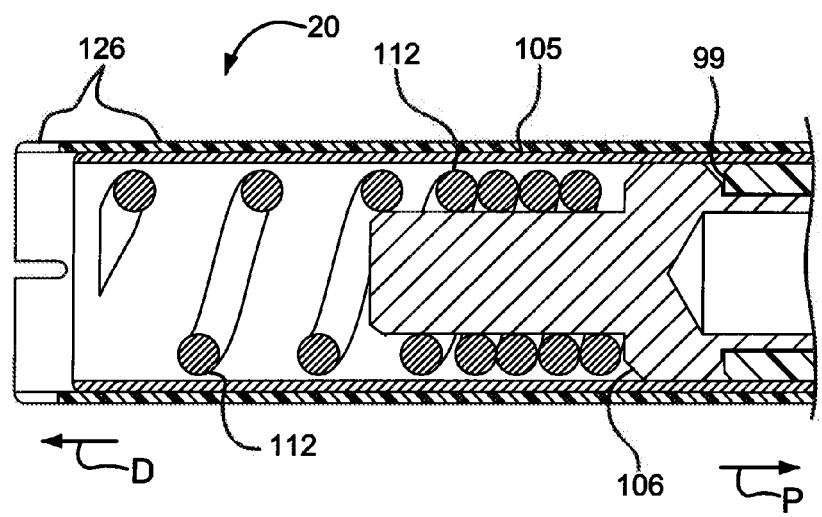
FIGS. 9A and 9B are longitudinal cross sections of a tip housing provided with a flexible polymeric tip flanges outwardly when the tip is affixed to the surface of the heart as shown in FIG. 9B.
Figure 9B:
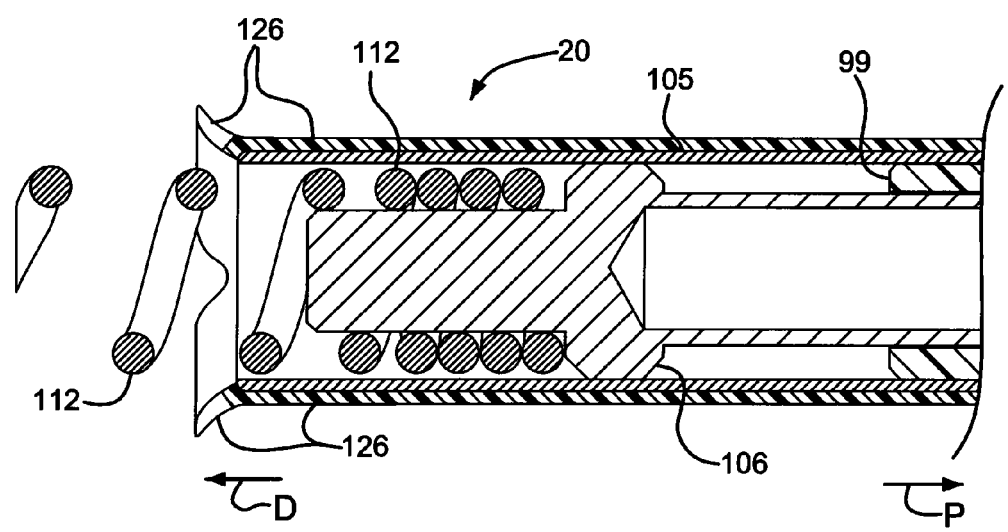

FIGS. 9A and 9B are longitudinal cross sections of a tip housing 105 provided with a flexible polymeric sleeve 126 that flanges outward when the tip 20 is affixed to the surface of the heart as shown in FIG. 9B. Sleeve 126 may be made of any suitably flexible and biocompatible polymeric material. Elastomeric materials capable of eluting therapeutic agents are preferred. A dissolvable coating over the outside of sleeve 126 may be used to prevent a flange from expanding during implantation.

Figure 10A:
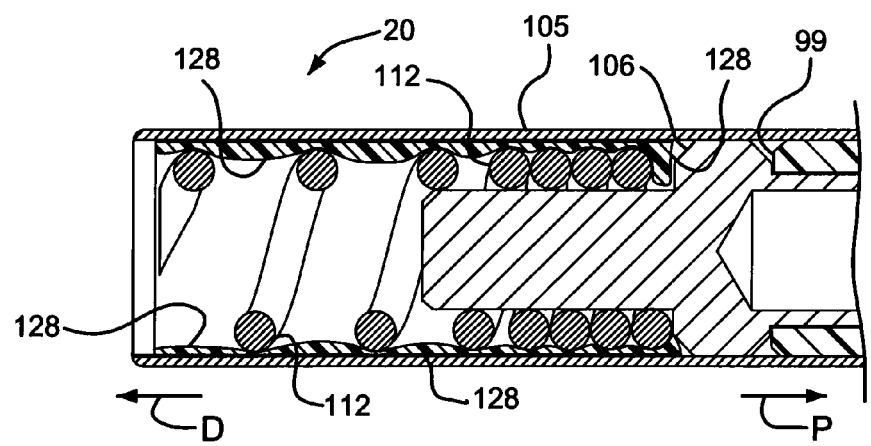
FIGS. 10A and 10B are longitudinal cross sections of a tip housing that incorporates a flexible shape-memory polymer member that extends beyond and flanges outward from the distal end of the tip when the tip is affixed to the surface of the heart as shown in FIG. 10B.
Figure 10B:
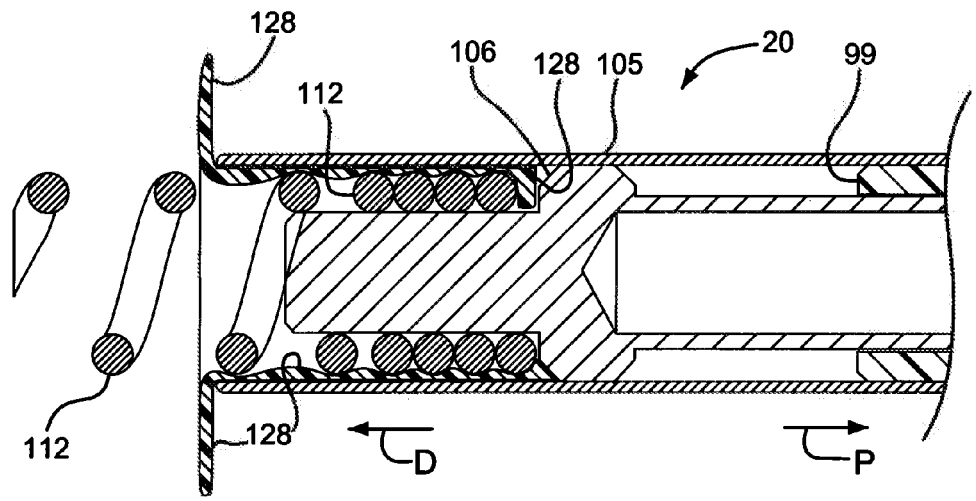

FIGS. 10A and 10B are longitudinal cross sections of a tip housing 105 that incorporates an internal sleeve 128 of a flexible memory polymer that extends beyond and flanges outward from the distal end of the tip 20 when the tip is affixed to the surface of the heart as shown in FIG. 10B. Sleeve 128 may be made of any suitably flexible and biocompatible polymeric material. Elastomeric materials capable of eluting therapeutic agents are preferred.

Figure 11A:
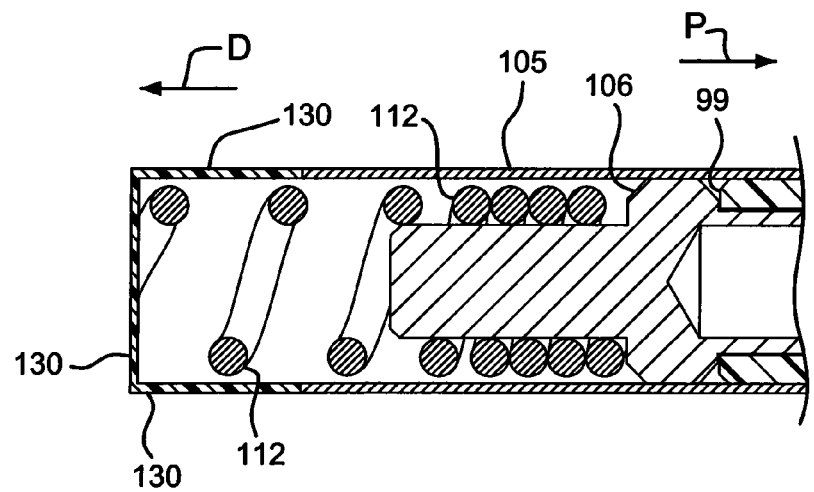
FIGS. 11A and 11B are longitudinal cross sections of a tip housing provided with an extension of the tip housing formed from a flexible polymer member that compresses and flanges outwardly from the distal end of the tip when the tip is affixed to the surface of the heart as shown in FIG. 11B.
Figure 11B:
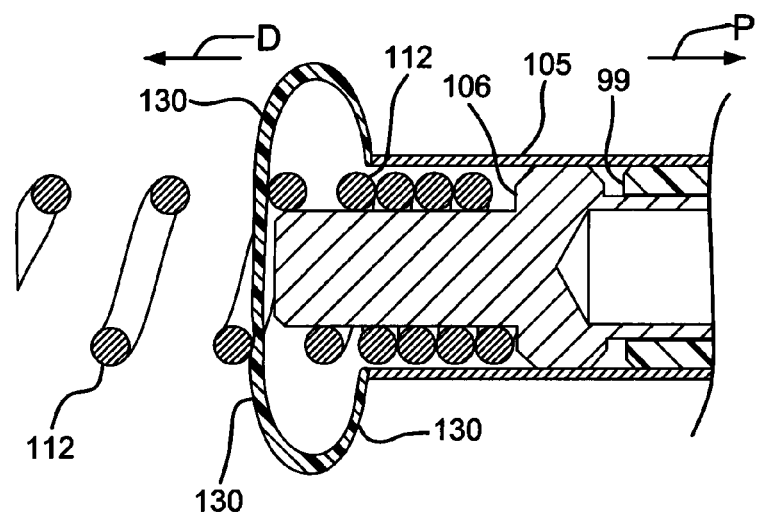

FIGS. 11A and 11B are longitudinal cross sections of a tip housing 105 provided with an extension 130 of the tip housing 105 formed from a flexible polymer that compresses and flanges outwardly from the distal end of the tip 20 when the tip is affixed to the surface of the heart as shown in FIG. 11B. Extension 130 may be made of any suitably flexible and biocompatible polymeric material. Elastomeric materials capable of eluting therapeutic agents are preferred.

Figure 12A:
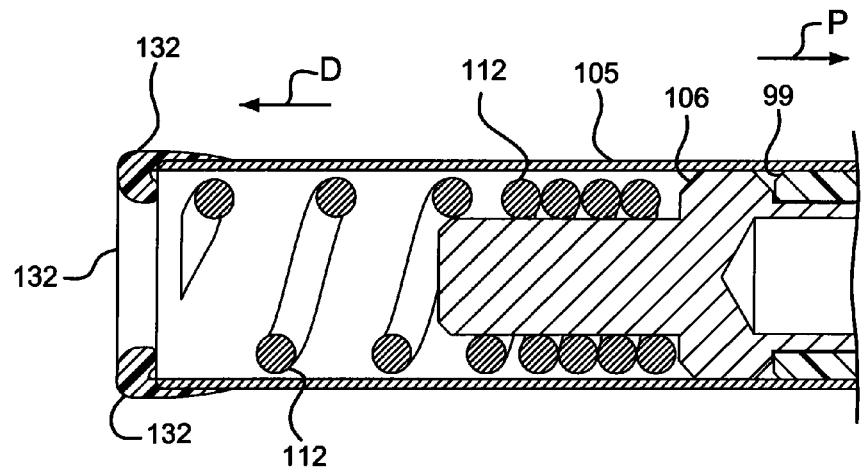
FIGS. 12A and 12B are longitudinal cross sections of a tip housing provided with a flexible shape-memory polymeric ring that flanges outwardly from the distal end of the tip when pushed distally by the extending fixation member during affixing of the tip to the surface of the heart as shown in FIG. 12B.
Figure 12B:
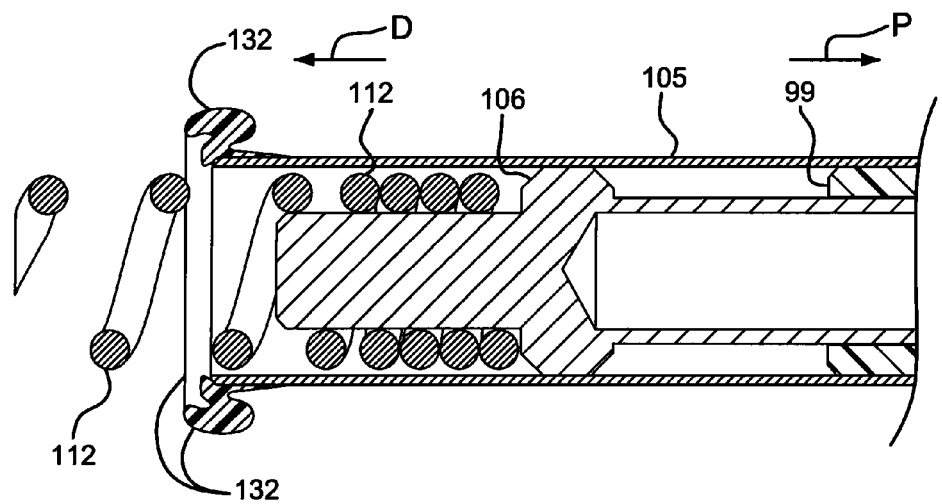

FIGS. 12A and 12B are longitudinal cross sections of a tip housing 105 provided with a flexible shape memory polymeric ring 132 that flanges outwardly from the distal end of the tip when pushed distally by the extending fixation member 112 during affixing of the tip 20 to the surface of the heart as shown in FIG. 12B. Ring 132 may be made of any suitably flexible and biocompatible shape memory polymeric material. Materials capable of eluting therapeutic agents are preferred.

Figure 13A:
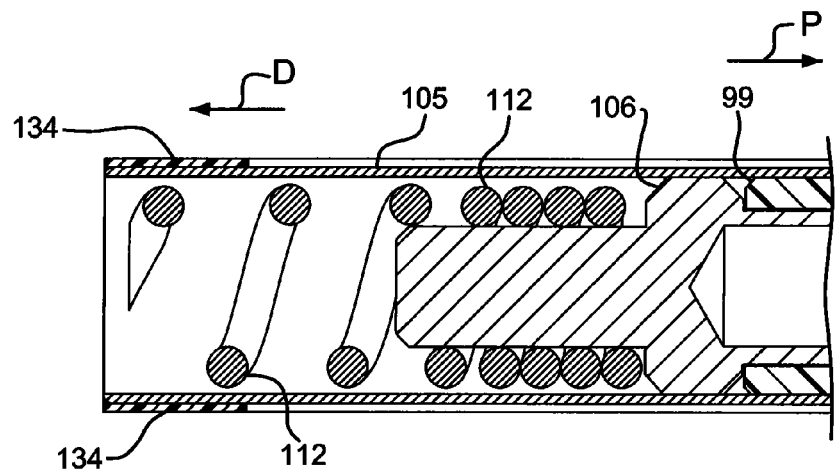
FIGS. 13A and 13B are longitudinal cross sections of a tip housing provided with an outer coating of a biocompatible polymeric hydrogel at the distal end of the housing that expands by absorption of body fluids following implantation as shown in FIG. 13B.
Figure 13B:
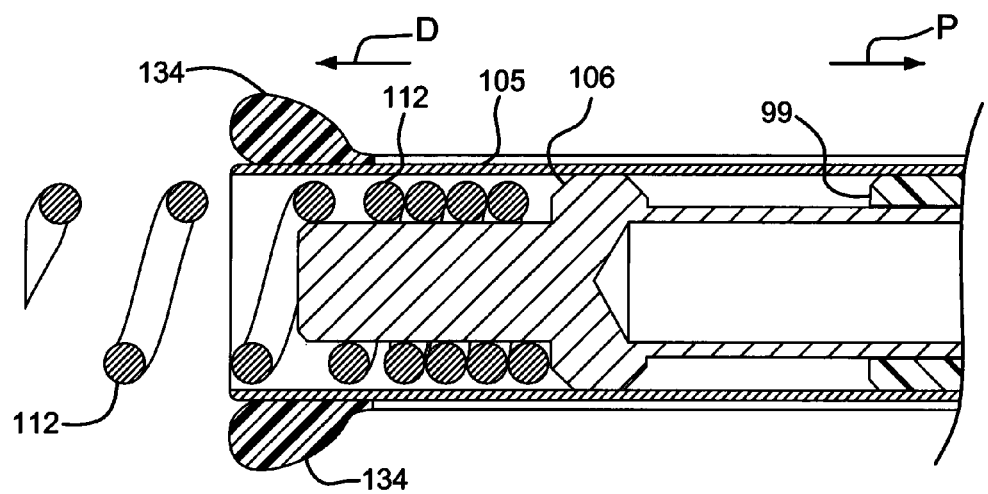

FIGS. 13A and 13B are longitudinal cross sections of a tip housing 105 provided with an outer coating 134 of a biocompatible polymeric hydrogel at the distal end of housing 105 that expands by absorption of body fluids following implantation as shown in FIG. 13B.

FIG. 13B also describes the appearance of a flange 134 made of a bioabsorbable material as it would appear prior to and immediately after implantation, and prior to subsequent bioabsorption. Suitable bioabsorbable materials are well known in the art.

FIGS. 14A and 14B are respectively a perspective view and an end view of a tubular tip housing 105 provided at the distal end with a pair of longitudinally oriented slots 136 with the material of the tip housing between the adjacent slots 136 folded inwardly to form a tab 137 intended to serve as a thread guide for a helical fixation member 112 (not shown). One of slots 136 is longer than the other to provide the bent tab 137 with an angle to correspond with the pitch of the fixation member 112.

FIGS. 15A and 15B are respectively a perspective view and an end view of a tubular tip housing 105 provided with a pair of helically oriented slots 138 with the material of the tip housing 105 between the adjacent slots 138 folded inwardly to serve as a thread guide 139 for a helical fixation member 112 (not shown).

FIGS. 16A and 16B are respectively a perspective view and an end view of a tubular tip housing provided with a pair of longitudinally oriented slots 136 with the material of the tip housing between the adjacent slots extending beyond the length of the tip housing and folded inwardly to form a bent tab 137 intended to serve as a thread guide for the fixation member 112 (not shown). In this embodiment it is apparent that the length of tab 137 as shown in FIG. 16A prior to bending extends beyond the end of tubular tip housing 105. One of slots 136 is longer than the other to provide the bent tab 137 with an angle to correspond with the pitch of the helical fixation member 112.

Figure 17:
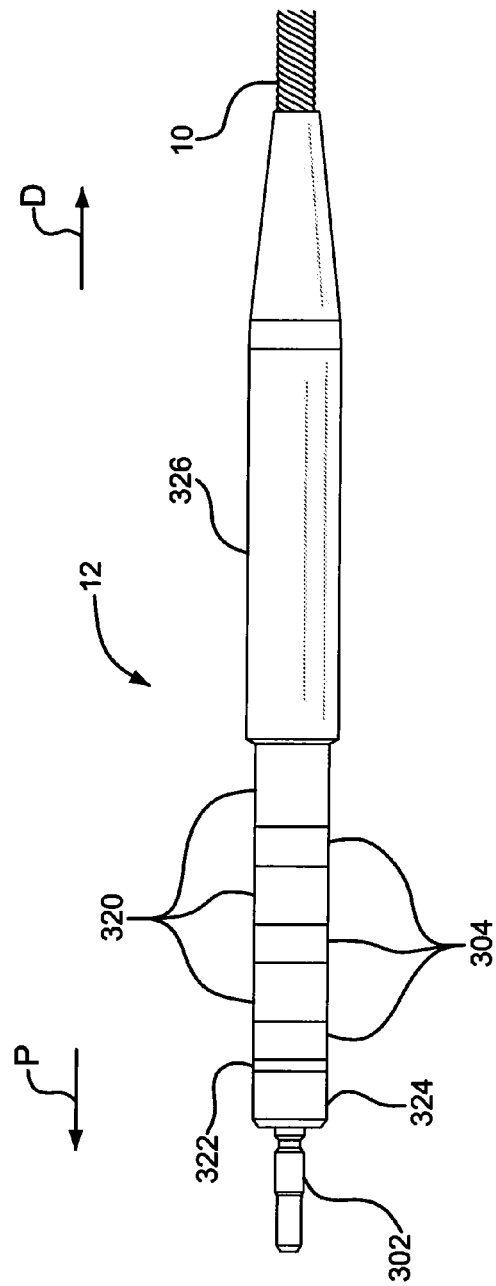
FIG. 17 is a side view of a preferred electrical connector.

Finally, lead 10 is provided with a suitable electrical connector 12 at its proximal end in order that it may be quickly and reliably connected to a power or sensing and control system 11. The connector 12 illustrated in FIG. 17 and subsequent figures, and described below, is generally known in the electrophysiology art as an "IS-4" or "DF-4" connector. The connector 12 is made to be plugged into a receptacle in a power or sensing and control system 11 that accepts IS-4 or DF-4 connectors or in a suitable adapter. The connector 12 comprises ring connector terminals 304, isolation rings 320 and a pin connector 302.

FIG. 18A illustrates a side cross sectional view of connector 12. Connector 12 comprises an insulating sleeve 312, an insulating sleeve lumen 310 and slots 314 through the wall of insulation sleeve 312 which will let first and second lengths segments 22, 24 and 26 described above pass from the lumen 310 of insulating sleeve 312 to the exterior of the insulating sleeve 312. The insulating sleeve 312 can be constructed from any suitable non-conductive biocompatible material, for example, PEEK or PTFE. Pin connector 302 is made from an electrically conductive material and comprises a counterbore 306 where a coiled conductor (not shown) can be inserted. In one embodiment, said coiled conductor is the pacing coil 21 described above. Said coiled conductor electrically couples the pin connector 302 to the fixation member 112 of the distal portion of said medical lead, as described above. The proximal end of the coiled conductor can be secured in place in counterbore 306 by resistive or laser welding, crimping or other methods known in the art. Pin connector bearing 322 accommodates the pin connector flange 308 which in turn is retained axially by retainer cap 324; this assembly allows rotation of the pin connector 302 along its longitudinal axis. Rotation of pin connector 302 will allow fixation member 112 to be inserted into or extracted from tissue, as described above.

FIG. 18A also illustrates contact rings 304. Contact rings 304 can be made from metals such as stainless steel, MP35N, or platinum-iridium alloy. Contact rings 304 are electrically coupled to the proximal ends 318 of said first and second lengths segments 22, 24 and 26 described above. Said conductor ends 318 are stripped of insulation and enter the distal end of the insulating sleeve lumen 310 and are threaded through their respective slots 314 so that wire ends 318 are now on the exterior side of the insulating sleeve 312. Wire ends 318 are then electrically coupled to their respective contact rings 304. Said wire ends 318 can be interference fit, resistance or laser welded, and/or crimped to the luminal surface of contact rings 304. Contact rings 304 are axially separated and electrically isolated from one another by isolation rings 320. Isolation rings 320 can be made from non-conductive biocompatible material such as PEEK or PTFE. In one embodiment, said insulating sleeve 312 comprises a groove or "landing" that can accommodate conductor ends 318. This will make conductor ends 318 flush with the insulating sleeve 312. In another embodiment, said insulating sleeve slots 314 are radially separated by 120°. The schematic transverse cross section of FIG. 18B illustrates that the slots are radially separated (but does not describe the necessary axial separation). In addition, slots 314 are longitudinally or axially separated along the length of the insulating sleeve 312 as shown in shown in FIG. 18A. Said connector 12 may also include a strain relief sheath 326 that encloses the distal portion of the insulating sleeve 312 and sleeve support cap 328 and a proximal portion of the body of lead 10 (not shown). This sheath 326 can be used to prevent contamination from entering the insulating tube lumen 310 and may also serve as a means for gripping the lead connector for insertion or pulling lead connector 12 in and out of a power or sensing and control system 11. Sheath 326 can be made from any suitable electrically insulative biocompatible material and is typically of a polymeric, or preferably, an elastomeric material.

FIG. 19A shows a longitudinal cross section of another embodiment of a connector 12. Connector 12 contains three contact rings 304, each contact ring having a leg 315 (preferably integral with the ring) with an inward bend 316. Each leg extends distally to a tube 317. Where necessary legs pass through any distally-located contact rings 304. FIG. 19A shows only one of the three legs 315, while all three legs 315 appear in the phantom side view of FIG. 19B (as well as cross sectional view 19E). The distal end of each leg 315 has a tube 317 crimped or welded over that end of the leg 315 with the opposite end of each tube 317 left open to accommodate conductors (22, 24 and 26; not shown here) that can be crimped or welded inside that opposite end of the appropriate tube 317. The inner tube 319 is formed during the overmolding between and distal to the contact rings 304 with an insulative polyurethane or silicone injection to provide insulation rings 320 between and adjacent to the contact rings 304. Retainer cap 324 can be threaded onto the proximal end of the threaded inner tube 319 to capture pin connector 302.

FIG. 20A shows a longitudinal cross section of an alternative embodiment of a connector 12. Connector 12 has contacts rings 304 with a pair of larger diameter apertures 305 that insulated wire 22, 24 or 26 (not shown) can pass through and smaller hole(s) 307 that an uninsulated wire end (22, 24 or 26; not shown) can be terminated to through welding, crimping or similar. Additionally contact rings 304 have a center hole 309 allowing for placement of a pacing coil or inner tube 319.

FIGS. 21A and 21B are respectively a longitudinal cross section and a side perspective view and FIGS. 21C, 21D, and 21E are transverse cross sections that describe an electrical connector 12 with a channeled tube 321 intended to allow passage of lead body wires (not shown) and to allow a selected wire to connect with the appropriate contact ring 304. Connector 12 has an inner tube 321 with channels 323 and is made of an insulative polymer such as PEEK. Each channel 323 goes from the distal end of the connector 12 to the appropriate contact ring 304. Conductors (not shown) travel from lead body 10 along the appropriate channel 323 and then are terminated to the appropriate contact ring 304. Any remaining space is then backfilled with an insulative polymer 329 such as silicone or polyurethane, including spaces between and adjacent to contact rings 304.

FIGS. 22A and 22B show perspective views of an inner strain relief portion 327 of connector 12 allowing the helically wound conductors 22, 24 and 26 in the body of lead 10 to transition into a larger pitch for connection to connector 12. Inner strain relief portion 327 may include three wire channels 325 to guide conductors 22, 24 and 26 and gradually increase the diameter at connector 12 from that of lead 10.

The described lead may be made with a variety of techniques and materials of desired dimensions. The following manufacturing descriptions and dimensions are therefore not intended to be limiting.

First, a long length of wire for use as conductors 22, 24 and 26, such as a 1×19 0.165 mm 35 NLT DFT (Ft. Wayne Metals Corp, Ft. Wayne, Ind.) stranded wire, is tape-wrapped with the previously described substantially impermeable ePTFE/FEP insulating tape. The tape is of about 2.5 mm width and is applied with a pitch of about 2.5 mm with the FEP-coated side of the film facing away from the wire surface. The tape-wrapped wire is heated to 320° C. for 20-45 seconds, i.e., a time sufficient to ensure that the construct is heated above the melt point of the FEP. The wrapped wire is then wrapped again in the opposing direction with a 3.3 mm wide tape of the same type at a pitch of 2.9 mm with the FEP facing the wire surface. The wire is heated again above the FEP melt point.

The resulting insulated conductor wire, having a diameter of approximately 0.27 mm, is cut into two 320 cm lengths and one 220 cm length. The integrity of the insulation may be tested at this time by soaking the wires briefly in 100% isopropyl alcohol and then immediately transferring the wire to 9 g/liter saline. A suitable voltage source (e.g., a Quadtech Guardian 12KVDC Hipot Tester (Maynard Mass. 01754)) is connected to both ends of each wire and 5 kV is applied for 15 seconds. Following testing the wires should be rinsed in de-ionized water followed by a rinse in 100% isopropyl alcohol.

Next, the center portion of the length of each wire is stripped of insulation by suitable means (e.g., thermal stripping). The stripped lengths should be about 4.3 cm for one of the 320 cm samples and about 34 cm for the other, and about 34 cm for the 220 cm long wire. Each of these wires is then folded in half at the center of the non-insulated portion, creating a 180° bend at the center of the length of each wire. Finally, a sufficient length of ePTFE filament appropriate to reach the distal end of the constructed lead (further described below), of about 0.125 mm diameter, is inserted into the apex of the bend of each wire and tied at the bend using a surgeon's square knot and the excess filament trimmed.

Both ends of a length of silver-plated copper wire (intended to serve as a construction mandrel) are placed into the chucks of a winding machine. The wire mandrel will be used as a temporary substrate upon which will be wound the multi-filar windings of the above-described conductors. The diameter of the wire mandrel is chosen to be sufficient to provide the necessary clearance to allow a pacing conductor coil to be rotated in the lumen of the multi-filar winding so that the fixation member electrode, attached to the distal end of the pacing coil, may be screwed into or removed from heart tissue. The wire mandrels for the following may be optimized to be the smallest practical diameter that allows for the necessary pacing coil clearance in order that the outside diameter of the finished lead is minimal.

The silver-plated copper wire is then tape-wrapped with a thin ePTFE tape having a thickness of about 0.04 mm and of about 6.4 mm width, with a pitch of about 3.8 mm in a right-hand lay. Another layer of tape is wrapped over this first wrapping, using a 6.4 mm width tape of the same type used for the wire insulating process described above, applied with a 3.6 mm pitch in a right-hand lay with the FEP-coated side of the film facing away from the surface of the silver-plated copper wire. Next, a third layer is over wrapped with the same tape used for the first layer of wrapping, this time applied at a 3.0 mm pitch in a right-hand lay. Finally, another layer of this same tape is over wrapped at a 2.8 mm pitch in a left-hand (i.e., opposing direction of wrap) lay.

Next, all three of the filaments are laid across the mandrel such that the distance of the filament portion between the mandrel and the wire bend corresponds with the desired spacing between electrodes. The bend of the 4.3 m stripped length, 320 cm overall length wire is positioned closest to the mandrel. The bend of the 34 cm stripped length, 320 cm overall length wire is placed 32 mm further from the mandrel than the first bend. Finally, the third bend of the 34 cm stripped length, 220 cm overall length wire, is placed 47 cm further from the mandrel than the first bend. The free ends of all the filaments are spiraled together in a right-hand lay direction around the mandrel at least 10 turns, and then tied as a group with at least 5 hitch knots.

Rotating the winding machine in a right-hand lay direction, the fiber/wire combinations are coiled onto the mandrel, taking care that all wires lay flat without crossing or twisting throughout winding process, at a 0.49 mm pitch until the end of the 4.3 cm stripped portion reaches the mandrel. Coiling is continued at a 0.76 mm pitch until the bend of the first 34 cm stripped portion reaches the mandrel, then at 1.03 mm pitch until the end of the first 34 cm stripped portion, then at 1.29 mm pitch until the bend of the second 34 cm stripped portion, then at 1.73 mm pitch until the end of the second 34 cm stripped portion, and finally at 2.09 mm pitch until the entire coiled length is then greater than about 53 cm. The wire ends are temporarily taped down to prevent uncoiling.

Next, at the distal end of the construction immediately adjacent to the first-created electrode of the multi-filar coiled wire construction (the construction having been started with the distal end and progressing to the proximal end), a circumferential wrap (i.e., not helical) of a 3.2 mm wide tape is applied, using the previously described substantially impermeable ePTFE/FEP insulating tape, until a lead diameter of 1.50 mm is achieved.

The electrode segment nearest the distal end (comprising the uninsulated wire resulting from the 4.3 cm stripped wire length), that is, the sensing electrode, is then circumferentially wrapped with two or three layers of a 3.20 mm wide tape that had been slit from a carbon-loaded ePTFE film. This carbon-loaded ePTFE film has a density of about 0.4 g/cc, is about 0.13 mm thick with about 25% ketchum-black carbon loading by weight and an visually-estimated mean fibril length of about 10 microns (from scanning electron photomicrographs of the film surface). Carbon-loaded ePTFE films may be made as taught by U.S. Pat. No. 4,985,296 to Mortimer.

Next, an ePTFE film that has been coated with a layer of the previously described thermoplastic fluoroelastomer copolymer is obtained. The ePTFE film used is a film made as taught by U.S. Pat. No. 7,306,729 to Bacino et al., having a thickness of less than about 0.0025 mm. With the fluoroelastomer coating, the composite film has a thickness of about 0.028 mm. This film is slit into a 3.2 mm wide tape, six layers of which is then circumferentially wrapped around the construct immediately adjacent to the proximal end of the sensing electrode (the first-created electrode made from the 4.3 cm length of uninsulated wire) with the fluoroelastomer side of the composite tape facing the surface of the lead. This wrapping forms a seal component that will separate the electrode from the adjacent length of insulated portion of the lead and prevent the insulated portion from being contaminated with body fluids.

Using a 6.4 mm wide tape of the same composite ePTFE/fluoroelastomer film, five layers are applied as a circumferential wrap immediately adjacent to the proximal end of the second-created electrode (i.e., the distal defibrillation electrode that was made from the first 34 cm length of uninsulated wire). The same type of wrapping is applied immediately adjacent to both ends of the third-created electrode (i.e., the proximal defibrillation electrode that was made from the second 34 cm length of uninsulated wire).

A 0.76 mm wide carbon-filled ePTFE tape of the type described above is wrapped over the distal and proximal defibrillation electrodes, between the seal components in order to fill the slight depression resulting from the uninsulated portion of the conductors used for the electrodes.

A 3.2 mm width of the carbon-filled ePTFE tape is helically wrapped with a 4.32 mm pitch in a right-hand lay over the proximal and distal defibrillation electrodes between the seal components ensuring a tight butt-joint with the seal components. A second wrap of this film is applied over the first wrap in the same manner except with a 3.8 mm pitch applied with a left-hand lay.

Next, the entire length of the lead is helically wrapped with a 13.0 mm width of an ePTFE tape at a pitch of 4.3 mm. The film is the same film described above as taught by U.S. Pat. No. 7,306,729 to Bacino et al., having a thickness of less than about 0.0025 mm.

Using a 3.2 mm width of the previously described substantially impermeable ePTFE/FEP insulating tape, three layers are circumferentially wrapped over the ePTFE/fluoroelastomer composite tape previously applied immediately adjacent to the proximal end of the sensing electrode, with the FEP side of the tape facing the surface of the lead. Next, a 6.4 mm width of this same ePTFE/FEP insulating tape is wrapped over the insulated lead portions (i.e., non-electrode portions) proximal to the proximal end of the distal defibrillation electrode including over the seal components at a pitch of 3.7 mm. Finally, the entire construct is heated in a convection oven set at 320° C. for 3 minutes.

After removing the construct from the oven and allowing it to cool to ambient temperature, all ePTFE tape previously applied to the surface of the silver-plated copper wire mandrel that is exposed adjacent to the distal end of the previously applied 1.5 mm diameter wrapping of the previously described substantially impermeable ePTFE/FEP insulating tape (located at the distal end of the construct) is removed by skiving.

A tubular housing, intended for use with the distal tip assembly and pacing electrode, is fabricated by cutting a 7.0 mm length of 0.064 mm wall thickness 304 or 316 stainless steel tubing having an inside diameter of 1.37 mm. This tubular housing is slid over the end of the silver-plated copper wire mandrel along with a support coil temporarily fitted inside of the tubular housing until the housing butts against the 1.5 mm diameter wrapping of the insulating tape at the distal end of the construct.

Using a 6.4 mm width of the ePTFE/FEP insulating tape, a helical wrap is applied (FEP-coated side facing the lead) beginning over the 1.5 mm diameter wrapping of insulating tape and progressing distally over the end of the tubular housing. Next, a circumferential wrap of the same tape (also FEP-coated side facing the lead) is applied over the 1.5 mm diameter wrapping of insulating tape and extending 3.2 mm over the proximal end of the tubular housing until a diameter of 1.7 mm is achieved.

The construct is then heated in an oven set at 320° C. for 4 minutes. After removal from the oven and cooling to ambient, the insulating tape is trimmed from the distal transverse edge of the tubular housing and the internal support coil is removed.

Next, the lead assembly is treated with a wetting agent. First, the covered coil is soaked in isopropyl alcohol (IPA) at ambient temperature (about 21° C.) for 15 minutes. The covered coil is then immediately transferred to a solution of 2.0% polyvinyl alcohol (PVA) and de-ionized water and allowed to soak at ambient temperature for 70 minutes. Next, the covered coil is rinsed for 20 minutes in de-ionized water at ambient temperature, after which it is soaked for 50 minutes in a solution of 2% gluteraldehyde, 1% hydrochloric acid (HCL) and de-ionized water, at ambient temperature. Finally, the covered coil is rinsed in de-ionized water at ambient temperature for 2 hours and allowed to dry in ambient air.

After the wetting agent treatment, the resulting lead is removed from the silver-plated copper wire mandrel by applying appropriate tension to the mandrel ends to cause the mandrel to elongate approximately 15 cm, resulting in sufficient necking of the mandrel to allow the lead to slide freely on the mandrel. Leaving the mandrel in place, a DF-4 connector may be assembled onto the proximal end of the lead body. A sleeve support cap, first, and an insulating sleeve, second, are slid over the lead body from the proximal end toward the distal end. The wire ends (2) of the first and second length segments for the sensing electrode are pulled through the most proximal slot in the insulating sleeve. The wire ends are then thermally stripped adjacent to the insulating sleeve. A contact ring is slid on from the distal end of lead and over the sleeve support cap and onto the insulating sleeve and pressed over the sensing electrode wire ends with an interference fit until flush with proximal end of insulating sleeve. An isolation ring is then slid into place from the distal end of lead until it abuts the previous ring contact. The distal defibrillation electrode wire ends are then pulled through the middle slot, stripped and then another ring contact and then another isolation ring are slid into place as described above. Next, the proximal defibrillation electrode wire ends are pulled through the distal slot, stripped and then a contact ring, followed by another, longer isolation ring are slid into place as previously described. The pin connector bearing is pressed into proximal end of insulating sleeve. Protruding wire ends are trimmed adjacent to each respective proximal end of ring contacts and all rings are pressed together to close any gaps. Medical adhesive may be used to glue individual parts together in assembly, and may also be used to backfill inside of the insulating sleeve. A strain relief sheath (preferably of silicone) is then slid over the distal end of the lead and onto the distal end of the connector and attached with medical adhesive. With the adhesive dry, the multi-filar winding liner may be trimmed flush with the pin connector bearing and the mandrel removed.

A 6-filar pacing coil is constructed using a 0.46 mm silver-plated copper wire mandrel. Each filar is 0.076 mm 35NLT, 28% silver DFT wire (Fort Wayne Metals Corp., Ft. Wayne Ind.). Alternatively, multi-stranded wire may also be used. The 6 filars are coiled onto the mandrel at a pitch of 0.51 mm in the left-hand lay direction. Both ends of the coil are secured to the mandrel before cutting wires to keep the coil from relaxing into an increased diameter. The coil is then wrapped with an 3.175 mm wide substantially impermeable ePTFE/FEP insulating tape at a pitch of 2.85 mm (with the FEP-coated side facing the wire) and another wrap with the same tape in the opposite lay (also FEP down) at a pitch of 2.62 mm. The coil is then heated at 320° C. for approximately 4 minutes. The pacing coil is removed from mandrel by stretching the silver-plated copper wire until the coil is free to slide on mandrel and then the ends are trimmed off to achieve the desired length.

A suitable fixation helix and post component is obtained; the helix is preferably attached to the post by welding. A 0.51 mm diameter by 3.05 mm long stainless steel wire is inserted into one end of pacing coil until flush with end. This end is inserted into the sleeve portion of the post/fixation helix assembly and crimped together, securing the post to the coil both mechanically and electrically. The pacing coil conductor is then inserted into the distal end of the previously manufactured lead. With the fixation helix located within the tubular housing provided for the pacing electrode, a small cut and fold (adjacent edges of the cut are folded inward and caused to slightly overlap) is formed into the distal edge of the tubular housing, at only one point along the circumference of the distal edge of the tubular housing. The cut and fold should be sufficient to serve as a guide to prevent the fixation helix from free-spinning without advancing.

A short length of 3.175 mm width of the previously described substantially impermeable ePTFE/FEP insulating tape is attached with a heated iron (set at about 330° C.) parallel to outside of the tubular tip housing (FEP-coated side facing down) and pulled over open distal tip of housing and attached to opposite side of tubular tip housing. The tape ends are trimmed at approximately the proximal end of tip housing and all edges are well-bonded with soldering iron. This is repeated for a total of two to five layers with each layer clocked at different locations around tip (i.e., radially disposed at about 72° intervals). Another length of this same tape is then applied helically (FEP-coated side facing down) over entire length of the tip housing. A length of FEP-coated porous ePTFE tape of about 6 mm width and a thickness of less than about 0.0025 mm is applied (FEP-coated side down) with one layer over the end of the housing and a helical layer around the housing in a fashion similar to the previously-applied tape layers. This ePTFE tape is generally made as taught by U.S. Pat. No. 5,476,589 to Bacino, and provided with a discontinuous coating of FEP as taught by U.S. Pat. No. 6,159,565 to Campbell et al. This layer is bonded by applying localized convection heat at 320° C. for a time sufficient to bond the film. A coating of the previously described TFE/PMVE fluoroelastomer copolymer containing dexamethasone sodium phosphate is spray-coated onto the exterior surface of the tip assembly sufficient to apply approximately 1 mg of the steroid.

Torque is applied to the exposed proximal end of the pacing coil conductor sufficient to cause the fixation helix to rotate, extend distally and pierce the film covering the distal end of the tubular housing. Manual manipulation of the film may be required to aid the helix in piercing the film. The fixation helix is then fully retracted into the tubular tip housing (in the proximal direction, by rotating the proximal end of the pacing coil in the opposite direction). Next, the exposed proximal end of the pacing coil conductor may be trimmed to an appropriate length, after which the pin connector of a DF-4 connector is attached to the proximal end of the pacing coil conductor. This is accomplished by first inserting a stainless steel tube (0.53 mm outside diameter, 0.41 mm inside diameter and 5.6 mm length) into proximal end of pacing coil until flush. The tube and the proximal end of the pacing coil are then inserted into the female socket of the pin connector until the pin connector is nested into the pin connector bearing and crimped on proximal of connector flange. Finally, the retainer cap is fitted over the end of the pin connector and pressed into the pin connector bearing.

An alternative manufacturing description is also provided that includes the use of a helically wound noble wire applied around the circumference of a length of insulated wire to form an electrode. Other details are changed as well while still other aspects remain the same. The aspects that remain the same are repeated in the following description to provide continuity of the description.

First, a long length of wire for use as conductors 22, 24 and 26, such as a 1×19 0.165 mm 35 NLT DFT (Ft. Wayne Metals Corp, Ft. Wayne, Ind.) stranded wire, is tape-wrapped with the previously described substantially impermeable ePTFE/FEP insulating tape. The tape is of about 2.5 mm width and is applied with a pitch of about 2.5 mm with the FEP-coated side of the film facing away from the wire surface. The tape-wrapped wire is heated to 320° C. for 20-45 seconds, i.e., a time sufficient to ensure that the construct is heated above the melt point of the FEP. The wrapped wire is then wrapped again in the opposing direction with a 3.3 mm wide tape of the same type at a pitch of 2.9 mm with the FEP facing the wire surface. The wire is heated again above the FEP melt point.

The resulting insulated conductor wire, having a diameter of approximately 0.27 mm, is cut into two 320 cm lengths and one 220 cm length. The integrity of the insulation may be tested at this time by soaking the wires briefly in 100% isopropyl alcohol and then immediately transferring the wire to 9 g/liter saline. A suitable voltage source (e.g., a Quadtech Guardian 12KVDC Hipot Tester (Maynard Mass. 01754)) is connected to both ends of each wire and 5 kV is applied for 15 seconds. Following testing the wires should be rinsed in de-ionized water followed by a rinse in 100% isopropyl alcohol.

Next, the center portion of the length of each wire is stripped of insulation by suitable means (e.g., thermal stripping). The stripped lengths should be about 3 cm for one of the 320 cm samples and about 33 cm for the other, and about 36 cm for the 220 cm long wire.

The stripped portion is then tape-wrapped with the previously described thinner, substantially impermeable ePTFE/FEP insulating tape] of a slit width of about 2 mm resulting in an insulation thickness of about 0.01 mm. Platinum/Iridium wire of about 0.05 mm diameter with then coiled over the thinly insulated section at a pitch of about 0.08 mm with the Pt/Ir wire being passed across a metal surface heated to about 700° C. in close proximity to where it coils onto the thinly insulated conductor. The temperature used is preferably above the melt point of the underlying thin conductor insulation. The Pt/Ir coil is held down on the ends with a fluoroelastomer adhesive to prevent loosening or movement of the coil. A 3.2 mm wide slit of the thin previously described substantially impermeable ePTFE/FEP insulating tape is wrapped radially around the center portion of the platinum-iridium coil with 2-4 layers.

Each of these wires is then folded in half at the center of the platinum-iridium coiled portion where the 3.2 mm insulation is, creating a 180° bend at the center of the length of each wire. Finally, a sufficient length of ePTFE filament appropriate to reach the distal end of the constructed lead when folded in half (further described below), of about 0.1 mm diameter, is looped around the apex of the bend of each wire with a triple cableman's knot as shown in FIG. 3D.

Both ends of a length of silver-plated copper wire (intended to serve as a construction mandrel) are placed into the chucks of a winding machine. The wire mandrel will be used as a temporary substrate upon which will be wound the multi-filar windings of the above-described conductors. The diameter of the wire mandrel is chosen to be sufficient to provide the necessary clearance to allow a pacing conductor coil to be rotated in the lumen of the multi-filar winding so that the fixation member electrode, attached to the distal end of the pacing coil, may be screwed into or removed from heart tissue. The wire mandrels for the following may be optimized to be the smallest practical diameter that allows for the necessary pacing coil clearance in order that the outside diameter of the finished lead is minimal.

The silver-plated copper wire is then tape-wrapped with a thin ePTFE tape having a thickness of about 0.04 mm and of about 6.4 mm width, with a pitch of about 3.8 mm in a right-hand lay. Another layer of tape is wrapped over this first wrapping, using a 6.4 mm width tape of the same type used for the wire insulating process described above, applied with a 3.6 mm pitch or alternatively the thinner substantially impermeable ePTFE/FEP insulating tape described previously in a 6.4 mm width applied at a pitch of 1.3 mm pitch. This layer is applied in a right-hand lay with the FEP-coated side of the film facing away from the surface of the silver-plated copper wire. Next, a third layer is over wrapped with a fluoroelastomer laminated to a thin ePTFE tape (same as first layer) of a width of 3.2 mm at a pitch of 1.9 mm in a left hand lay with the fluoroelastomer facing away from the surface.

Next, all three of the filaments are laid across the mandrel such that the distance of the filament portion between the mandrel and the wire bend corresponds with the desired spacing between electrodes. The bend of the 3 cm stripped length, 320 cm overall length wire is positioned closest to the mandrel. The bend of the 33 cm stripped length, 320 cm overall length wire is placed 32 mm further from the mandrel than the first bend. Finally, the third bend of the 36 cm stripped length, 220 cm overall length wire, is placed 45 cm further from the mandrel than the first bend. The free ends of all the filaments are spiraled together in a right-hand lay direction around the mandrel at least 10 turns, and then tied as a group with at least 5 hitch knots.

Rotating the winding machine in a right-hand lay direction, the fiber/wire combinations are coiled onto the mandrel, taking care that all wires lay flat without crossing or twisting throughout winding process, at a 0.76 mm pitch until the bend of the 33 cm portion is about 1 cm from the mandrel. Coiling is continued at 1.29 mm pitch until the bend of the 36 cm portion is about 1 cm from the mandrel. Winding is continued at 2.09 mm pitch until the entire coiled length is then greater than about 53 cm. The wire ends are taped down to prevent uncoiling.

The SVC and RV electrodes are wrapped with 5-6 layers of 6.4 mm wide tape that had been slit from a carbon-loaded ePTFE film in the opposite lay of the conductors. This carbon-loaded ePTFE film has a density of about 0.7 g/cc, is about 0.03 mm thick with about 27% ketchum-black carbon loading by weight. Carbon-loaded ePTFE films may be made as taught by U.S. Pat. No. 4,985,296 to Mortimer. The tape is cut parallel to the mandrel to create a 6.4 mm long taper of the thickness at each end of SVC electrode and at the proximal end of the RV electrode. The distal end of the RV electrode is cut at about 103 degrees from the mandrel on the distal side of the tape to achieve a 3.2 mm taper.

Next, at the distal end of the RV electrode, a 3.2 mm width of an ePTFE film that has been coated with a layer of the previously described thermoplastic fluoroelastomer copolymer is obtained. The ePTFE film used is a film made as taught by U.S. Pat. No. 7,306,729 to Bacino et al., having a thickness of less than about 0.0025 mm. With the fluoroelastomer coating, the composite film has a thickness of about 0.028 mm. This film is overlapped onto the carbon-loaded ePTFE film about 3.2 mm and wrapped with about 4 layers, the fluoroelastomer-coated side facing inward, to the proximal end of the sensing electrode created by the 3 cm stripped and coiled portion of the conductor. The film is cut parallel to the mandrel creating a 3.2 mm opposing taper with the carbon-loaded ePTFE film on the proximal side and a 3.2 mm taper adjacent to the sensing electrode. A 3.2 mm width of the previously described carbon-loaded ePTFE is overlapped about 3.2 mm onto the distal end of the fluoroelastomer-coated ePTFE and wrapped with 5-6 layers to the distal end of the sensing electrode. The film is cut perpendicular to the mandrel on the distal end.

Next, a 3.2 mm width of the previously described fluoroelastomer-coated ePTFE is wrapped circumferentially directly distal to the bend of the sensing electrode adjacent to the carbon-loaded ePTFE with about 8 layers. This is then over-wrapped circumferentially with 6.4 mm wide previously described thinner, substantially impermeable ePTFE/FEP insulating tape with FEP-side facing inward. About 5 layers are applied overlapping the carbon-loaded ePTFE film over the sensing electrode by about 1 mm. The fluoroelastomer-coated ePTFE portion between the sensing and RV electrodes is over-wrapped with the previously described thinner, substantially impermeable ePTFE/FEP insulating tape of a width of 3.2 mm FEP-side facing inward with about 5 layers overlapping equally onto the carbon-loaded ePTFE of the sensing and RV electrodes.

A 6.4 mm width of the previously described fluoroelastomer-coated ePTFE is wrapped with fluoroelastomer facing inward with about 4 layers between the SVC and RV electrodes and proximal of the SVC electrode for about 25 cm in the opposite lay of the conductors (same lay as the carbon-loaded ePTFE). For greater abrasion-resistance and increased robustness of the lead body proximal of the SVC electrode, the 4 layers of fluoroelastomer-coated ePTFE may be transitioned into 6 layers by decreasing the wrapping pitch at a desired distance, (e.g., 3 cm) proximal of the SVC electrode.

The film is cut into a tape with parallel edges and overlapped about 6.4 mm onto the carbon-loaded ePTFE at each end of the SVC electrode and the proximal end of the distal electrode to create the opposing taper. These portions are then over-wrapped with the previously described thinner, substantially impermeable ePTFE/FEP insulating tape, FEP inward, with about 5 layers overlapping onto the carbon-loaded ePTFE about 1 mm on each end of the SVC electrode and the proximal end of the RV electrode. A 0.0025 mm thick, 6.4 mm wide, porous ePTFE tape, made as taught by U.S. Pat. No. 5,476,589 to Bacino, and provided with a discontinuous coating of FEP as taught by U.S. Pat. No. 6,159,565 to Campbell et al., is overwrapped over the previous layer at the proximal end for about 3.5 cm and about 4 layers with FEP-inward to improve adhesion of the silicone strain relief of the IS-4 connector described later.

Clamps with a through hole of about 1.65 mm may be applied over the location of each bend to prevent movement of the bends during cooking. A bend may also placed in the distal end of the lead and mandrel prior to cooking resulting in a set curve in the final lead on the distal end. The entire construct is heated in a convection oven set at 320° C. for 15 minutes.

After removing the construct from the oven and allowing it to cool to ambient temperature, all ePTFE tape previously applied to the surface of the wire mandrel that is exposed adjacent to the distal end of the previously applied 3.2 mm circumferentially wrapped fluoroelastomer-coated film (located at the distal end of the construct) is removed by skiving.

A tubular housing, intended for use with the distal tip assembly and pacing electrode, is fabricated by cutting a 7.0 mm length of 0.064 mm wall thickness 304 or 316 stainless steel tubing having an inside diameter of 1.37 mm. This tubing may be laser cut to include a feature that can be bent into the lumen providing a thread guide as described previously. The housing may also include a PTFE bushing in the proximal end to support the helix assembly during extension and retraction. This tubular housing is slid over the end of the silver-plated copper wire mandrel along with a support coil temporarily fitted inside of the tubular housing and PTFE bushing until the housing butts against the skived edge at the distal end of the construct.

Using a 6.4 mm width of the ePTFE/FEP insulating tape, a helical wrap is applied (FEP-coated side facing inward) beginning over the thinner, substantially impermeable ePTFE/FEP insulating tape at the distal end of the carbon-loaded ePTFE film of the sensing electrode and progressing distally over the end of the tubular housing applying about 5 layers. The same film is then wrapped back in the opposite direction over the same portion with the same number of layers. Next, a circumferential wrap of the same tape the previously described fluoroelastomer/ePTFE laminate film (fluoroelastomer-inward) is applied at the proximal end of the tubular housing and adjacent to the carbon-loaded ePTFE film of the sensing electrode until a diameter of 1.63 mm is achieved. Next, 5 layers of 6.4 mm previously described thinner, substantially impermeable ePTFE/FEP insulating tape is wrapped circumferentially (FEP side facing down or inwardly) over the previous fluoroelastomer/ePTFE circumferential wrap. Additionally, a 0.0025 mm thick, 6.4 mm wide, porous ePTFE tape, made as taught by U.S. Pat. No. 5,476,589 to Bacino, and provided with a discontinuous coating of FEP as taught by U.S. Pat. No. 6,159,565 to Campbell et al., may be applied circumferentially (FEP side facing down or inwardly) with about 2-3 layers over the distal end of the tubular housing to allow for adhesion of drug-eluting layers and/or tip flange features.

The curve on the distal end is reformed, if applicable, and the construct is then heated in an oven set at 320° C. for 5 minutes. After removal from the oven and cooling to ambient, the insulating tape is trimmed from the distal transverse edge of the tubular housing and the internal support coil is removed.

The clamps over the bends are also removed. The carbon-loaded ePTFE film is then densified against a heated rod at 365° C. by spinning the construct at about 1000 rpm and traversing at 12.7 cm/min with a pass in each direction.

The IS-4 connector is made using 3 contact rings with legs. Contact rings are laser-cut from a stainless steel tube of an OD of 3.2 mm and an ID of 2.7 mm. Each leg is cut about 0.3 mm wide. The sensing contact leg is 0.16.3 mm long, the distal contact leg is 11.8 mm long, and the proximal contact leg is 7.2 mm long. Each leg is bent inward at the junction with the ring portion of the contact and bent in the opposite direction about 1 mm from the ring so that the leg becomes parallel with the axis of the ring. The created jog brings the leg about 0.7 mm inward. The leg of each contact is inserted into a stainless steel tube (0.53 mm outside diameter, 0.41 mm inside diameter and 7.6 mm length) about 3.8 mm and the tube is crimped in place. Each contact is assembled over an inner tub (1×72 UNF Thread OD and 1.1 mm ID) with the leg of the sensing contact passing through both the distal and proximal contact, and the distal contact passing through the proximal contact. Each leg is spaced about 120 degrees apart axially. Each contact is spaced apart according to published IS-4 specifications and the threaded tube is positioned approximately aligned with the open end of the tube on the contact legs and protruding beyond the edge of the sensing contact the appropriate depth given the hole and shoulder on the IS-4 cap. The appropriate depth should accommodate the flange on the connector pin allowing it to be trapped between the inner tube and the IS-4 cap allowing for rotation with limited axial movement when the IS-4 cap is fully seated into the sensing contact. The cap and connector pin are described further later. The contacts and inner tube are over-molded with a high-durometer silicone, epoxy, or polyurethane providing a smooth transition from the molded face to the OD of the contacts. Appropriate molding techniques are employed to reduce air bubbles and improve adhesion to contacts and inner tube. Approximately 2.5 mm of the open ends of the tubes crimped to the contact legs are left exposed at the distal end of the molded connector.

A portion of the conductors off the end of the wrapped portion of the lead construct are unwound to expose a portion of the inner-wrapped layers at least as long as the IS-4 inner tube. This is preferably done before the silver-plated copper wire mandrel is necked and removed. The IS-4 connector is slide over these film layers adjacent to the helically wound conductors. The insulation of each conductor is stripped away near where is leaves the helically winding. Each conductor is cut at the appropriate length and inserted into the corresponding tube on the IS-4 connector with two stripped conductors inserted into each tube. The tube is crimped to secure the conductors both mechanically and electrically. A silicone strain relief is then over-molded over the distal end of the IS-4 where these connections are made and extends onto the lead body. A pre-molded strain relief may also be used and attached with silicone medical adhesive filling the area where these connections are made in a counter-bore of the strain relief and also adhering the strain relief to the lead body and IS-4 connector.

Once silicone is properly cured, the resulting lead is removed from the silver-plated copper wire mandrel by applying appropriate tension to the mandrel ends to cause the mandrel to elongate approximately 15 cm, resulting in sufficient necking of the mandrel to allow the lead to slide freely off the mandrel.

A 6-filar pacing coil is constructed using a 0.46 mm silver-plated copper wire mandrel. Each filar is 0.076 mm 35NLT, 28% silver DFT wire (Fort Wayne Metals Corp., Ft. Wayne Ind.). Alternatively, multi-stranded wire may also be used. The 6 filars are coiled onto the mandrel at a pitch of 0.51 mm in the left-hand lay direction. Both ends of the coil are secured to the mandrel before cutting wires to keep the coil from relaxing into an increased diameter. The coil is then wrapped with an 6.4 mm wide of the thinner, substantially impermeable ePTFE/FEP insulating tape insulating tape with about 5 layers (with the FEP-coated side facing the wire) and another wrap with the same tape in the opposite lay (also with the FEP-coated side facing the wire) with an additional 5 layers. The coil is then heated at 320° C. for approximately 5 minutes. The pacing coil is removed from mandrel by stretching the silver-plated copper wire until the coil is free to slide on mandrel and then the ends are trimmed off to achieve the desired length.

A stainless steel tube (0.53 mm outside diameter, 0.41 mm inside diameter and 7.6 mm length) is inserted into proximal end of pacing coil until nearly flush. The pacing coil is inserted into the lumen of the lead body. The tube and the proximal end of the pacing coil are then inserted into the female socket of the pin connector until fully seated and the pin connector is flush with the inner tube of the IS-4 connector. The pacing coil is then trimmed flush with the tip housing and then an additional 3.7 mm is trimmed from the same end. A suitable fixation helix and post component is obtained. A 0.51 mm diameter by 3.05 mm long stainless steel wire is inserted into the tip end of pacing coil until flush with end.

This end is inserted into the sleeve portion of the post/fixation helix assembly and crimped together, securing the post to the coil both mechanically and electrically. The pacing coil conductor is then inserted into the distal end tip housing of the previously manufactured lead. With the fixation helix located within the tubular housing provided for the pacing electrode, the tab feature, if applicable, on the tip housing is bent inward to create the thread guide. The fixation helix should extend and retract easily (within 3-10 rotations of the pacing coil from the proximal end of the lead assembly).

The fixation helix is then fully retracted into the tubular tip housing (in the proximal direction, by rotating the proximal end of the pacing coil in the opposite direction). The pin connector is nested onto the pacing coil adjacent to the IS-4 inner tube and crimped on proximal of pin connector flange. Finally, the IS-4 cap is placed over the pin connector and threaded onto the IS-4 inner tube until fully seated into sensing contact and sealed with silicone or epoxy adhesive.

A porous ePTFE is wrapped over the end of a 1.6 mm construction mandrel and then radially wrapped 6.4 mm wide by 22 mm long tape of porous ePTFE previously coated with the previously described TFE/PMVE fluoroelastomer copolymer containing approximately 1 mg of dexamethasone sodium phosphate with the wraps held in place with a fluoropolymer adhesive that may also contain dexamethasone sodium phosphate. The drug-loaded film tube is then removed from the construction mandrel and slid onto the tubular housing on the distal tip of the lead that was previously covered with porous ePTFE/FEP tape and attached with the fluoropolymer adhesive. The drug loaded film tube may also include flange-like features as previously described to allow for a more atraumatic tip.

Torque is applied to the pin connector sufficient to cause the fixation helix to rotate, extend distally and pierce the film covering over distal end of the tubular housing. Manual manipulation of the film may be required to aid the helix in piercing the film.

The lead of the present invention has good fatigue resistance. Leads of 5 French diameter were manufactured in accordance with the second manufacturing description presented above. These leads were tested in a cyclic 180 degree bending test as will be further described (plus and minus 90 degrees) through a radius of curvature of ≤6 mm wherein all five samples tested of the present lead survived in excess of 3,000,000 cycles without failure (i.e., they survived more than 100,000 cycles, more than 250,000 cycles, more than 500,000 cycles, more than 1,000,000 cycles, more than 1,500,000 cycles, more than 2,000,000 cycles, more than 2,500,000 cycles). All samples tested (all of which included pacing coils) of a commercially available lead in this test failed at considerably fewer cycles. Failure was identified as a significant increase in electrical resistance of the test sample and confirmed by presence of a visible fracture in any conductor.

The inventive leads also excelled in a comparative test for abrasion resistance as described below.

Flex testing (a bending fatigue test) and abrasion testing were performed on samples of the inventive leads built according to the second of the above manufacturing descriptions. Commercially available leads were also tested as controls.

Flex testing was conducted in the following manner.

A test fixture was constructed in accordance with the FIG. 106 of CENELEC test standard 45502-2-2:2008, section 23.5, with the exception that the fixture radius was 2.17 mm.

The bending radius along the longitudinal centerline of any lead under test varied as a function of the diameter of the test sample.

The test machine was constructed such that the fixture alternately oscillated 90+0/−5 degrees both sides from vertical and the test sample flexed in the bell mouth of the fixture, in accordance with the above-mentioned test standard.

A load of 235 g was used, and in accordance with the above-mentioned test standard was sufficient to assure that the centerline of the test segment conformed to the bending radius was attached to the lower end of a thin, flexible PTFE line strung through the test segment so that it conformed to the bending radius.

The oscillating rate was set at 4 Hz.

Samples were subjected to EtO sterilization (54 deg C., total cycle time of about 15 hours). Commercially available test samples had been sterilized by the manufacturer and, therefore, were not subjected to an additional sterilization cycle.

All flex-tested lead body samples were taken from lead body portions proximal of the SVC electrode. Individual test samples were taken from single leads.

An electrical connector was attached to all conductors at each end of the sample; the two connectors from the two sample ends were then connected to an ohmmeter. A sample was deemed to have failed upon a 0.02 Ohm increase in resistance. Visual inspection was then performed to verify fracture of one or more conductors. Five samples of each sample type were tested.

Flex testing was performed on samples of the inventive lead built according to the second of the above provided manufacturing descriptions, as well on ENDOTAK RELIANCE® G ICD leads (Model 0185 L, Boston Scientific, Natick, Mass.). The ENDOTAK RELIANCE leads were chosen as the basis for comparison as they appear to have the best clinical history for longest implant life in the industry at present. Samples of the present invention all exceeded 3 million cycles without failure; ENDOTAK RELIANCE lead samples all failed prior to 300,000 cycles. Note that the ENDOTAK RELIANCE lead samples are of asymmetric transverse cross section while the inventive test lead samples were all of symmetric transverse cross section whereby sample orientation did not matter. Consequently, three of the ENDOTAK RELIANCE lead samples were oriented in one direction while the other two were oriented at 90 degrees with respect to the orientation of the first three. Test results are presented in Table 1; orientation of the ENDOTAK RELIANCE leads in the bending fixture is indicated in the table where the adjacent vertical left and right lines shown in the table represent the bending surfaces.

TABLE 1

| Sample | Cycles to end of test | Conductor Failure | Orientation |
|---|---|---|---|
| Inventive | 3,396,044 | no | n/a |
| Inventive | 3,389,961 | no | n/a |
| Inventive | 3,390,601 | no | n/a |
| Inventive | 3,383,701 | no | n/a |
| Inventive | 3,344,911 | no | n/a |
| ENDOTAK | 99,775 | yes |  |
| ENDOTAK | 75,892 | yes |  |
| ENDOTAK | 109,633 | yes |  |
| ENDOTAK | 299,802 | yes |  |
| ENDOTAK | 276,186 | yes |  |

Abrasion testing was performed as follows.

Figure 23:
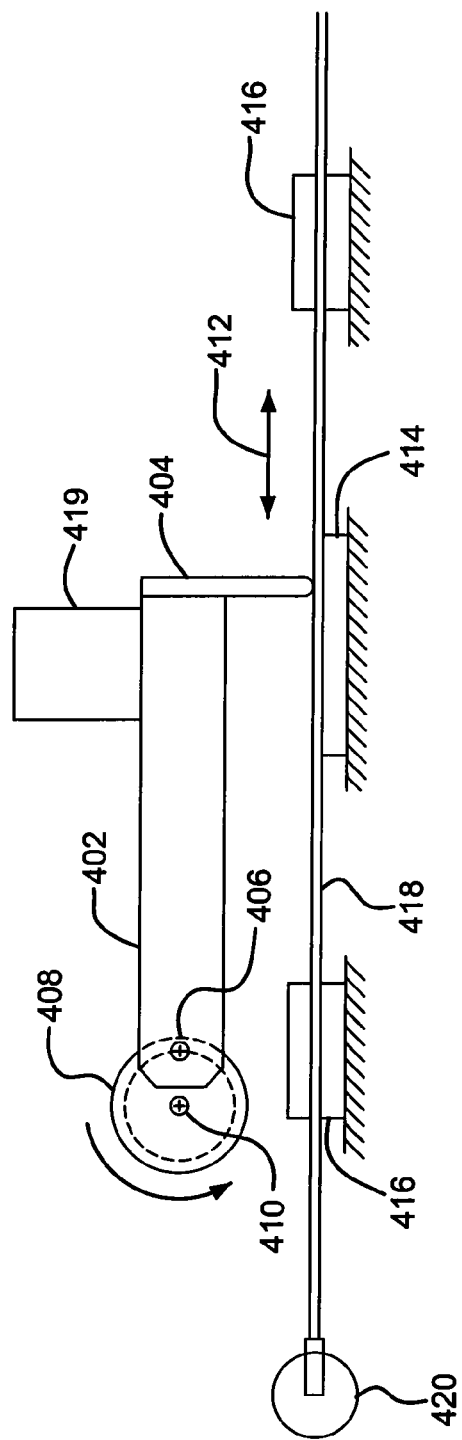
FIG. 23 is a schematic side view of an abrasion tester for evaluating the abrasion resistance of an implantable lead.

First, an ICD lead abrasion tester was constructed in the following manner, as shown generally by the schematic side view of FIG. 23.

An aluminum arm 402 (14 cm long, 2 cm wide, 0.5 cm thick) was fabricated and a titanium blade 404 was attached by screws to one end of arm 402. Blade 404 was 2.5 cm high, 1.5 cm wide and 1.59 mm thick. One end of the blade was shaped to a full radius of 0.795 mm in order to simulate the smallest edge of a typical ICD generator. The blade 404 was attached to arm 402 such the flat end was flush with the arm and the lower end of blade 404 extended about 0.5 cm below arm 402.

The other end of the arm was connected to the crankpin 406 of a circular plate 408 that served as a crankshaft. The center of circular plate 408 was attached to a shaft 410 of an electric motor (not shown) such that rotation of circular plate 408 by the electric motor caused blade 402 to translate back and forth as indicated by arrow 412. The rotation speed and translation distance (stroke length) were set to 96 revolutions/min and 1.3 cm, respectively.

An aluminum block 414 (2.5 cm long, 3.0 cm wide, 2.0 cm thick) was obtained. A groove was cut into the 2.5 cm by 3.0 cm upper surface of the block along the middle of the 2.5 cm length, in order to provide support for and to center the lead sample. The upper surface of block 414 was centered to the movement of the blade.

Two clamps 416 were provided on a stationary platform to hold a lead sample 418 fixed in position.

Weights 419 in the form of metal washers were placed on top of aluminum arm 402 to ensure contact between the blade and the test sample. A force gauge (Ametek Accuforce III, Largo Fla. 33773) was temporarily attached to the lower, radiused edge of blade 404. Washers were added until the force required to raise the arm reached 285 g.

A 24 volt power source was obtained, one pole 420 of which was connected to all of the conductors of the test sample. The other pole of the power source was connected to the rotating circular plate 408, which was in electrical contact with arm 402 and blade 404.

A proximity sensor was located adjacent to the aluminum arm and was used to detect the number of back and forth translations of the blade. The output of the detector was connected to a counter. Each back and forth translation of the blade was counted as a single cycle (i.e., one full revolution of circular plate 408). The counting circuit included an electrical feedback loop that was designed such that the test was stopped once electrical contact was made between the blade and the test sample conductor(s) (i.e., failure occurred). That is, the circuit was completed due to blade 404 making electrical contact with any of the outer conductors of test lead 418 as a result of abrasion through the insulation on the conductors.

Electrical contact was defined as a resistance reading through the blade to the lead body conductor of less than or equal to 3300 ohms. In all cases, electrical contact between the blade and the lead occurred once any of the outer conductors of the lead 418 were visibly exposed.

Test samples were prepared in the following manner.

Samples were subjected to EtO sterilization (54 degrees C., total cycle time of about 15 hours). Commercially available test samples had been sterilized by the manufacturer and, therefore, were not subjected to an additional sterilization cycle.

All abrasion-tested lead body samples were taken from lead body portions proximal to the electrodes. Individual test samples were taken from single leads.

An electrical connector was attached to all conductors at one end of the test sample; the connector was then connected to pole 420.

Testing was conducted as follows.

A 1.5 cm portion of the test sample was positioned inside the grooves of the block face, under the blade. The sample was fixed in position by securing both ends with the clamps attached to the stationary platform.

The test was initiated and continued until failure occurred.

Samples were tested and the values for the cycles to failure are shown in Table 2. Abrasion testing was performed on additional samples of the ENDOTAK RELIANCE® G ICD leads described above with regard to flex testing. Abrasion testing was also performed on the RIATA® ST Optim™ Defibrillation lead, Model 7022 (St. Jude Medical, St. Paul Minn.). The RIATA ST Optim lead was chosen because of its small diameter and reported abrasion resistance. It is noted that the ENDOTAK RELIANCE lead samples are of asymmetric transverse cross section as described previously. The inventive test lead samples were all of symmetric transverse cross section while the RIATA ST Optim are substantially symmetrical in transverse cross section, consisting of a central pacing coil centered along the longitudinal axis of the lead and additionally having three pairs of conductors extending along the length of the lead with the three pairs spaced radially apart 120 degrees with insulating material of the lead body between each of the three pairs. The three pairs of conductors are located closer to the outer surface of the lead body than the pacing coil. Abrasion test results of the RIATA lead may therefore vary as a function of whether the blade 404 of the tester is substantially centered above a pair of conductors or alternatively is substantially centered above the insulating material between adjacent conductor pairs. The RIATA lead orientations were chosen at random while the ENDOTAK leads were oriented so that the portion of the pacing coil closest to the surface of the lead body was located closest to blade 404.

Both the 4-layer and 6-layer fluoroelastomer-coated ePTFE inventive samples were made as described in the second manufacturing description provided above.

TABLE 2

| Lead Type | Cycles to Failure |
|---|---|
| ENDOTAK | 3,625 |
| ENDOTAK | 1,513 |
| ENDOTAK | 2,137 |
| ENDOTAK | 2,366 |
| ENDOTAK | 2,374 |
| RIATA | 73,225 |
| RIATA | 31,407 |
| RIATA | 5,143 |
| Inventive 4-Layer | 12,225 |
| Inventive 4-Layer | 14,531 |
| Inventive 4-Layer | 14,783 |
| Inventive 4-Layer | 17,284 |
| Inventive 4-Layer | 33,581 |
| Inventive 6-Layer | 100,375 |
| Inventive 6-Layer | 85,565 |
| Inventive 6-Layer | 71,374 |

In addition to being directed to the embodiments described above and claimed below, the present invention is further directed to embodiments having different combinations of the features described above and claimed below. As such, the invention is also directed to other embodiments having any other possible combination of the dependent features claimed below.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein.

We claim:

1. An Implantable cardioverter defibrillator lead body comprising a length extending between a proximal end incorporating an electrical connector and a distal end and having at least one insulated portion and at least two electrically conductive portions that are electrically independent from each other, wherein an electrical conductor extends between the electrical connector located at the proximal end and each of the electrically conductive portions, each of these electrical conductors comprising a length of insulated wire that has been folded in half with a 180 degree bend and with each half parallel to and adjacent to the other half in a helical winding extending along at least a portion of the length wherein the 180 degree bend is uninsulated and comprises one of the electrically conductive portions, and wherein when subjected to a bending fatigue test, said Implantable cardioverter defibrillator lead body survives a number of cycles up to about 3,500,000 and in excess of 300,000; wherein for each cycle, the implantable cardioverter defibrillator lead body is oscillated substantially 90 degrees both sides from vertical, in accordance with CENELEC test standard 45502-2-2:2008, section 23.5, in which the fixture radius is 2.17 mm and oscillating frequency is 4 Hz.

2. An Implantable cardioverter defibrillator lead body according to claim 1 wherein said Implantable cardioverter defibrillator lead body survives a number of cycles in excess of 500,000.

3. An Implantable cardioverter defibrillator lead body according to claim 1 wherein said Implantable cardioverter defibrillator lead body survives a number of cycles in excess of 1,000,000.

4. An Implantable cardioverter defibrillator lead body according to claim 1 wherein said Implantable cardioverter defibrillator lead body survives a number of cycles in excess of 2,000,000.

5. An Implantable cardioverter defibrillator lead body according to claim 1 wherein said Implantable cardioverter defibrillator lead body survives a number of cycles in excess of 3,000,000.

6. An Implantable cardioverter defibrillator lead body according to claim 1 wherein said Implantable cardioverter defibrillator lead body has a maximum diameter of 2 mm or less.

7. An Implantable cardioverter defibrillator lead body according to claim 2 wherein said Implantable cardioverter defibrillator lead body has a maximum diameter of 2 mm or less.

8. An Implantable cardioverter defibrillator lead body according to claim 3 wherein said Implantable cardioverter defibrillator lead body has a maximum diameter of 2 mm or less.

9. An Implantable cardioverter defibrillator lead body according to claim 4 wherein said Implantable cardioverter defibrillator lead body has a maximum diameter of 2 mm or less.

10. An Implantable cardioverter defibrillator lead body according to claim 5 wherein said Implantable cardioverter defibrillator lead body has a maximum diameter of 2 mm or less.

11. An Implantable cardioverter defibrillator lead body according to claim 1 wherein the number of cycles represents an average number of cycles for five leads of the same type.

12. An Implantable cardioverter defibrillator lead body according to claim 3 wherein the number of cycles represents an average number of cycles for five leads of the same type.

13. An Implantable cardioverter defibrillator lead body according to claim 3 wherein the number of cycles represents an average number of cycles for five leads of the same type.

14. An Implantable cardioverter defibrillator lead body according to claim 4 wherein the number of cycles represents an average number of cycles for five leads of the same type.

15. An Implantable cardioverter defibrillator lead body according to claim 5 wherein the number of cycles represents an average number of cycles for five leads of the same type.

16. An Implantable cardioverter defibrillator lead body according to claim 6 wherein the number of cycles represents an average number of cycles for five leads of the same type.

17. An Implantable cardioverter defibrillator lead body according to claim 7 wherein the number of cycles represents an average number of cycles for five leads of the same type.

18. An Implantable cardioverter defibrillator lead body according to claim 8 wherein the number of cycles represents an average number of cycles for five leads of the same type.

19. An Implantable cardioverter defibrillator lead body according to claim 9 wherein the number of cycles represents an average number of cycles for five leads of the same type.

20. An Implantable cardioverter defibrillator lead body according to claim 10 wherein the number of cycles represents an average number of cycles for five leads of the same type.

* * * * *